United States Patent
Khairkhahan et al.

(10) Patent No.: US 11,413,145 B2
(45) Date of Patent: Aug. 16, 2022

(54) COAPTATION ENHANCEMENT IMPLANT, SYSTEM, AND METHOD

(71) Applicant: Polares Medical Inc., Palo Alto, CA (US)

(72) Inventors: Alexander Khairkhahan, Palo Alto, CA (US); Michael D. Lesh, Mill Valley, CA (US)

(73) Assignee: Polares Medical Inc., Palo Alto, CA (US)

( * ) Notice: Subject to any disclaimer, the term of this patent is extended or adjusted under 35 U.S.C. 154(b) by 0 days.

(21) Appl. No.: 17/480,684

(22) Filed: Sep. 21, 2021

(65) Prior Publication Data
US 2022/0039944 A1  Feb. 10, 2022

Related U.S. Application Data

(63) Continuation of application No. 16/675,565, filed on Nov. 6, 2019, which is a continuation of application (Continued)

(51) Int. Cl.
  *A61F 2/24* (2006.01)
  *A61B 17/04* (2006.01)
  (Continued)

(52) U.S. Cl.
  CPC .......... *A61F 2/246* (2013.01); *A61B 17/0401* (2013.01); *A61B 17/064* (2013.01);
  (Continued)

(58) Field of Classification Search
  CPC ...... A61F 2/246; A61F 2/2454; A61F 2/2466; A61F 2/2457
  See application file for complete search history.

(56) References Cited

U.S. PATENT DOCUMENTS 3,491,376 A   1/1970   Shiley
3,503,079 A   3/1970   Smith
(Continued)

FOREIGN PATENT DOCUMENTS

CN   102256568   12/2002
CN   1984621    6/2007
(Continued)

OTHER PUBLICATIONS

Biocina et al., Mitral Valve Repair With The New Mitrofast® Repair System, Dubrava University Hospital, Zagreb, Crotia, Mitrofast Abstract European Soc CVS 55th Congress—May 11-14, 2006 Suppl 1 to vol. 5.
(Continued)

*Primary Examiner* — Julian W Woo
(74) *Attorney, Agent, or Firm* — Knobbe, Martens, Olson & Bear, LLP

(57) ABSTRACT

Implants, implant systems, and methods for treatment of mitral valve regurgitation and other valve diseases generally include a coaptation assist body which remains within the blood flow path as the leaflets of the valve move, the valve bodies often being relatively thin, elongate (along the blood flow path), and/or conformable structures which extend laterally from commissure to commissure, allowing the native leaflets to engage and seal against the large, opposed surfaces on either side of the valve body during the heart cycle phase when the ventricle contracts to empty that chamber of blood, and allows blood to pass around the valve body so that blood flows from the atrium to the ventricle during the filling phase of the heart cycle. Separate deployment of independent anchors near each of the commissures may facilitate positioning and support of an exemplary triangular valve body, with a third anchor being deployed in the ventricle. An outer surface of the valve body may
(Continued)

accommodate tissue ingrowth or endothelialization, while a fluid-absorbing matrix can swell after introduction into the heart. The valve body shape may be selected after an anchor has been deployed, and catheter-based deployment systems may have a desirable low profile.

20 Claims, 44 Drawing Sheets

Related U.S. Application Data

No. 15/475,629, filed on Mar. 31, 2017, now Pat. No. 10,470,883, which is a continuation of application No. 14/500,470, filed on Sep. 29, 2014, now Pat. No. 9,610,163, which is a continuation of application No. 13/099,532, filed on May 3, 2011, now Pat. No. 8,845,717.

(60) Provisional application No. 61/437,397, filed on Jan. 28, 2011.

(51) Int. Cl.
  A61B 17/064 (2006.01)
  A61B 17/068 (2006.01)
  A61B 17/12 (2006.01)
  A61B 17/00 (2006.01)

(52) U.S. Cl.
  CPC .......... A61B 17/068 (2013.01); A61F 2/2454 (2013.01); A61F 2/2466 (2013.01); A61B 17/12122 (2013.01); A61B 17/12172 (2013.01); A61B 2017/00867 (2013.01); A61B 2017/048 (2013.01); A61B 2017/0412 (2013.01); A61B 2017/0448 (2013.01); A61B 2017/0464 (2013.01); A61B 2017/0649 (2013.01); A61F 2/2457 (2013.01); A61F 2250/0003 (2013.01)

(56) References Cited

U.S. PATENT DOCUMENTS

| | | |
|---|---|---|
| 3,656,185 A | 4/1972 | Carpentier |
| 3,671,979 A | 6/1972 | Moulopoulos |
| 3,874,388 A | 4/1975 | King et al. |
| 3,898,701 A | 8/1975 | La Russa |
| 3,938,197 A | 2/1976 | Milo |
| 4,007,743 A | 2/1977 | Blake |
| 4,011,601 A | 3/1977 | Clune et al. |
| 4,042,979 A | 8/1977 | Angell |
| 4,078,268 A | 3/1978 | Possis |
| 4,204,283 A | 5/1980 | Bellhouse et al. |
| 4,218,783 A | 8/1980 | Reul et al. |
| 4,261,342 A | 4/1981 | Aranguren Duo |
| 4,263,680 A | 4/1981 | Ruel et al. |
| 4,275,469 A | 6/1981 | Gabbay |
| RE31,040 E | 9/1982 | Possis |
| 4,352,211 A | 10/1982 | Parravicini |
| 4,488,318 A | 12/1984 | Kaster |
| 4,490,859 A | 1/1985 | Black et al. |
| 4,491,986 A | 1/1985 | Gabbay |
| 4,561,129 A | 12/1985 | Arpesella |
| 4,687,483 A | 8/1987 | Fisher et al. |
| 4,705,516 A | 11/1987 | Barone et al. |
| 4,759,758 A | 7/1988 | Gabbay |
| 4,790,843 A | 12/1988 | Carpentier et al. |
| 4,960,424 A | 10/1990 | Grooters |
| 4,994,077 A | 2/1991 | Dobben |
| 5,002,567 A | 3/1991 | Bona et al. |
| 5,078,737 A | 1/1992 | Bona et al. |
| 5,131,905 A | 7/1992 | Grooters |
| 5,197,980 A | 3/1993 | Gorshkov et al. |
| 5,217,484 A | 6/1993 | Marks |
| 5,258,023 A | 11/1993 | Reger |
| 5,332,402 A | 7/1994 | Teitelbaum |
| 5,344,442 A | 9/1994 | Deac |
| 5,370,662 A | 12/1994 | Stone et al. |
| 5,397,347 A | 3/1995 | Cuilleron et al. |
| 5,397,348 A | 3/1995 | Campbell et al. |
| 5,413,599 A | 5/1995 | Imachi et al. |
| 5,487,760 A | 1/1996 | Villafana |
| 5,500,015 A | 3/1996 | Deac |
| 5,522,886 A | 6/1996 | Milo |
| 5,554,186 A | 9/1996 | Guo et al. |
| 5,582,616 A | 12/1996 | Bolduc et al. |
| 5,593,435 A | 1/1997 | Carpentier et al. |
| 5,626,613 A | 5/1997 | Schmieding |
| 5,658,313 A | 8/1997 | Thal |
| 5,662,683 A | 9/1997 | Kay |
| 5,662,704 A | 9/1997 | Gross |
| 5,716,370 A | 2/1998 | Williamson, IV et al. |
| 5,733,331 A | 3/1998 | Peredo |
| 5,824,065 A | 10/1998 | Gross |
| 5,824,066 A | 10/1998 | Gross |
| 5,824,067 A | 10/1998 | Gross |
| 5,855,601 A | 1/1999 | Bessler et al. |
| 5,888,240 A | 3/1999 | Carpentier et al. |
| 5,957,949 A | 9/1999 | Leonhardt et al. |
| 6,007,577 A | 12/1999 | Vanney et al. |
| 6,024,096 A | 2/2000 | Buckberg |
| 6,042,607 A | 3/2000 | Williamson, IV et al. |
| 6,045,497 A | 4/2000 | Schweich et al. |
| 6,045,573 A | 4/2000 | Wenstrom et al. |
| 6,063,114 A | 5/2000 | Nash et al. |
| 6,066,160 A | 5/2000 | Colvin et al. |
| 6,086,612 A | 7/2000 | Jansen |
| 6,113,631 A | 9/2000 | Jansen |
| 6,162,233 A | 12/2000 | Williamson, IV et al. |
| 6,217,610 B1 | 4/2001 | Carpentier et al. |
| 6,221,104 B1 | 4/2001 | Buckberg et al. |
| 6,250,308 B1 | 6/2001 | Cox |
| 6,264,602 B1 | 7/2001 | Mortier et al. |
| 6,287,339 B1 | 9/2001 | Vazquez et al. |
| 6,296,662 B1 | 10/2001 | Caffey |
| 6,299,637 B1 | 10/2001 | Shaolian et al. |
| 6,312,447 B1 | 11/2001 | Grimes |
| 6,312,464 B1 | 11/2001 | Navia |
| 6,332,893 B1 | 12/2001 | Mortier et al. |
| 6,358,277 B1 | 3/2002 | Duran |
| 6,383,147 B1 | 5/2002 | Stobie |
| 6,391,053 B1 | 5/2002 | Brendzel et al. |
| 6,391,054 B2 | 5/2002 | Carpentier et al. |
| 6,402,679 B1 | 6/2002 | Mortier et al. |
| 6,402,780 B2 | 6/2002 | Williamson, IV et al. |
| 6,409,758 B2 | 6/2002 | Stobie et al. |
| 6,419,695 B1 | 7/2002 | Gabbay |
| 6,439,237 B1 | 8/2002 | Buckberg et al. |
| 6,450,171 B1 | 9/2002 | Buckberg et al. |
| 6,451,024 B1 | 9/2002 | Thompson et al. |
| 6,454,799 B1 | 9/2002 | Schreck |
| 6,458,153 B1 | 10/2002 | Bailey et al. |
| 6,482,228 B1 | 11/2002 | Norred |
| 6,540,782 B1 | 4/2003 | Snyders |
| 6,544,167 B2 | 4/2003 | Buckberg et al. |
| 6,565,603 B2 | 5/2003 | Cox |
| 6,569,198 B1 | 5/2003 | Wilson |
| 6,602,288 B1 | 8/2003 | Cosgrove et al. |
| 6,602,289 B1 | 8/2003 | Colvin et al. |
| 6,626,930 B1 | 9/2003 | Allen et al. |
| 6,629,534 B1 | 10/2003 | Goar et al. |
| 6,652,578 B2 | 11/2003 | Bailey et al. |
| 6,676,698 B2 | 1/2004 | McGuckin, Jr. et al. |
| 6,682,559 B2 | 1/2004 | Myers et al. |
| 6,702,852 B2 | 3/2004 | Stobie et al. |
| 6,719,790 B2 | 4/2004 | Brendzel et al. |
| 6,752,813 B2 | 6/2004 | Goldfarb et al. |
| 6,764,510 B2 | 7/2004 | Vidlund et al. |
| 6,780,200 B2 | 8/2004 | Jansen |
| 6,790,237 B2 | 9/2004 | Stinson |
| 6,797,002 B2 | 9/2004 | Spence et al. |
| 6,800,090 B2 | 10/2004 | Alferness et al. |

(56) References Cited

U.S. PATENT DOCUMENTS

| | | |
|---|---|---|
| 6,805,710 B2 | 10/2004 | Bolling et al. |
| 6,821,297 B2 | 11/2004 | Snyders |
| 6,837,247 B2 | 1/2005 | Buckberg et al. |
| 6,840,246 B2 | 1/2005 | Downing |
| 6,846,324 B2 | 1/2005 | Stobie |
| 6,869,444 B2 | 3/2005 | Gabbay |
| 6,908,478 B2 | 6/2005 | Alferness et al. |
| 6,911,043 B2 | 6/2005 | Myers et al. |
| 6,926,730 B1 | 8/2005 | Nguyen et al. |
| 6,966,925 B2 | 11/2005 | Stobie |
| 6,991,649 B2 | 1/2006 | Sievers |
| 6,997,950 B2 | 2/2006 | Chawla |
| 7,018,408 B2 | 3/2006 | Bailey et al. |
| 7,037,333 B2 | 5/2006 | Myers et al. |
| 7,048,754 B2 | 5/2006 | Martin et al. |
| 7,056,280 B2 | 6/2006 | Buckberg et al. |
| 7,070,618 B2 | 7/2006 | Streeter |
| 7,077,861 B2 | 7/2006 | Spence |
| 7,077,862 B2 | 7/2006 | Vidlund et al. |
| 7,083,628 B2 | 8/2006 | Bachman |
| 7,087,064 B1 | 8/2006 | Hyde |
| 7,112,207 B2 | 9/2006 | Allen et al. |
| 7,122,043 B2 | 10/2006 | Greenhalgh et al. |
| 7,160,322 B2 | 1/2007 | Gabbay |
| 7,166,126 B2 | 1/2007 | Spence et al. |
| 7,175,656 B2 | 2/2007 | Khairkhahan |
| 7,195,641 B2 | 3/2007 | Palmaz et al. |
| 7,217,284 B2 | 5/2007 | Houser et al. |
| 7,226,467 B2 | 6/2007 | Lucatero et al. |
| 7,275,546 B2 | 10/2007 | Buckberg et al. |
| 7,291,168 B2 | 11/2007 | Macoviak et al. |
| 7,294,148 B2 | 11/2007 | McCarthy |
| 7,296,577 B2 | 11/2007 | Taylor et al. |
| 7,316,706 B2 | 1/2008 | Bloom et al. |
| 7,320,704 B2 | 1/2008 | Lashinski et al. |
| 7,335,213 B1 | 2/2008 | Hyde et al. |
| 7,338,520 B2 | 3/2008 | Bailey et al. |
| 7,341,584 B1 | 3/2008 | Starkey |
| 7,357,814 B2 | 4/2008 | Gabbay |
| 7,374,572 B2 | 5/2008 | Gabbay |
| RE40,377 E | 6/2008 | Williamson, IV et al. |
| 7,381,220 B2 | 6/2008 | Macoviak et al. |
| 7,396,364 B2 | 7/2008 | Moaddeb et al. |
| 7,404,824 B1 | 7/2008 | Webler et al. |
| 7,435,257 B2 | 10/2008 | Lashinski et al. |
| 7,445,630 B2 | 11/2008 | Lashinski et al. |
| 7,455,689 B2 | 11/2008 | Johnson |
| 7,485,143 B2 | 2/2009 | Webler et al. |
| 7,510,573 B2 | 3/2009 | Gabbay |
| 7,510,576 B2 | 3/2009 | Langberg et al. |
| 7,527,646 B2 | 5/2009 | Rahdert et al. |
| 7,527,647 B2 | 5/2009 | Spence |
| 7,530,998 B1 | 5/2009 | Starkey |
| 7,534,259 B2 | 5/2009 | Lashinski et al. |
| 7,556,645 B2 | 7/2009 | Lashinski et al. |
| 7,559,936 B2 | 7/2009 | Levine |
| 7,563,267 B2 | 7/2009 | Goldfarb et al. |
| 7,563,273 B2 | 7/2009 | Goldfarb et al. |
| 7,591,847 B2 | 9/2009 | Navia et al. |
| 7,608,091 B2 | 10/2009 | Goldfarb et al. |
| 7,611,534 B2 | 11/2009 | Kapadia et al. |
| 7,621,948 B2 | 11/2009 | Herrmann et al. |
| 7,648,532 B2 | 1/2010 | Greenhalgh et al. |
| 7,655,015 B2 | 2/2010 | Goldfarb et al. |
| 7,658,762 B2 | 2/2010 | Lashinski et al. |
| 7,658,763 B2 | 2/2010 | Stobie |
| 7,666,224 B2 | 2/2010 | Vidlund et al. |
| 7,674,286 B2 | 3/2010 | Alfieri et al. |
| 7,678,145 B2 | 3/2010 | Vidlund et al. |
| 7,682,391 B2 | 3/2010 | Johnson |
| 7,691,144 B2 | 4/2010 | Chang et al. |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,736,388 B2 | 6/2010 | Goldfarb et al. |
| 7,740,638 B2 | 6/2010 | Hyde |
| 7,744,609 B2 | 6/2010 | Allen et al. |
| 7,753,923 B2 | 7/2010 | St. Goar et al. |
| 7,758,491 B2 | 7/2010 | Buckner et al. |
| 7,758,595 B2 | 7/2010 | Allen et al. |
| 7,776,084 B2 | 8/2010 | Johnson |
| 7,785,366 B2 | 8/2010 | Maurer et al. |
| 7,799,038 B2 | 9/2010 | Sogard et al. |
| 7,803,187 B2 | 9/2010 | Hauser |
| 7,819,915 B2 | 10/2010 | Stobie et al. |
| 7,846,203 B2 | 12/2010 | Cribier |
| 7,887,552 B2 | 2/2011 | Bachman |
| 7,901,454 B2 | 3/2011 | Kapadia et al. |
| 7,909,866 B2 | 3/2011 | Stobie |
| 7,914,576 B2 | 3/2011 | Navia et al. |
| 7,927,370 B2 | 4/2011 | Webler et al. |
| 7,935,144 B2 | 5/2011 | Robin et al. |
| 7,935,145 B2 | 5/2011 | Alfieri et al. |
| 7,938,827 B2 | 5/2011 | Hauck et al. |
| 7,942,928 B2 | 5/2011 | Webler et al. |
| 7,951,195 B2 | 5/2011 | Antonsson et al. |
| 7,951,196 B2 | 5/2011 | McCarthy |
| 7,955,385 B2 | 6/2011 | Crittenden |
| 7,959,673 B2 | 6/2011 | Carpentier et al. |
| 7,981,139 B2 | 7/2011 | Martin et al. |
| 7,988,725 B2 | 8/2011 | Gross et al. |
| 7,993,396 B2 | 8/2011 | McCarthy |
| 7,998,151 B2 | 8/2011 | St. Goar et al. |
| 8,012,201 B2 | 9/2011 | Lashinski et al. |
| 8,012,202 B2 | 9/2011 | Alameddine |
| 8,016,882 B2 | 9/2011 | Macoviak et al. |
| 8,029,518 B2 | 10/2011 | Goldfarb et al. |
| 8,052,751 B2 | 11/2011 | Aklog et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,092,525 B2 | 1/2012 | Eliasen et al. |
| 8,118,866 B2 | 2/2012 | Herrmann et al. |
| 8,128,691 B2 | 3/2012 | Keranen |
| 8,133,272 B2 | 3/2012 | Hyde |
| 8,142,494 B2 | 3/2012 | Rahdert et al. |
| 8,142,495 B2 | 3/2012 | Hasenkam et al. |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,207 B2 | 5/2012 | Machold et al. |
| 8,187,299 B2 | 5/2012 | Goldfarb et al. |
| 8,187,323 B2 | 5/2012 | Mortier et al. |
| 8,204,605 B2 | 6/2012 | Hastings et al. |
| 8,206,439 B2 | 6/2012 | Gomez Duran |
| 8,216,230 B2 | 7/2012 | Hauck et al. |
| 8,216,256 B2 | 7/2012 | Raschdorf, Jr. et al. |
| 8,216,302 B2 | 7/2012 | Wilson et al. |
| 8,216,303 B2 | 7/2012 | Navia |
| 8,221,493 B2 | 7/2012 | Boyle et al. |
| 8,226,711 B2 | 7/2012 | Mortier et al. |
| 8,241,304 B2 | 8/2012 | Bachman |
| 8,241,351 B2 | 8/2012 | Cabiri |
| 8,252,050 B2 | 8/2012 | Maisano |
| 8,252,051 B2 | 8/2012 | Chau et al. |
| 8,262,725 B2 | 9/2012 | Subramanian |
| 8,277,502 B2 | 10/2012 | Miller et al. |
| 8,287,591 B2 | 10/2012 | Keidar et al. |
| 8,292,884 B2 | 10/2012 | Levine et al. |
| 8,308,796 B2 | 11/2012 | Lashinski et al. |
| 8,323,336 B2 | 12/2012 | Hill et al. |
| 8,337,390 B2 | 12/2012 | Ferrazzi |
| 8,353,956 B2 | 1/2013 | Miller et al. |
| 8,361,086 B2 | 1/2013 | Allen et al. |
| 8,377,118 B2 | 2/2013 | Lashinski et al. |
| 8,382,796 B2 | 2/2013 | Blaeser et al. |
| 8,382,828 B2 | 2/2013 | Roberts |
| 8,382,829 B1 | 2/2013 | Call et al. |
| RE44,075 E | 3/2013 | Williamson, IV et al. |
| 8,398,708 B2 | 3/2013 | Meiri et al. |
| 8,408,214 B2 | 4/2013 | Spenser |
| 8,413,573 B2 | 4/2013 | Rebecchi |
| 8,414,644 B2 | 4/2013 | Quadri et al. |

(56) References Cited

U.S. PATENT DOCUMENTS

| | | | |
|---|---|---|---|
| 8,449,606 B2 | 5/2013 | Eliasen et al. | |
| 8,454,683 B2 | 6/2013 | Rafiee et al. | |
| 8,470,028 B2 * | 6/2013 | Thornton | A61F 2/2463 623/2.36 |
| 8,500,800 B2 | 8/2013 | Maisano et al. | |
| 8,506,624 B2 | 8/2013 | Vidlund et al. | |
| 8,523,881 B2 | 9/2013 | Cabiri et al. | |
| 8,545,553 B2 | 10/2013 | Zipory et al. | |
| 8,608,797 B2 | 12/2013 | Gross et al. | |
| 8,657,872 B2 | 2/2014 | Seguin | |
| 8,690,939 B2 | 4/2014 | Miller et al. | |
| 8,715,342 B2 | 5/2014 | Zipory et al. | |
| 8,734,467 B2 | 5/2014 | Miller et al. | |
| 8,784,483 B2 | 7/2014 | Navia | |
| 8,790,394 B2 | 7/2014 | Miller et al. | |
| 8,795,352 B2 | 8/2014 | O'Beirne et al. | |
| 8,808,368 B2 | 8/2014 | Maisano et al. | |
| 8,845,717 B2 | 9/2014 | Khairkhahan et al. | |
| 8,858,623 B2 | 10/2014 | Miller et al. | |
| 8,888,843 B2 | 11/2014 | Khairkhahan et al. | |
| 8,888,844 B2 | 11/2014 | Eliasen et al. | |
| 8,911,494 B2 | 12/2014 | Hammer et al. | |
| 8,926,695 B2 | 1/2015 | Gross et al. | |
| 8,926,696 B2 | 1/2015 | Cabiri et al. | |
| 8,926,697 B2 | 1/2015 | Gross et al. | |
| 8,940,042 B2 | 1/2015 | Miller et al. | |
| 8,940,044 B2 | 1/2015 | Hammer et al. | |
| 9,005,279 B2 | 4/2015 | Gabbay | |
| 9,011,520 B2 | 4/2015 | Miller et al. | |
| 9,011,530 B2 | 4/2015 | Reich et al. | |
| 9,056,006 B2 | 6/2015 | Edelman et al. | |
| 9,119,719 B2 | 9/2015 | Zipory et al. | |
| 9,180,007 B2 | 11/2015 | Reich et al. | |
| 9,192,472 B2 | 11/2015 | Gross et al. | |
| 9,204,964 B2 | 12/2015 | Dahlgren et al. | |
| 9,232,999 B2 | 1/2016 | Maurer et al. | |
| 9,265,608 B2 | 2/2016 | Miller et al. | |
| 9,277,994 B2 | 3/2016 | Miller et al. | |
| 9,351,830 B2 | 5/2016 | Gross et al. | |
| 9,414,921 B2 | 8/2016 | Miller et al. | |
| 9,452,048 B2 | 9/2016 | O'beirne et al. | |
| 9,474,606 B2 | 10/2016 | Zipory et al. | |
| 9,526,613 B2 | 12/2016 | Gross et al. | |
| 9,549,817 B2 | 1/2017 | Rafiee | |
| 9,554,906 B2 | 1/2017 | Aklog et al. | |
| 9,561,104 B2 | 2/2017 | Miller et al. | |
| 9,592,118 B2 | 3/2017 | Khairkhahan et al. | |
| 9,592,121 B1 | 3/2017 | Khairkhahan | |
| 9,592,122 B2 | 3/2017 | Zipory et al. | |
| 9,610,162 B2 | 4/2017 | Zipory et al. | |
| 9,610,163 B2 | 4/2017 | Khairkhahan et al. | |
| 9,622,861 B2 | 4/2017 | Miller et al. | |
| 9,636,224 B2 | 5/2017 | Zipory et al. | |
| 9,662,209 B2 | 5/2017 | Gross et al. | |
| 9,713,530 B2 | 7/2017 | Cabiri et al. | |
| 9,724,192 B2 | 8/2017 | Sheps et al. | |
| 9,730,793 B2 | 8/2017 | Reich et al. | |
| 9,775,709 B2 | 10/2017 | Miller et al. | |
| 9,814,572 B2 | 11/2017 | Edelman et al. | |
| 9,872,769 B2 | 1/2018 | Gross et al. | |
| 9,883,943 B2 | 2/2018 | Gross et al. | |
| 9,918,840 B2 | 3/2018 | Reich et al. | |
| 9,937,042 B2 | 4/2018 | Cabiri et al. | |
| 9,949,828 B2 | 4/2018 | Sheps et al. | |
| 9,968,452 B2 | 5/2018 | Sheps et al. | |
| 9,968,454 B2 | 5/2018 | Reich et al. | |
| 9,974,653 B2 | 5/2018 | Gross et al. | |
| 10,028,832 B2 | 7/2018 | Quill et al. | |
| 10,098,737 B2 | 10/2018 | Miller et al. | |
| 10,123,874 B2 | 11/2018 | Khairkhahan et al. | |
| 10,130,472 B2 | 11/2018 | O'beirne et al. | |
| 10,166,098 B2 | 1/2019 | Khairkhahan et al. | |
| 10,195,030 B2 | 2/2019 | Gross et al. | |
| 10,226,342 B2 | 3/2019 | Kutzik et al. | |
| 10,251,635 B2 | 4/2019 | Khairkhahan et al. | |
| 10,265,170 B2 | 4/2019 | Zipory et al. | |
| 10,299,793 B2 | 5/2019 | Zipory et al. | |
| 10,350,068 B2 | 7/2019 | Miller et al. | |
| 10,357,366 B2 | 7/2019 | Gross et al. | |
| 10,363,136 B2 | 7/2019 | Miller et al. | |
| 10,363,137 B2 | 7/2019 | Gross et al. | |
| 10,368,982 B2 | 8/2019 | Weber et al. | |
| 10,376,266 B2 | 8/2019 | Herman et al. | |
| 10,376,365 B2 | 8/2019 | Khairkhahan et al. | |
| 10,383,726 B2 | 8/2019 | Kramer | |
| 10,433,955 B2 | 10/2019 | Edelman et al. | |
| 10,449,046 B2 | 10/2019 | Rafiee | |
| 10,449,333 B2 | 10/2019 | Hammer et al. | |
| 10,470,882 B2 | 11/2019 | Gross et al. | |
| 10,470,883 B2 | 11/2019 | Khairkhahan et al. | |
| 10,478,303 B2 | 11/2019 | Khairkhahan et al. | |
| 10,492,909 B2 | 12/2019 | Miller et al. | |
| 10,500,048 B2 | 12/2019 | Khairkhahan et al. | |
| 10,512,542 B2 | 12/2019 | Khairkhahan et al. | |
| 10,517,719 B2 | 12/2019 | Miller et al. | |
| 10,543,088 B2 | 1/2020 | Lashinski | |
| 10,548,729 B2 | 2/2020 | Zipory et al. | |
| 10,548,731 B2 | 2/2020 | Lashinski et al. | |
| 10,561,498 B2 | 2/2020 | Gross et al. | |
| 10,568,738 B2 | 2/2020 | Sheps et al. | |
| 10,610,360 B2 | 4/2020 | Reich et al. | |
| 10,653,524 B2 | 5/2020 | Khairkhahan et al. | |
| 10,702,386 B2 | 7/2020 | Khairkhahan et al. | |
| 10,751,180 B2 | 8/2020 | Schewel | |
| 11,000,372 B2 | 5/2021 | Khairkhahan et al. | |
| 11,160,656 B2 | 11/2021 | Khairkhahan | |
| 2001/0007956 A1 | 7/2001 | Letac et al. | |
| 2001/0021872 A1 | 9/2001 | Bailey et al. | |
| 2002/0029080 A1 | 3/2002 | Mortier et al. | |
| 2002/0058995 A1 | 5/2002 | Stevens | |
| 2002/0116024 A1 | 8/2002 | Goldberg et al. | |
| 2002/0138135 A1 | 9/2002 | Duerig | |
| 2002/0188301 A1 | 12/2002 | Dallara et al. | |
| 2003/0023248 A1 | 1/2003 | Parodi | |
| 2003/0100943 A1 | 5/2003 | Bolduc | |
| 2003/0105474 A1 | 6/2003 | Bonutti | |
| 2003/0135263 A1 | 7/2003 | Rourke et al. | |
| 2003/0191497 A1 | 10/2003 | Cope | |
| 2003/0199975 A1 | 10/2003 | Gabbay | |
| 2004/0082956 A1 | 4/2004 | Baldwin et al. | |
| 2004/0088047 A1 | 5/2004 | Spence et al. | |
| 2004/0143323 A1 | 7/2004 | Chawla | |
| 2004/0172046 A1 | 9/2004 | Hlavka et al. | |
| 2004/0193217 A1 | 9/2004 | Lubbers et al. | |
| 2004/0210307 A1 | 10/2004 | Khairkhahan | |
| 2005/0004665 A1 | 1/2005 | Aklog | |
| 2005/0004668 A1 | 1/2005 | Aklog et al. | |
| 2005/0010287 A1 | 1/2005 | Macoviak et al. | |
| 2005/0075727 A1 | 4/2005 | Wheatley et al. | |
| 2005/0096740 A1 | 5/2005 | Langberg et al. | |
| 2005/0107871 A1 | 5/2005 | Realyvasquez | |
| 2005/0159810 A1 | 7/2005 | Filsoufi | |
| 2005/0177180 A1 | 8/2005 | Kaganov et al. | |
| 2005/0228495 A1 | 10/2005 | Macoviak | |
| 2005/0261708 A1 | 11/2005 | Pasricha et al. | |
| 2005/0283232 A1 | 12/2005 | Gabbay | |
| 2006/0058871 A1 | 3/2006 | Zakay et al. | |
| 2006/0122608 A1 | 6/2006 | Fallin et al. | |
| 2006/0149368 A1 | 7/2006 | Spence | |
| 2006/0190030 A1 | 8/2006 | To et al. | |
| 2006/0252984 A1 | 11/2006 | Rahdert et al. | |
| 2007/0005005 A1 | 1/2007 | Contiliano et al. | |
| 2007/0049970 A1 | 3/2007 | Belef et al. | |
| 2007/0093890 A1 * | 4/2007 | Eliasen | A61F 2/246 623/2.11 |
| 2007/0112352 A1 | 5/2007 | Sorensen et al. | |
| 2007/0112425 A1 | 5/2007 | Schaller et al. | |
| 2007/0118151 A1 | 5/2007 | Davidson | |
| 2007/0129758 A1 | 6/2007 | Saadat | |
| 2007/0185571 A1 | 8/2007 | Kapadia et al. | |
| 2007/0233239 A1 | 10/2007 | Navia et al. | |
| 2007/0239272 A1 | 10/2007 | Navia et al. | |
| 2007/0244554 A1 | 10/2007 | Rafiee et al. | |
| 2007/0244555 A1 | 10/2007 | Rafiee et al. | |

(56) References Cited

U.S. PATENT DOCUMENTS

| | | |
|---|---|---|
| 2007/0244556 A1 | 10/2007 | Rafiee et al. |
| 2007/0250160 A1 | 10/2007 | Rafiee |
| 2007/0255399 A1 | 11/2007 | Eliasen et al. |
| 2007/0265658 A1 | 11/2007 | Nelson et al. |
| 2007/0265700 A1 | 11/2007 | Eliasen et al. |
| 2007/0265702 A1 | 11/2007 | Lattouf |
| 2007/0293943 A1 | 12/2007 | Quinn |
| 2008/0065204 A1 | 3/2008 | Macoviak et al. |
| 2008/0109075 A1 | 5/2008 | Keranen |
| 2008/0125860 A1 | 5/2008 | Webler et al. |
| 2008/0125861 A1* | 5/2008 | Webler ............... A61B 17/064 623/2.36 |
| 2008/0195205 A1 | 8/2008 | Schwartz |
| 2008/0262609 A1 | 10/2008 | Gross et al. |
| 2008/0319541 A1 | 12/2008 | Filsoufi |
| 2009/0012354 A1 | 1/2009 | Wood |
| 2009/0088836 A1 | 4/2009 | Bishop et al. |
| 2009/0177277 A1 | 7/2009 | Milo |
| 2009/0234404 A1 | 9/2009 | Fitzgerald et al. |
| 2009/0259304 A1 | 10/2009 | O'Beirne et al. |
| 2009/0259307 A1 | 10/2009 | Gross et al. |
| 2009/0287304 A1 | 11/2009 | Dahlgren et al. |
| 2009/0326648 A1 | 12/2009 | Machold et al. |
| 2010/0069954 A1 | 3/2010 | Blaeser et al. |
| 2010/0121435 A1 | 5/2010 | Subramanian et al. |
| 2010/0131057 A1 | 5/2010 | Subramanian et al. |
| 2010/0161043 A1 | 6/2010 | Maisano et al. |
| 2010/0161047 A1 | 6/2010 | Cabiri et al. |
| 2010/0249947 A1 | 9/2010 | Lesh et al. |
| 2010/0262233 A1 | 10/2010 | He |
| 2010/0280603 A1 | 11/2010 | Maisano et al. |
| 2010/0280604 A1 | 11/2010 | Zipory et al. |
| 2010/0280605 A1 | 11/2010 | Hammer |
| 2010/0280606 A1 | 11/2010 | Naor |
| 2010/0286767 A1 | 11/2010 | Zipory et al. |
| 2010/0298929 A1 | 11/2010 | Thornton et al. |
| 2010/0312333 A1 | 12/2010 | Navia et al. |
| 2011/0004299 A1 | 1/2011 | Navia et al. |
| 2011/0082538 A1 | 4/2011 | Dahlgren et al. |
| 2011/0106245 A1 | 5/2011 | Miller et al. |
| 2011/0106247 A1 | 5/2011 | Miller et al. |
| 2011/0137397 A1 | 6/2011 | Chau et al. |
| 2011/0166649 A1 | 7/2011 | Gross et al. |
| 2011/0224785 A1 | 9/2011 | Hacohen |
| 2011/0288635 A1 | 11/2011 | Miller et al. |
| 2011/0301698 A1 | 12/2011 | Miller et al. |
| 2012/0016468 A1 | 1/2012 | Robin et al. |
| 2012/0022557 A1 | 1/2012 | Cabiri et al. |
| 2012/0022644 A1 | 1/2012 | Reich et al. |
| 2012/0078360 A1 | 3/2012 | Rafiee |
| 2012/0136436 A1 | 5/2012 | Cabiri et al. |
| 2012/0165930 A1 | 6/2012 | Gifford et al. |
| 2012/0197388 A1 | 8/2012 | Khairkhahan et al. |
| 2012/0203336 A1 | 8/2012 | Annest |
| 2012/0283757 A1 | 11/2012 | Miller et al. |
| 2012/0323316 A1 | 12/2012 | Chau et al. |
| 2012/0330410 A1 | 12/2012 | Hammer et al. |
| 2012/0330411 A1 | 12/2012 | Gross et al. |
| 2013/0023985 A1 | 1/2013 | Khairkhahan et al. |
| 2013/0096672 A1 | 4/2013 | Reich et al. |
| 2013/0116776 A1 | 5/2013 | Gross et al. |
| 2013/0116780 A1 | 5/2013 | Miller et al. |
| 2013/0131792 A1 | 5/2013 | Miller et al. |
| 2013/0190861 A1 | 7/2013 | Chau et al. |
| 2013/0190866 A1 | 7/2013 | Zipory et al. |
| 2013/0238024 A1 | 9/2013 | Taylor et al. |
| 2013/0282028 A1 | 10/2013 | Conklin et al. |
| 2013/0338763 A1 | 12/2013 | Rowe et al. |
| 2014/0018906 A1 | 1/2014 | Rafiee |
| 2014/0025163 A1 | 1/2014 | Padala et al. |
| 2014/0039615 A1 | 2/2014 | Padala et al. |
| 2014/0067048 A1 | 3/2014 | Chau |
| 2014/0094903 A1 | 4/2014 | Miller et al. |
| 2014/0128965 A1 | 5/2014 | Rafiee |
| 2014/0142695 A1 | 5/2014 | Gross et al. |
| 2014/0148898 A1 | 5/2014 | Gross et al. |
| 2014/0222137 A1 | 8/2014 | Miller et al. |
| 2014/0243963 A1 | 8/2014 | Sheps et al. |
| 2014/0276648 A1 | 9/2014 | Hammer et al. |
| 2014/0277088 A1 | 9/2014 | Friedman |
| 2014/0309661 A1 | 10/2014 | Sheps et al. |
| 2014/0343668 A1 | 11/2014 | Zipory et al. |
| 2014/0358223 A1 | 12/2014 | Rafiee et al. |
| 2014/0379075 A1 | 12/2014 | Maurer et al. |
| 2015/0012087 A1 | 1/2015 | Miller et al. |
| 2015/0039083 A1 | 2/2015 | Rafiee et al. |
| 2015/0081014 A1 | 3/2015 | Gross et al. |
| 2015/0100116 A1 | 4/2015 | Mohl et al. |
| 2015/0105855 A1 | 4/2015 | Cabiri et al. |
| 2015/0112429 A1 | 4/2015 | Khairkhahan et al. |
| 2015/0112432 A1 | 4/2015 | Reich et al. |
| 2015/0119981 A1 | 4/2015 | Khairkhahan et al. |
| 2015/0164637 A1 | 6/2015 | Khairkhahan et al. |
| 2015/0182336 A1 | 7/2015 | Zipory et al. |
| 2015/0202043 A1 | 7/2015 | Zakai et al. |
| 2015/0230924 A1 | 8/2015 | Miller et al. |
| 2015/0257877 A1 | 9/2015 | Hernandez |
| 2015/0272586 A1 | 10/2015 | Herman et al. |
| 2015/0272734 A1 | 10/2015 | Sheps et al. |
| 2015/0297212 A1 | 10/2015 | Reich et al. |
| 2015/0366556 A1 | 12/2015 | Khairkhahan et al. |
| 2015/0366666 A1 | 12/2015 | Khairkhahan et al. |
| 2016/0008132 A1 | 1/2016 | Cabiri et al. |
| 2016/0030176 A1 | 2/2016 | Mohl et al. |
| 2016/0058557 A1 | 3/2016 | Reich et al. |
| 2016/0074164 A1 | 3/2016 | Naor |
| 2016/0089233 A1 | 3/2016 | Lee et al. |
| 2016/0106437 A1 | 4/2016 | van der Burg et al. |
| 2016/0113767 A1 | 4/2016 | Miller et al. |
| 2016/0157862 A1 | 6/2016 | Hernandez et al. |
| 2016/0158008 A1 | 6/2016 | Miller et al. |
| 2016/0262755 A1 | 9/2016 | Zipory et al. |
| 2016/0324639 A1 | 11/2016 | Nguyen et al. |
| 2016/0331523 A1 | 11/2016 | Chau et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0100249 A1 | 4/2017 | Miller et al. |
| 2017/0105839 A1 | 4/2017 | Subramanian et al. |
| 2017/0135815 A1 | 5/2017 | Gross et al. |
| 2017/0135816 A1 | 5/2017 | Lashinski et al. |
| 2017/0189186 A1 | 7/2017 | Mohl |
| 2017/0196691 A1 | 7/2017 | Zipory et al. |
| 2017/0209270 A1 | 7/2017 | Miller et al. |
| 2017/0245993 A1 | 8/2017 | Gross et al. |
| 2017/0245994 A1 | 8/2017 | Khairkhahan et al. |
| 2017/0258588 A1 | 9/2017 | Zipory et al. |
| 2017/0258590 A1 | 9/2017 | Khairkhahan et al. |
| 2017/0265995 A1 | 9/2017 | Khairkhahan et al. |
| 2017/0296340 A1 | 10/2017 | Gross et al. |
| 2017/0325958 A1 | 11/2017 | Reich et al. |
| 2017/0325959 A1 | 11/2017 | Sheps et al. |
| 2017/0354500 A1 | 12/2017 | Martinez et al. |
| 2017/0367825 A1 | 12/2017 | Cabiri et al. |
| 2018/0008409 A1 | 1/2018 | Kutzik et al. |
| 2018/0014933 A1 | 1/2018 | Miller et al. |
| 2018/0014934 A1 | 1/2018 | Miller et al. |
| 2018/0049875 A1 | 2/2018 | Iflah et al. |
| 2018/0116797 A9 | 5/2018 | Miller et al. |
| 2018/0125657 A1 | 5/2018 | Dahlgren et al. |
| 2018/0228608 A1 | 8/2018 | Sheps et al. |
| 2018/0250133 A1 | 9/2018 | Reich et al. |
| 2018/0256318 A1 | 9/2018 | Khairkhahan |
| 2018/0256333 A1 | 9/2018 | Cabiri et al. |
| 2018/0256334 A1 | 9/2018 | Sheps et al. |
| 2018/0263776 A1 | 9/2018 | Gross et al. |
| 2018/0263777 A1 | 9/2018 | Gross et al. |
| 2018/0318080 A1 | 11/2018 | Quill et al. |
| 2019/0008641 A1 | 1/2019 | Dahlgren et al. |
| 2019/0046318 A1 | 2/2019 | Miller et al. |
| 2019/0070004 A1 | 3/2019 | Ifah et al. |
| 2019/0076247 A1 | 3/2019 | Zeng |
| 2019/0076249 A1 | 3/2019 | Khairkhahan |
| 2019/0125325 A1 | 5/2019 | Sheps et al. |

(56) References Cited

U.S. PATENT DOCUMENTS

| | | |
|---|---|---|
| 2019/0133586 A1 | 5/2019 | Zipory et al. |
| 2019/0151090 A1 | 5/2019 | Gross et al. |
| 2019/0151093 A1 | 5/2019 | Keidar et al. |
| 2019/0159898 A1 | 5/2019 | Kutzik et al. |
| 2019/0167425 A1 | 6/2019 | Reich et al. |
| 2019/0175344 A1 | 6/2019 | Khairkhahan |
| 2019/0201191 A1 | 7/2019 | McLean et al. |
| 2019/0216600 A1 | 7/2019 | Zipory et al. |
| 2019/0254821 A1 | 8/2019 | Rafiee et al. |
| 2019/0269512 A9 | 9/2019 | Lashinski |
| 2019/0269513 A9 | 9/2019 | Cabiri et al. |
| 2019/0274830 A1 | 9/2019 | Miller et al. |
| 2019/0282358 A1 | 9/2019 | Khairkhahan et al. |
| 2019/0282364 A1 | 9/2019 | Khairkhahan et al. |
| 2019/0298332 A1 | 10/2019 | Khairkhahan et al. |
| 2019/0321049 A1 | 10/2019 | Herman et al. |
| 2019/0336288 A1 | 11/2019 | Gross et al. |
| 2019/0336289 A1 | 11/2019 | Miller et al. |
| 2019/0350703 A1 | 11/2019 | Weber et al. |
| 2019/0350705 A1 | 11/2019 | Schewel et al. |
| 2019/0374343 A1 | 12/2019 | Lashinski et al. |
| 2019/0374750 A1 | 12/2019 | Hammer et al. |
| 2019/0380834 A1 | 12/2019 | Rafiee |
| 2020/0015971 A1 | 1/2020 | Brauon et al. |
| 2020/0030097 A1 | 1/2020 | Khairkhahan et al. |
| 2020/0038186 A1 | 2/2020 | Gross et al. |
| 2020/0100899 A1 | 4/2020 | Miller et al. |
| 2020/0113685 A1 | 4/2020 | Miller et al. |
| 2020/0205966 A1 | 7/2020 | Khairkhahan et al. |
| 2020/0205975 A1 | 7/2020 | Khairkhahan |
| 2020/0205980 A1 | 7/2020 | Khairkhahan et al. |
| 2020/0214841 A1 | 7/2020 | Khairkhahan et al. |
| 2020/0222185 A1 | 7/2020 | Kappetein et al. |
| 2020/0275974 A1 | 9/2020 | Gifford et al. |
| 2020/0289265 A1 | 9/2020 | Gifford et al. |
| 2020/0330229 A1 | 10/2020 | Serraf et al. |
| 2020/0337843 A1 | 10/2020 | Khairkhahan et al. |
| 2020/0383776 A1 | 12/2020 | Schewel |
| 2020/0397567 A1 | 12/2020 | Khairkhahan et al. |
| 2021/0085462 A1 | 3/2021 | Gifford et al. |
| 2021/0196462 A1 | 7/2021 | Khairkhahan |
| 2021/0298901 A1 | 9/2021 | Khairkhahan et al. |
| 2022/0000621 A1 | 1/2022 | Gifford et al. |
| 2022/0039944 A1 | 2/2022 | Khairkhahan |
| 2022/0039951 A1 | 2/2022 | Khairkhahan |
| 2022/0054269 A1 | 2/2022 | Khairkhahan |

FOREIGN PATENT DOCUMENTS

| | | |
|---|---|---|
| CN | 101056596 | 10/2007 |
| CN | 101068508 | 11/2007 |
| CN | 101947146 | 1/2011 |
| CN | 102065777 | 5/2011 |
| CN | 102458309 | 5/2012 |
| CN | 202821715 | 3/2013 |
| CN | 103338726 | 10/2013 |
| CN | 102905648 | 1/2015 |
| CN | 104394803 | 3/2015 |
| CN | 104582637 | 4/2015 |
| CN | 105451688 | 3/2016 |
| EP | 1 294 310 | 3/2003 |
| EP | 1 959 865 | 8/2008 |
| EP | 2 410 948 | 2/2012 |
| EP | 1 796 597 | 1/2013 |
| EP | 2 661 239 | 11/2013 |
| EP | 2 667 824 | 12/2013 |
| EP | 2 995 279 | 3/2016 |
| JP | S54-088693 | 7/1979 |
| JP | 2005-535384 | 11/2005 |
| JP | 2007-518492 | 7/2007 |
| JP | 2008-517672 | 5/2008 |
| JP | 2010-511469 | 4/2010 |
| JP | 2012-511402 | 5/2012 |
| JP | 2012-520716 | 9/2012 |
| JP | 2014-510563 | 5/2014 |
| JP | 2014-231015 | 12/2014 |
| JP | 2015-523898 | 8/2016 |
| JP | 2016-533798 | 11/2016 |
| JP | 2017-18675 | 1/2017 |
| WO | WO 97/007744 | 3/1997 |
| WO | WO 99/53869 | 10/1998 |
| WO | WO 2004/014258 | 2/2004 |
| WO | WO 2005/069875 | 8/2005 |
| WO | WO 2006/032051 | 3/2006 |
| WO | WO 2006/041877 | 4/2006 |
| WO | WO 2006/086434 | 8/2006 |
| WO | WO 2007/062054 | 5/2007 |
| WO | WO 2007/135101 | 11/2007 |
| WO | WO 2007/140470 | 12/2007 |
| WO | WO 2008/068756 | 6/2008 |
| WO | WO 2008/141322 | 11/2008 |
| WO | WO 2010/106438 | 9/2010 |
| WO | WO 2011/037891 | 3/2011 |
| WO | WO 2011/047168 | 4/2011 |
| WO | WO 2012/061809 | 5/2012 |
| WO | WO 2012/092437 | 7/2012 |
| WO | WO 2012/102928 | 8/2012 |
| WO | WO 2013/131069 | 9/2013 |
| WO | WO 2013/173587 | 11/2013 |
| WO | WO 2013/178335 | 12/2013 |
| WO | WO 2013/192107 | 12/2013 |
| WO | WO 2014/181336 | 11/2014 |
| WO | WO 2014/207575 | 12/2014 |
| WO | WO 2015/020971 | 2/2015 |
| WO | WO 2015/052570 | 4/2015 |
| WO | WO 2015/061533 | 4/2015 |
| WO | WO 2015/195823 | 12/2015 |
| WO | WO 2015/200497 | 12/2015 |
| WO | WO 2016/178136 | 11/2016 |
| WO | WO 2016/183485 | 11/2016 |
| WO | WO 2017/079279 | 5/2017 |
| WO | WO 2017/136596 | 8/2017 |
| WO | WO 2019/116322 | 6/2019 |
| WO | WO 2019/222694 | 11/2019 |
| WO | WO 2019/241777 | 12/2019 |

OTHER PUBLICATIONS

Biocina, The arteficial coaptation surface concept in mitral valve repair, University of Zagreb School of Medicine, Department of Cardiac Surgery, Savudrija Mitrofast 2010.

Chiam et al., Percutaneous Transcatheter Mitral Valve Repair, The American College of Cardiology Foundation, JACC: Cardiovascular Interventions, vol. 4 No. 1, Jan. 2011:1-13.

Jassar et al., Posterior Leaflet Augmentation in Ischemic Mitral Regurgitation Increases Leaflet Coaptation and Mobility, The Society of Thoracic Surgeons, Ann Thorac Surg 2012; 94:1438-45.

Langer et al., Posterior mitral leaflet extension: An adjunctive repair option for ischemic mitral regurgitation?, Surgery for Acquired Cardiovascular Disease, The Journal of Thoracic and Cardiovascular Surgery, Apr. 2006, downloaded Jun. 18, 2011.

Mohl et al., The Angel Valve Concept, Vienna University of Technology, Medical University of Vienna, Technology Offer, 1 page.

Mohl et al., An Innovative Concept For Transcatheter Treatment of Annular Dilatation and Restrictive Leaflet Motion in Mitral Insufficiency, Medical University of Vienna, 1 page.

Piemonte et al., Cardiovascular™: The Mitral Valve Spacer, Presented at Transcatheter Cardiovascular Therapeutics Conference—TCT Conference, Oct. 2008.

Rumel et al., The Correction of Mitral Insufficiency with a Trans-Valvular Polyvinyl Formalinized Plastic (Ivalon) Sponge Prosthesis: A Preliminary Report, American College of Chest Physicians, 1958;33;401-413, Dec. 2, 2010.

International Preliminary Report on Patentability for PCT/US2012/021744 dated Aug. 8, 2013 in 15 pages.

International Search Report for Application No. PCT/US2013/046173 dated Oct. 4, 2013 in 15 pages.

International Search Report for Application No. PCT/US2014/061901 dated Jan. 26, 2015 in 14 pages.

(56) References Cited

OTHER PUBLICATIONS

International Search Report for Application No. PCT/US2015/036260 dated Oct. 1, 2015 in 20 pages.
International Search Report for Application No. PCT/US2015/037451 dated Oct. 6, 2015 in 12 pages.
International Search Report for Application No. PCT/US2016/060094 dated Feb. 9, 2017 in 8 pages.
International Search Report for Application No. PCT/US2018/022043 dated Jun. 25, 2018 in 13 pages.
Extended European Search Report, EP 12738989.8, dated May 24, 2016.
Office Action for EP 12738989.8 dated Mar. 3, 2017.
Office Action for EP 12738989.8 dated Sep. 19, 2017.
Extended European Search Report, EP 13806272.4, dated Nov. 11, 2015.
Extended European Search Report, EP 14856738.1, dated Jun. 7, 2017.
Extended European Search Report, EP 15809346.8, dated Feb. 13, 2018.
Extended European Search Report, EP 15812032.9, dated Oct. 18, 2017.
Extended European Search Report, EP 16862864.2, dated May 10, 2019.
Office Action for CA 2,825,520 dated Nov. 27, 2017.
Office Action for CA 2,825,520 dated Aug. 21, 2018.
Office Action for CA 2,877,344 dated Mar. 12, 2019.
Office Action for CA 2,877,344 dated Oct. 9, 2019.
Office Action for CA 2,877,344 dated Jul. 21, 2020.
Office Action for CN 201280006673.7 dated Dec. 10, 2014.
Office Action for CN 201280006673.7 dated Sep. 22, 2015.
Office Action for CN 201280006673.7 dated Feb. 1, 2016.
Office Action for CN 201380044122.4 dated Nov. 4, 2015.
Office Action for CN 201380044122.4 dated Aug. 24, 2016.
Office Action for CN 201480070933.6 dated May 10, 2017.
Office Action for CN 201480070933.6 dated Dec. 25, 2017.
Office Action for CN 201480070933.6 dated Aug. 10, 2018.
Office Action forCN 201480070933.6 dated Apr. 17, 2019.
Office Action for CN 201580044329.0 dated Jan. 17, 2018.
Office Action for CN 201580044329.0 dated Jul. 29, 2019.
Office Action for CN 201580045375.2 dated Mar. 29, 2018.
Office Action for CN 201580045375.2 dated Nov. 12, 2018.
Office Action for CN 201680077877.8 dated Aug. 15, 2019.
Office Action for EP 15812032.9, dated Oct. 10, 2019.
Office Action for JP 2013-552015 dated Dec. 7, 2015.
Office Action for JP 2013-552015 dated Oct. 7, 2016.
Office Action for JP 2013-552015 dated Jun. 5, 2017.
Office Action for JP 2015-518499 dated Feb. 27, 2017.
Office Action for JP 2015-518499 dated Aug. 31, 2017.
Office Action for JP 2015-518499 dated Aug. 20, 2018.
Office Action for JP 2016-525999 dated Jul. 9, 2018.
Office Action for JP 2016-525999 dated Jun. 27, 2019.
Office Action for JP 2016-525999 dated Mar. 16, 2020.
Office Action for 2016-573983 dated Apr. 1, 2019.
Office Action for 2016-573983 dated Nov. 11, 2019.
Office Action for JP 2016-574967 dated May 7, 2019.
Office Action for JP 2016-574967 dated Dec. 26, 2019.
International Search Report for Application No. PCT/US2019/050331 dated Jan. 23, 2020 in 9 pages.
Office Action for CN 201580044329.0 dated Mar. 3, 2020.
Office Action for 2016-573983 dated May 11, 2020.
Office Action for CN 201580044329.0 dated Aug. 26, 2020.
Office Action for EP 15812032.9, dated Jul. 6, 2020.
Office Action for JP 2016-574967 dated Jun. 29, 2020.
Office Action for JP 2018-543021 dated Oct. 27, 2020.
Office Action for CA 2,877,344 dated Dec. 23, 2020.
Office Action for CA 2,934,182 dated Dec. 9, 2020.
Office Action for JP 2020-082001 dated Mar. 29, 2021.
Extended European Search Report, EP 18768736.3, dated Oct. 9, 2020.
International Search Report for Application No. PCT/US2020/065261 dated Apr. 13, 2021 in 13 pages.
Office Action for CN 201880031519.2 dated May 19, 2021.
Office Action for EP 13806272.4, dated Mar. 23, 2021.
Office Action for EP 14856738.1, dated Apr. 23, 2021.
Office Action for JP 2020-085273 dated May 31, 2021.
Office Action for CA 2,934,182 dated Jun. 30, 2021.
Office Action for CA 2,958,065 dated Jul. 9, 2021.
Office Action for JP 2018-543021 dated Oct. 4, 2021.
Office Action for JP 2020-085273 dated Aug. 23, 2021.
Office Action for JP 2020-082001 dated Nov. 29, 2021.
Office Action for CA 2,934,182 dated Mar. 2, 2022.
Office Action for CA 2,958,065 dated Mar. 2, 2022.
Office Action for 2020-041944 dated Feb. 21, 2022.
Office Action for 2019-572351 dated Feb. 28, 2022.

* cited by examiner

Mal-coaptation of the Mitral Valve Leaflets
Causing Mitral Valve Regurgitation in Systole Coaptation Assistant Device Positioned in between
the Mitral Valve Leaflets to Eliminate Regurgitation

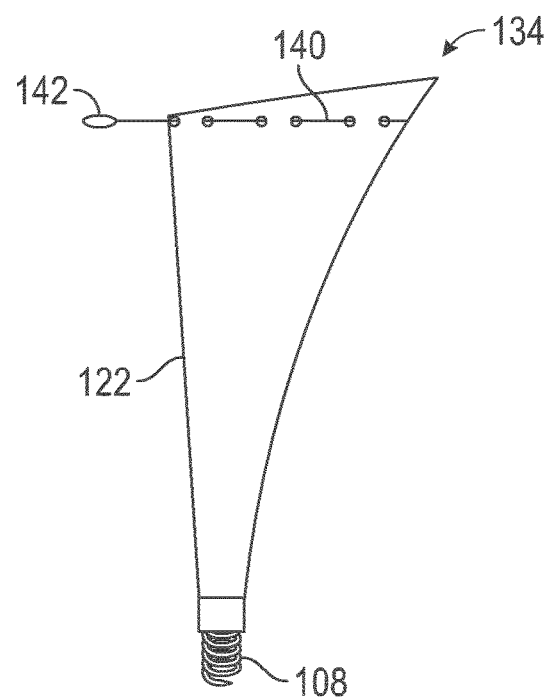
FIG. 3F
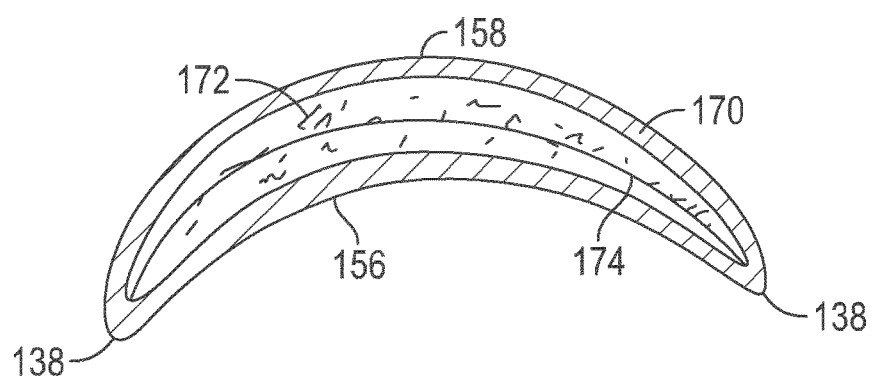
FIG. 3G1
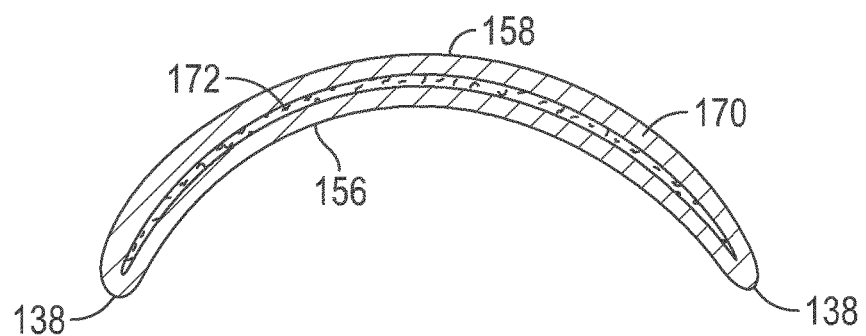
FIG. 3G2

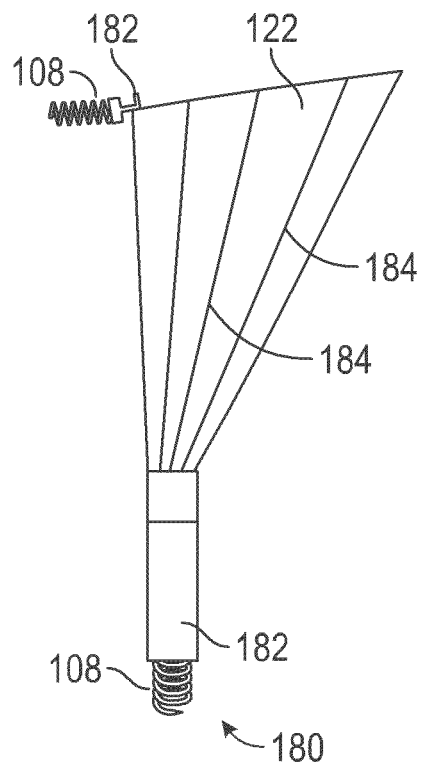
FIG. 3H
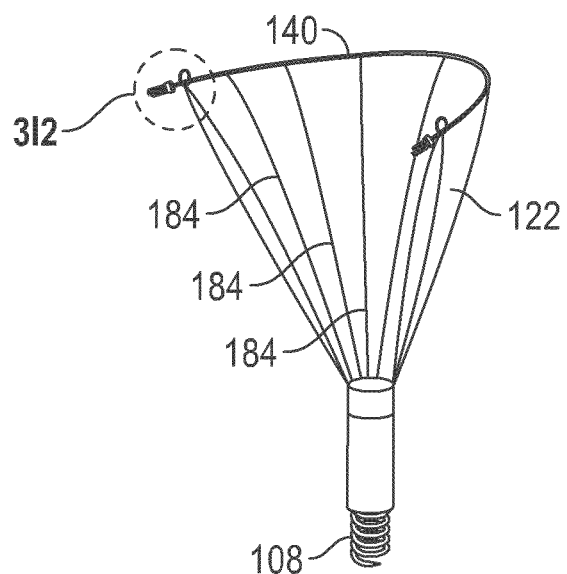
FIG. 3I1
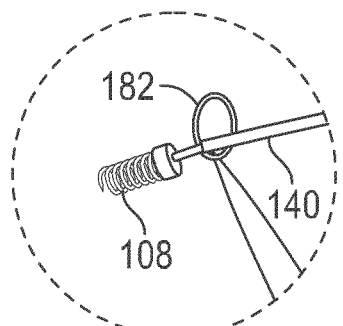
FIG. 3I2

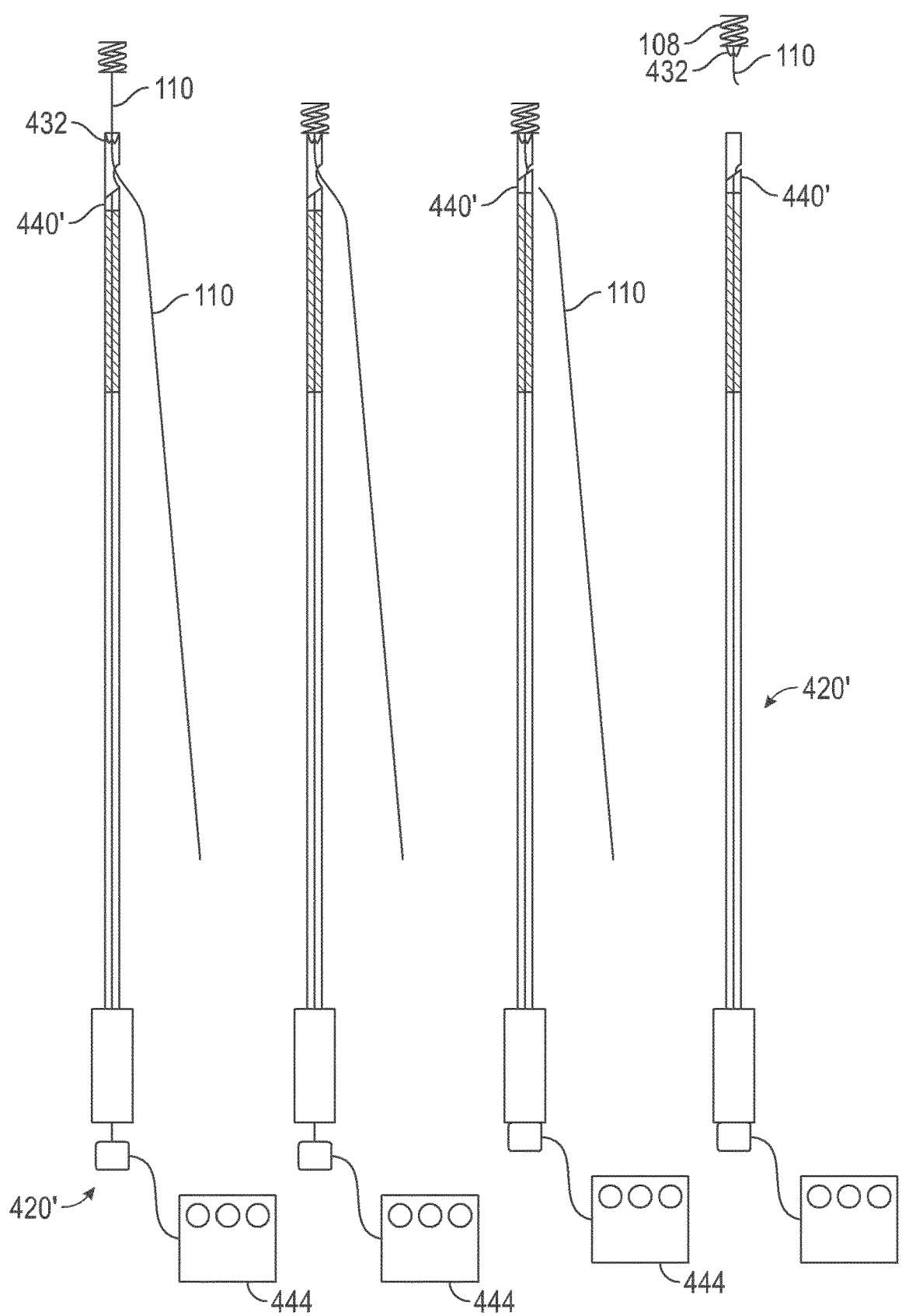

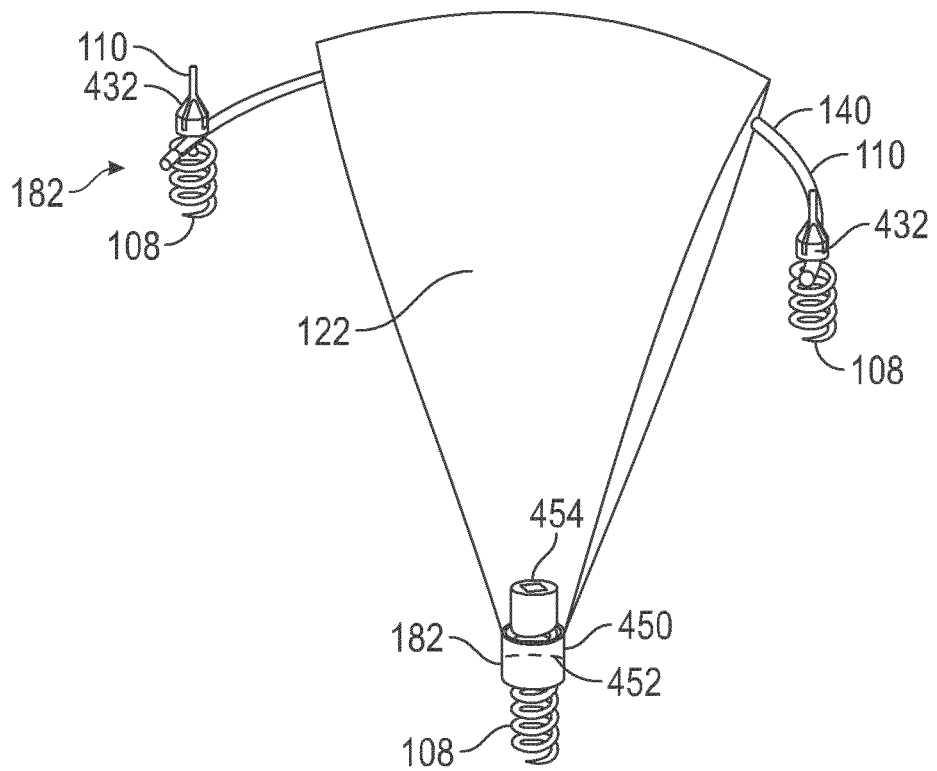
FIG. 3I14
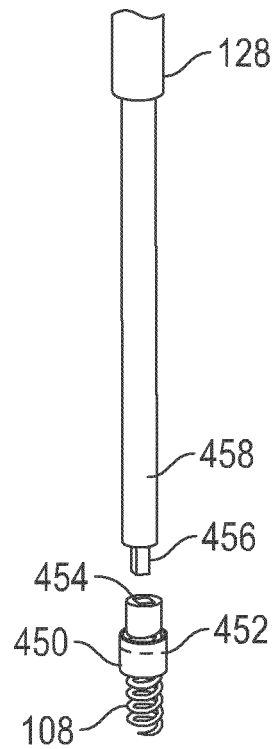
FIG. 3I15

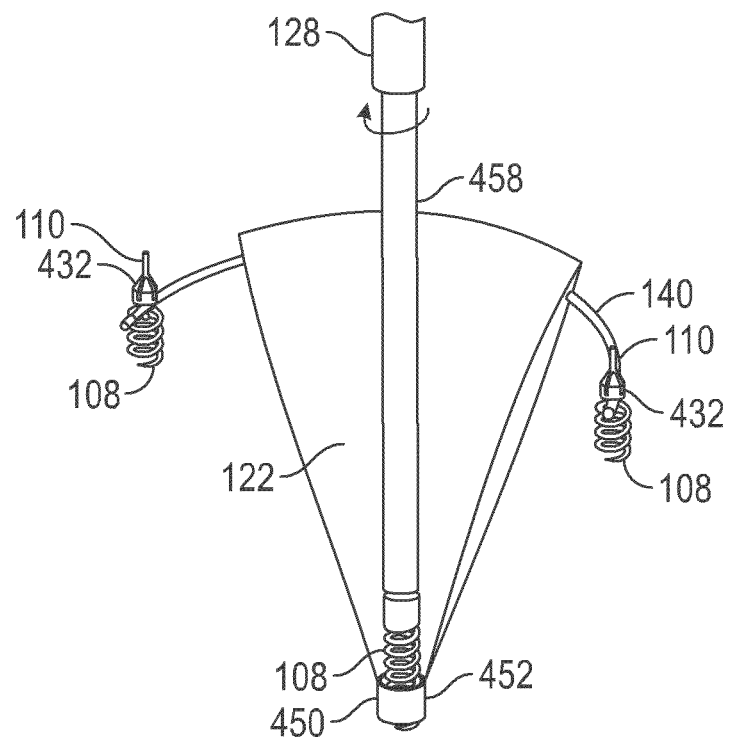
FIG. 3I16
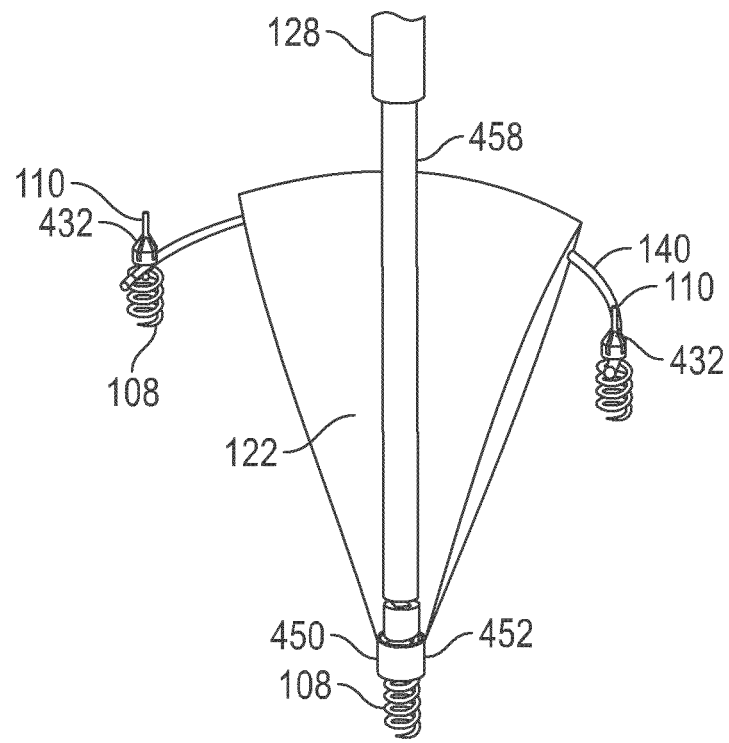
FIG. 3I17

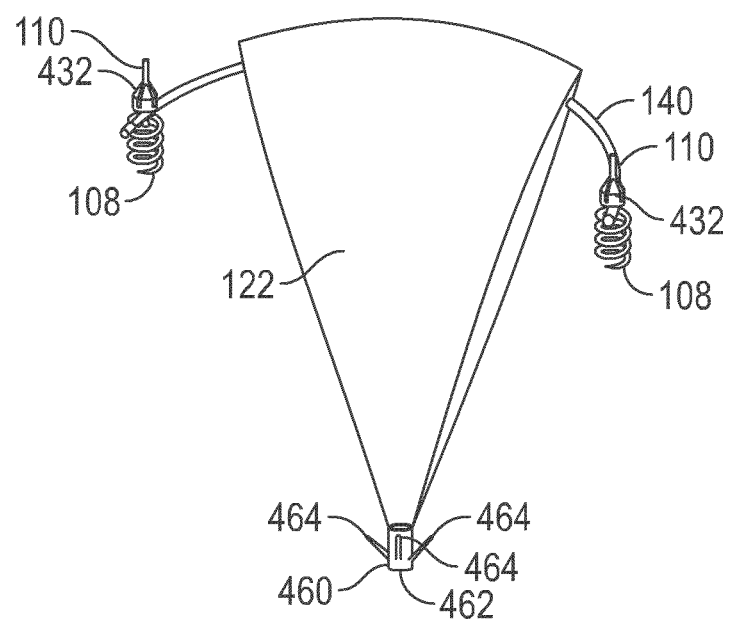
FIG. 3I18

COAPTATION ENHANCEMENT IMPLANT, SYSTEM, AND METHOD

This application is a continuation of U.S. patent application Ser. No. 16/675,565, filed Nov. 6, 2019, which in turn is a continuation of U.S. patent application Ser. No. 15/475,629, filed Mar. 31, 2017, now U.S. Pat. No. 10,470,883, which in turn is a continuation of U.S. patent application Ser. No. 14/500,470, filed Sep. 29, 2014, now U.S. Pat. No. 9,610,163, which in turn is a continuation of U.S. patent application Ser. No. 13/099,532, filed May 3, 2011, now U.S. Pat. No. 8,845,717, which in turn claims priority to provisional U.S. Patent Application No. 61/437,397, titled "Coaptation Enhancement Implant, System, and Method" and filed Jan. 28, 2011. The entire disclosure of each of the foregoing priority applications is hereby incorporated by reference herein for all purposes.

BACKGROUND OF THE INVENTION

The present invention generally provides improved medical devices, systems, and methods, typically for treatment of heart valve disease and/or for altering characteristics of one or more valves of the body. Exemplary embodiments of the invention include implants for treatment of mitral valve regurgitation.

The human heart receives blood from the organs and tissues via the veins, pumps that blood through the lungs where the it becomes enriched with oxygen, and propels the oxygenated blood out of the heart to the arteries so that the organ systems of the body can extract the oxygen for proper function. Deoxygenated blood flows back to the heart where it is once again pumped to the lungs.

As can generally be seen in FIGS. 1A and 1B, the heart includes four chambers: the right atrium (RA), the right ventricle (RV), the left atrium (LA) and the left ventricle (LV). The pumping action of the left and right sides of the heart occurs generally in synchrony during the overall cardiac cycle.

The heart has four valves generally configured to selectively transmit blood flow in the correct direction during the cardiac cycle. The valves that separate the atria from the ventricles are referred to as the atrioventricular (or AV) valves. The AV valve between the left atrium and the left ventricle is the mitral valve. The AV valve between the right atrium and the right ventricle is the tricuspid valve. The pulmonary valve directs blood flow to the pulmonary artery and thence to the lungs; blood returns to the left atrium via the pulmonary veins. The aortic valve directs flow through the aorta and thence to the periphery. There are normally no direct connections between the ventricles or between the atria.

The mechanical heartbeat is triggered by an electrical impulse which spreads throughout the cardiac tissue. Opening and closing of heart valves may occur primarily as a result of pressure differences between chambers, those pressures resulting from either passive filling or chamber contraction. For example, the opening and closing of the mitral valve may occur as a result of the pressure differences between the left atrium and the left ventricle.

At the beginning of ventricular filling (diastole) the aortic and pulmonary valves are closed to prevent back flow from the arteries into the ventricles. Shortly thereafter, the AV valves open to allow unimpeded flow from the atria into the corresponding ventricles. Shortly after ventricular systole (i.e., ventricular emptying) begins, the tricuspid and mitral valves normally shut, forming a seal which prevents flow from the ventricles back into the corresponding atria.

Unfortunately, the AV valves may become damaged or may otherwise fail to function properly, resulting in improper closing. The AV valves are complex structures that generally include an annulus, leaflets, chordae and a support structure. Each atrium interfaces with its valve via an atrial vestibule. The mitral valve has two leaflets; the analogous structure of the tricuspid valve has three leaflets, and apposition or engagement of corresponding surfaces of leaflets against each other helps provide closure or sealing of the valve to prevent blood flowing in the wrong direction. Failure of the leaflets to seal during ventricular systole is known as malcoaptation, and may allow blood to flow backward through the valve (regurgitation). Heart valve regurgitation can have serious consequences to a patient, often resulting in cardiac failure, decreased blood flow, lower blood pressure, and/or a diminished flow of oxygen to the tissues of the body. Mitral regurgitation can also cause blood to flow back from the left atrium to the pulmonary veins, causing congestion. Severe valvular regurgitation, if untreated, can result in permanent disability or death.

A variety of therapies have been applied for treatment of mitral valve regurgitation, and still other therapies may have been proposed but not yet actually used to treat patients. While several of the known therapies have been found to provide benefits for at least some patients, still further options would be desirable. For example, pharmacologic agents (such as diuretics and vasodilators) can be used with patients having mild mitral valve regurgitation to help reduce the amount of blood flowing back into the left atrium. However, medications can suffer from lack of patient compliance. A significant number of patients may occasionally (or even regularly) fail to take medications, despite the potential seriousness of chronic and/or progressively deteriorating mitral valve regurgitation. Pharmacological therapies of mitral valve regurgitation may also be inconvenient, are often ineffective (especially as the condition worsens), and can be associated with significant side effects (such as low blood pressure).

A variety of surgical options have also been proposed and/or employed for treatment of mitral valve regurgitation. For example, open-heart surgery can replace or repair a dysfunctional mitral valve. In annuloplasty ring repair, the posterior mitral annulus can be reduced in size along its circumference, optionally using sutures passed through a mechanical surgical annuloplasty sewing ring to provide coaptation. Open surgery might also seek to reshape the leaflets and/or otherwise modify the support structure. Regardless, open mitral valve surgery is generally a very invasive treatment carried out with the patient under general anesthesia while on a heart-lung machine and with the chest cut open. Complications can be common, and in light of the morbidity (and potentially mortality) of open-heart surgery, the timing becomes a challenge-sicker patients may be in greater need of the surgery, but less able to withstand the surgery. Successful open mitral valve surgical outcomes can also be quite dependent on surgical skill and experience.

Given the morbidity and mortality of open-heart surgery, innovators have sought less invasive surgical therapies. Procedures that are done with robots or through endoscopes are often still quite invasive, and can also be time consuming, expensive, and in at least some cases, quite dependent on the surgeon's skill. Imposing even less trauma on these sometimes frail patients would be desirable, as would be providing therapies that could be successfully implemented by a significant number of physicians using widely distributed skills. Toward that end, a number of purportedly less invasive technologies and approaches have been proposed. These include devices which seek to re-shape the mitral annulus from within the coronary sinus; devices that attempt to reshape the annulus by cinching either above to below the native annulus; devices to fuse the leaflets (imitating the Alfieri stitch); devices to re-shape the left ventricle, and the like. Perhaps most widely known, a variety of mitral valve replacement implants have been developed, with these implants generally replacing (or displacing) the native leaflets and relying on surgically implanted structures to control the blood flow paths between the chambers of the heart. While these various approaches and tools have met with differing levels of acceptance, none has yet gained widespread recognition as an ideal therapy for most or all patients suffering from mitral valve regurgitation.

Because of the challenges and disadvantages of known minimally invasive mitral valve regurgitation therapies and implants, still further alternative treatments have been proposed. Some of the alternative proposals have called for an implanted structure to remain within the valve annulus throughout the heart beat cycle. One group of these proposals includes a cylindrical balloon or the like to remain implanted on a tether or rigid rod extending between the atrium and the ventricle through the valve opening. Another group relies on an arcuate ring structure or the like, often in combination with a buttress or structural cross-member extending across the valve so as to anchor the implant. Unfortunately, sealing between the native leaflets and the full perimeter of a balloon or other coaxial body may prove challenging, while the significant contraction around the native valve annulus during each heart beat may result in significant fatigue failure issues during long-term implantation if a buttress or anchor interconnecting cross member is allowed to flex. Moreover, the significant movement of the tissues of the valve may make accurate positioning of the implant challenging regardless of whether the implant is rigid or flexible.

In light of the above, it would be desirable to provide improved medical devices, systems, and methods. It would be particularly desirable to provide new techniques for treatment of mitral valve regurgitation and other heart valve diseases, and/or for altering characteristics of one or more of the other valves of the body. The need remains for a device which can directly enhance leaflet coaptation (rather than indirectly via annular or ventricular re-shaping) and which does not disrupt leaflet anatomy via fusion or otherwise, but which can be deployed simply and reliably, and without excessive cost or surgical time. It would be particularly beneficial if these new techniques could be implemented using a less-invasive approach, without stopping the heart or relying on a heart-lung machine for deployment, and without relying on exceptional skills of the surgeon to provide improved valve and/or heart function.

SUMMARY OF THE INVENTION

The present invention generally provides improved medical devices, systems, and methods. In exemplary embodiments, the invention provides new implants, implant systems, and methods for treatment of mitral valve regurgitation and other valve diseases. The implants will generally include a coaptation assist body which remains within the blood flow path as the leaflets of the valve move back and forth between an open-valve configuration and a closed valve configuration. The exemplary coaptation assist bodies or valve bodies may be relatively thin, elongate (along the blood flow path), and/or conformable structures which extend laterally across some, most, or all of the width of the valve opening, allowing the native leaflets to engage and seal against the opposed surfaces on either side of the valve body. To allow safe and effective, long-term operation of the valve tissue, the valve body may be laterally offset from the centroid of the overall valve, and/or may curve laterally across the valve opening so as to mimic the natural, pre-treatment geometry of the coaptation zone directly between the two native mitral valve leaflets. The presence of the valve body between the native leaflets can enhance sealing by filling gaps between the mal-coapting leaflet surfaces, and/or the implanted valve body can allow the leaflets to coapt with axially offset regions of the opposed coaptation surfaces of the valve body.

Though the valve body will generally remain within the blood flow path of the valve (typically with blood passing on either side of the valve body during diastole), the valve body may move and/or deform significantly to help maintain natural movement of the heart tissues. As the valve opens during diastole, the valve body may move somewhat with the flow, somewhat like a middle leaflet or sail around which the blood passes, as well as with movement of the heart tissues to which the valve body is mounted. As the valve moves from the open configuration toward the closed configuration, the movement of the native valve leaflet tissue, valve-body support tissues (to which the valve body is anchored), and blood within the heart may help to move the valve body back into a desirable configuration for sealing. Surprisingly, separate deployment of independent anchors near each of the two commissures may greatly facilitate and expedite accurate positioning and support of the valve body, with an exemplary triangular valve body employing a third anchor between the papillary muscles (or otherwise within the ventricle). The exemplary valve body includes an outer surface comprising ePTFE or other biocompatible and non-thrombogenic materials, ideally formed as a layer over a fluid absorbing foam or other matrix that swells toward a desired nominal three-dimensional valve body shape after introduction into the heart, with the valve body shape optionally being selected after one or more of the anchors has been deployed. Advantageously, the implants described herein can be placed into a patient's beating heart and accurately positioned in alignment with the mitral valve without open heart surgery, typically via a patient's vasculature and/or using minimally invasive surgical techniques, and often using a catheter deployment system having a desirably small profile. Hence, the invention can provide simple, cost-effective, and less invasive devices, systems, and methods for treating a range of dysfunction of a heart valve, e.g., in the treatment of organic and functional mitral valve regurgitation.

In a first aspect, the invention provides a method for treating mal-coaptation of a heart valve in a patient. The heart valve has an annulus and first and second leaflets. The annulus defines a valve axis extending along a blood flow path, and the first and second leaflets have a coaptation zone defining a curve extending across the flow path. The method comprises introducing an implant into the heart while the implant is in a first configuration. The implant is deployed from the first configuration to a second configuration within the heart. The implant in the second configuration has a coaptation assist body with first and second opposed coaptation surfaces. The deployed implant is supported so that the coaptation assist body is offset from the axis of the heart valve along the coaptation zone. The first leaflet of the heart valve seals or coapts with the first coaptation surface and the second leaflet of the heart valve seals or coapts with the second coaptation surface such that the mal-coaptation of the heart valve is mitigated.

In another aspect, the invention provides a method for treating mal-coaptation of a heart valve in a patient. The heart valve has first and second leaflets with a first commissure at a first junction of the first and second leaflets and a second commissure at a second junction of the first and second leaflets. The method comprises selectively deploying a first anchor at a first target location near the first commissure. A second anchor is selectively deployed at a second target location near the second commissure. A coaptation assist body is introduced into the heart, the coaptation assist body having first and second opposed coaptation surfaces. The coaptation assist body is supported with the first anchor so that a first lateral edge of the coaptation assist body extends toward the first commissure, and the coaptation assist body is supported with the second anchor so that a second lateral edge of the coaptation assist body extends toward the second commissure. The first leaflet of the heart valve coapts with the first coaptation surface and the second leaflet of the heart valve coapts with the second coaptation surface such that the mal-coaptation of the heart valve is mitigated In an apparatus aspect, the invention provides an implant for treating mal-coaptation of a heart valve in a patient. The heart valve has an annulus and first and second leaflets with a first commissure at a first junction of the first and second leaflets and a second commissure at a second junction of the first and second leaflets. The implant comprises a coaptation assist body having an axis and first and second opposed major coaptation surfaces. Each coaptation surface extends laterally between a first lateral edge and a second lateral edge of the coaptation assist body. A first anchor is selectively deployable at a first target location of the heart near the first commissure and coupleable to the coaptation assist body so that the first lateral edge is oriented toward the first commissure. A second anchor is selectively deployable, independently of the deployment of the first anchor, at a second target location of the heart near the second commissure, and is coupleable with the coaptation assist device so that the second lateral edge is oriented toward the second commissure, such that the first leaflet of the heart valve coapts with the first coaptation surface and the second leaflet of the heart valve coapts with the second coaptation surface sufficiently that the mal-coaptation of the heart valve is mitigated In another device aspect the invention provides a coaptation assist implant for treating mal-coaptation of a heart valve in a patient. The heart valve has an annulus and first and second leaflets, the annulus defining a valve axis extending along a blood flow path. The first and second leaflets have a coaptation zone defining a curve extending across the flow path. The implant comprises a coaptation assist body having an axis and first and second opposed major coaptation surfaces. Each coaptation surface extends laterally between a first lateral edge and a second lateral edge of the coaptation assist body. The coaptation assist body is supportable within the heart so that the axis of the implant extends along the axis of the valve with the first and second lateral sides of the coaptation assist body extend along the curve of the coaptation zone of the heart valve. The coaptation assist body of the supported implant is sufficiently laterally conformable that engagement between the implant and the heart laterally bends the coaptation assist body between the edges toward the curve defined by the coaptation zone of the heart valve In yet another device aspect, the invention provides a coaptation assist implant for treating mal-coaptation of a heart valve in a patient. The heart valve has an annulus and first and second leaflets, the annulus defining a valve axis extending along a blood flow path. The first and second leaflets have a coaptation zone defining a curve extending across the flow path. The implant comprises a coaptation assist body having an axis and first and second opposed major coaptation surfaces. Each coaptation surface extends laterally between a first lateral edge and a second lateral edge of the coaptation assist body. The coaptation assist body is introducible into the heart and supportable within the heart so that the axis of the coaptation assist body extends along the axis of the valve with the first and second lateral sides of the coaptation assist body extending, fully or partially, along the curve of the coaptation zone of the heart valve. The coaptation assist body is deployable from a first configuration to a second configuration by removing the coaptation assist body from within a surrounding deployment catheter.

In a system aspect, the invention provides a coaptation assist system for treating malcoaptation of a heart valve in a patient. The heart valve has an annulus and first and second leaflets. The annulus defines a valve axis extending along a blood flow path. The system comprises a deployment catheter system including a catheter body having a proximal end and a distal end. The distal end is steerable within the heart from the proximal end. A first anchor is selectively deployable from the distal end of the catheter body at a first target location of the heart near the first commissure. A coaptation assist body has an axis and first and second opposed major coaptation surfaces. Each coaptation surface extends laterally between a first lateral edge and a second lateral edge of the coaptation assist body. The coaptation assist body is introducible into the heart and coupleable in vivo with the first anchor after the first anchor is deployed in the heart so that the first lateral edge extends toward the first commissure.

In exemplary embodiments, a second anchor may be selectively deployable at a second target location, and a distal ventricular anchor may be selectively deployable at a third target locations, the selection of the target locations ideally being substantially independent of each other. Optionally, in vivo coupling of the coaptation assist body to the second anchor orients the second lateral edge toward the second commissure, while the distal ventricular anchor may optionally be mounted to the coaptation assist body prior to introduction into the patient and used to help orient the coaptation assist body. In many embodiments the coaptation assist body of the supported implant will define a curve extending across the blood flow path of the valve. The curve of the coaptation assist body can corresponding to the curve of the coaptation zone. Optionally, the engagement between the implant and the tissue of the heart may orient and maintain a position of the coaptation assist body so that the curves correspond. The implant will often be deployed and supported within the heart so that along the coaptation zone the first surface has a curved cross-section and the second surface has a curved cross-section, and so that coaptation assist body, including the curved cross-sections of the first and second surfaces, is separated from and curves around the central axis of the heart valve. The implant can be deployed and supported within the heart so that along the coaptation zone the first surface has a concave cross-section and the second surface has a convex cross-section, and so that the concave cross-section of the first surface is separated from and curves around the axis of the heart valve.

In another device aspect, a coaptation assist device for treating mal-coaptation of a heart valve in a patient is provided. The heart valve has an annulus and first and second leaflets. The annulus defines a valve axis, and the first and second leaflets have a coaptation zone. The device comprises a coaptation assist body having an axis and first and second opposed major coaptation surfaces. The coaptation assist body defines a channel within the coaptation assist body, and the coaptation assist body is introducible into the heart and coupleable in vivo within the heart valve. The device further comprises a tether disposed within the axial channel and coupled to the coaptation assist body near a first end of the channel, and also comprises a curvature lock attached to the tether near a second end of the channel. The tether is lockable by the lock to constrain the distance between the first and second ends of the channel so as to define a curvature of the coaptation assist body.

In another method aspect, a method of treating mal-coaptation of a heart valve in a patient is provided. The heart valve has an annulus and first and second leaflets. The annulus defines a valve axis extending along a blood flow path, and the first and second leaflets have a coaptation zone. The method comprises introducing an implant having a coaptation assist body with first and second opposed coaptation surfaces into the heart valve, supporting the deployed implant so that the coaptation assist body is disposed within the coaptation zone, and adjusting a curvature of the coaptation assist body.

In another system aspect, a system for treating mal-coaptation of a heart valve in a patient is provided. The heart valve has an annulus and first and second leaflets, and the annulus defines a valve axis. The system comprises a catheter system including a catheter body having a proximal end and a distal end, and the distal end is steerable within the heart from the proximal end. The system further comprises a coaptation assist body having an axis and first and second opposed major coaptation surfaces. Each of the coaptation surfaces extends laterally between a first lateral edge and a second lateral edge of the coaptation assist body. The coaptation assist body is introducible into the heart and coupleable in vivo within the heart valve, and the coaptation assist body defines a channel. The system further includes a tether extending through the channel such that a curvature of the coaptation assist body is adjustable by varying the distance between the ends of the channel along the tether. The system also comprises a curvature lock on the tether operable to constrain the distance between the ends of the channel so as to define a curvature of the coaptation assist body.

Advantageously, engagement between the implant and the heart valve (optionally including engagement between the coaptation assist body and the leaflets) can induce conformation of the curve of the coaptation assist body to the curve defined by the coaptation zone of the heart valve. More specifically, the coaptation zone of the heart valve may have a pre-treatment coaptation zone and the coaptation zone may exhibit a pre-treatment curve across the valve annulus. Engagement of the heart valve against the implant can laterally bend the coaptation assist body from a nominal cross-sectional shape toward the pre-treatment curve. Note that lateral flexibility of the coaptation assist body may be quite high (some embodiments relying on a single sheet of relatively thin membrane along at least a portion of the body, optionally with the membrane being supported at opposed edges and without lateral reinforcement against lateral bending), and that the bending forces will often be imposed at least in part via the anchoring structures (and/or via the direct engagement between the native leaflets of the valve and the coaptation assist body). Where the first leaflet may coapt with the first coaptation surface along a first axial coaptation range, and the second leaflet may coapt with the second coaptation surface along a second axial coaptation range at least partially offset from the first coaptation range, the coaptation assist body will preferably have sufficient axial stiffness to inhibit axial flexing when the first and second axial coaptation ranges are offset such that regurgitation associated with prolapse is inhibited. For example, axially oriented stiffeners may extend along an axial length of the coaptation body. In many embodiments, the axial stiffness of the coaptation assist body will be greater than a lateral stiffness of the coaptation assist body, such that engagement of the leaflets of the valve against the coaptation assist body laterally bends the coaptation assist body with limited axial bending of the coaptation assist body, optionally through the use of axial stiffeners, supporting of the coaptation assist body under an axial load, or the like.

Embodiments of the coaptation assist body and methods for its use may benefit from relatively simple and readily deployed shapes. In some embodiments, the implant can be deployed and supported within the heart so that downstream of the coaptation zone the coaptation assist body defines a downstream curve, the downstream curve having a radius smaller than the curve of the coaptation assist body along the coaptation zone this provides the coaptation assist body with a funnel-like shape. A lateral width of the coaptation assist body adjacent the annulus may be configured to extend only part way between the commissures during some or all of the heart beat cycle. As the commissure-to-commissure width of the valve may decrease significantly from diastole to systole, having the width of the coaptation assist body being less than the commissure-to-commissure width may help limit disadvantageous bending of the coaptation assist body during cardiac cycles. Some embodiments may employ coaptation assist bodies having a first lateral width adjacent the annulus that is configured for sealingly engaging against the valve at the first commissure and at the second commissure. The coaptation assist body of the supported implant can taper axially inwardly downstream of the coaptation zone so that a downstream width of the coaptation assist body is less than the first width, with the downstream end preferably being rigidly or resiliently supported by a third anchor deployed in the ventricle of the heart. Where the coaptation assist body comprises a conformable material such as ePTFE, such a triangular structure may be constrained in a relatively small diameter catheter and easily and accurately deployed within the valve using plastically deformable polymers or the like, often without having to rely on exotic resilient flexible structural shapes or being subject to fatigue failures related to the significant changes in size of the valve annulus during beating of the heart.

A variety of known or new support structures can be used to support the coaptation assist body within the valve of the heart. In exemplary embodiments, a first lateral edge of the coaptation assist body will be supported with a first support interface adjacent the first commissure. A second lateral edge of the coaptation assist body can similarly be supported with a second support interface adjacent the second commissure. Each of the first and second support interfaces should ideally be able to transmit loads between the coaptation assist body and tissue of the heart so as to maintain a desired position of the implant when the annulus of the heart changes in diameter by more than 10% with each beat of the heart, typically by more than 15%, and ideally by about 20% or more. While some embodiment may employ arcuate support structures extending around the valve annulus or structural interconnects which seek to resiliently or rigidly span the annulus (optionally so as press outwardly against opposed regions of the annulus during at least a portion of heart beat cycle), preferred approaches will avoid the limitations on cardiac tissue movement and/or limits to fatigue life of the implant that may result. By instead employing functionally separate anchor structures near each commissure, which anchors can be independently deployed (and if desired, independently removed and repositioned), these embodiments present significant structural advantages without having to limit tissue movement or implant life.

Exemplary embodiments of the structural interfaces supporting the coaptation assist body may include a tissue penetrating body that can be advanced from within a chamber of the heart into a tissue of the heart. For example, the interface may employ a helical body having a helical axis, so that advancing of the helical body into the tissue of the heart can be performed by rotating the helical body about the helical axis so as to screw the helical body into a tissue of the heart adjacent the annulus. When the interface relies on an annular support structure adjacent the annulus, at least one of the support interfaces may comprise a sliding interface between the annular support structure and the coaptation assist body so as to accommodate tissue motion without limiting fatigue life. An apical end of the coaptation assist body may extend axially from the annulus toward a ventricular apex of the heart, and the apical end of the coaptation assist body can be supported relative to a ventricular tissue of the heart with a ventricular support interface such as an anchor deployed between the papillary muscles. The apical end of the coaptation assist body can be affixed to a tissue-engaging surface of the anchor or other ventricular support interface, or a resilient (including superelastic) structure such as a spring, elastic fabric, metal coil, or the like may alternatively resiliently support the apical end of the coaptation assist body relative to a tissue engaging surface of the ventricular support interface so as to support the implant throughout changes in axial length of the ventricle during beating of the heart. Although optional embodiments might include a shaft or other structural member extending from tissues of the ventricle toward the atrium so as to axially maintain the coaptation assist body up within the coaptation zone, many embodiments can forego such compressively loaded structures.

The relative sizes and shapes of the coaptation assist bodies may be selected in response to characterization of the mal-coaptation of a particular patient's mitral valve, in response to valve measurements, and/or the like, but will often include certain common characteristics that enhance the functioning and/or deployment of the implant. When the implant is in a nominal configuration (such as when the coaptation assist device is unconstrained and at rest within blood or another suitable fluid) the coaptation assist body may have an axial length, a thickness between the coaptation surfaces, and a commissure-to-commissure width. Similarly, when the implant is deployed, coaptation assist device may similarly have an axial length, a thickness, and a width. When the implant is in the nominal and/or deployed configuration the width may be from 5 mm to 35 mm, typically being about 20 mm. Preferably, when the implant is in the nominal and/or deployed configuration the thickness will typically be from 0.5 mm to 10 mm, preferably being about 3 mm; and in many cases less than 20% of the width, often less than 15% of the width, optionally being less than 10% of the width. In many embodiments, when in the nominal and/or deployed configuration, the length will be from 20 mm to 60 mm, preferably being about 40 mm; and generally at least 75% of the width, typically being at least 150% of the width, and in many cases being at least 175% or even at least 200% of the width. The commissure-to-commissure width of the coaptation assist body can be less than a measured commissure-to-commissure width of the patient's valve during diastole or even slightly less than a measured commissure-to-commissure width of the valve during systole, such that the coaptation assist body fits within the valve without being excessively distorted or impinged upon along its lateral edges. Nonetheless, the width of the coaptation assist body will typically be adequate to induce sealing of the valve. In some cases, the coaptation assist body may be only a portion of a measured valve width, which could be as small as 75% or even 60%.

The implants described herein will often be deployable from a lumen of a trans septal or other atrial access catheter, an outer profile of the catheter deployment system typically being less than 19 Fr, often being less than 16 Fr, in many cases being 14 Fr or less. The coaptation assist body may be deployable by removing the coaptation assist body from within the surrounding deployment catheter and laterally expanding the coaptation assist body from an insertion profile to a deployed profile. The coaptation assist body may expand laterally by unfurling, unfolding, and/or unrolling the coaptation assist body. In some embodiments, the coaptation assist body has an insertion volume within the deployment catheter and a deployed volume greater than the insertion volume, with the body volumetrically expanding within the heart so as to increase a thickness of the coaptation assist device between the first and second coaptation surfaces after it is removed from the catheter lumen. The coaptation assist body may comprise a permeable material, and may be configured to volumetrically expand without resorting to inflating the coaptation assist body using inflation fluid introduced from outside a vascular system of the patient. In other embodiments, balloon-inflation like expansion may be used, or the coaptation assist body may have an insertion volume within the deployment catheter, and the implant may be configured so as to inhibit mal-coaptation without volumetrically expanding the coaptation assist body from the insertion volume. In some embodiments, and particularly where the mal-coaptation of the valve varies along the curve prior to implantation (for example, when there is prolapse of a segment of the mitral valve such as A2-P2), the variation in mal-coaptation along the curve may be characterized using imaging (such as ultrasound imaging, fluoroscopy, angiography, computer tomography, magnetic resonance imaging, or the like). A thickness of the deployed coaptation assist body between the first coaptation surface and the second coaptation surface may vary along the curve in response to the characterization of the variation in mal-coaptation, optionally by selecting of an appropriate valve body from among a plurality of alternative valve bodies in response to the characterization.

The use of at least partially independent anchors separated about the tissues of the heart and/or of mountingly coupling the valve body to the at least initially deployed anchors significantly facilitates implantation. Selectively deploying the first and second anchors may be performed by directing the first anchor toward the first target location, and directing the second' anchor (often after the first anchor has been at least initially deployed and independently of the directing of the first anchor) toward the second target location. The directing of the first anchor can be performed by steering a steerable catheter body from outside the patient, and the directing of the second anchor can be performed by steering the same steerable catheter body. The steerable catheter body may support an electrode sensing surface, and an electrogram may be sensed at candidate target locations when the electrode sensing surface is connected externally to an electrical signal recording device. Alternatively, the valve anchor itself may have electrical sensing capability and connected externally to an electrical signal recording device, or both catheter body and anchor may have electrical sensing capability. The first and/or second target locations can be sensed in response to the electrograms of the candidate target location, such as by determining when the electrogram has a desired signal corresponding to one or more of the major structures of the heart (for example, a desired mix of atrial and ventricle signals to identify axial positioning relative to the valve annulus, with or without a mix of signals indicative of lateral positioning relative to the septum or other anterior/posterior structures. Tactile indications of the annulus and commissures may also be employed, optionally under ultrasound and/or fluoroscopic imaging.

The separate deployment of the anchors may also facilitate verification that adequate support will be provided. For example, the first anchor may be configured to be initially deployed while remaining coupled to the deployment system, such as by keeping a torqueable body connected to a helical anchor after the anchor has been screwed into the heart tissue from within the heart. It will then be possible to determine that the initially deployed first anchor is not satisfactory, such as by applying tension to the connecting body, via electrogram signals transmitted from the anchor, or the like. The initially deployed first anchor can then be disengaged from tissue of the heart, aligned with the first target location, and re-deployed. It will then be relatively straightforward to verify that the first anchor deployment at the first target location is acceptable, and the initial deployment, moving, and verifying can all be performed without disengaging the second anchor from the second target location (either because it was not yet even initially deployed, or by leaving the second anchor in engagement with the target tissue throughout the process).

The coaptation assist body to be implanted in a particular patient may be selected from among a plurality of alternatively selectable coaptation assist bodies included with the implantation system. The alternative bodies may have differing geometries suitable for mitigating mal-coaptation of differing patients, and may be selected for implantation with the anchors into the patient, optionally after at least one of the first and second anchors are at least initially deployed, such as in response to a measurement of a location, separation, or other characteristic of the deployed first and second anchors. Some or all of the coaptation assist bodies may have flanges that protrude laterally from the coaptation surface when the coaptation assist bodies are in their nominal or deployed configurations, which the flanges often being configured so as to inhibit leaflet prolapse. The geometries of the flanges will often differ among the coaptation assist bodies so as to facilitate mitigation of differing leaflet prolapse characteristics of different patients by selecting an appropriate coaptation assist body for that patient, often in response to imaging or measurement of the heart. For example, flanges may protrude from the anterior and/or posterior coaptation surfaces, may have differing protrusion lengths, surface shapes, and/or axial positions, may have differing lateral widths and lateral positions, and the like.

The coaptation assist body may be supportingly coupled in vivo with the first and/or second anchors after the first and/or second anchors are initially deployed. A third anchor may be configured to be deployed at a third target location axially offset from the first and second target locations, optionally within the left ventricle such as a region of the ventricle of the heart between papillary muscles of the ventricle. The third anchor may be pre-mounted to the valve body, and or may otherwise be configured to be advanced within the deployment system toward the third target location after the first and second anchors are deployed, using either the same steerable catheter or a different steerable catheter. The third anchor can be rigidly affixed to an apical portion of the coaptation assist body, with the body configured to accommodate relative movement between the anchors during beating of the heart with deformation (such as lateral flexing and/or axial resilient elongation) of the coaptation assist body In some embodiments, an axially resilient structure and/or material such as a spring, a resilient polymer material such as a silicone elastomer, or the like may couple the third anchor to the apical portion of the coaptation assist body so as to accommodate the relative movement between the anchors. Still further options might be provide, including supporting the coaptation assist body with the third anchor via a tether coupling the third anchor to an apical portion of the coaptation assist body, and further comprising accommodating relative movement between the anchors during beating of the heart with resilient deformation of the coaptation assist body between the tether and the first and second anchors.

Advantageously, the devices and systems described herein can allow a physician to determine an effectiveness of the implant at mitigating the mal-coaptation while a delivery catheter remains coupled to at least one of the anchors and/or to the coaptation assist body. The catheter may remain coupled to the anchors such that the catheter system does not impose a significant load on the implant, such that the implant can be evaluated for effectiveness in substantially the position and configuration the implant will have once the catheter system is decoupled and removed. If the desired results are not seen, the physician can move and/or replace the coupled anchor, and/or can replace the coaptation assist body while leaving at least another of the anchors deployed. While some exemplary anchor embodiments use a tissue penetrating helical body having a helical axis configured for rotating the helical body about the helical axis so that helical body penetrates the first target location from within the heart, a variety of alternative anchors might be used. In some embodiments, the anchors might comprise suture, clips, staples, radiofrequency energy welds, or the like, and may be used to mount the body to heart tissue within the heart in an open surgical approach, during a robotic or endoscopic procedure, with access to the valve optionally being provided through a puncture or incision through the ventricular apex or atrial appendage, or the like. The implant will typically be configured so that, when deployed, loads transmitted between the coaptation assist body and tissue of the heart allow the annulus of the heart valve to change in diameter by more than 10% with each beat of the heart. Despite these significant size excursions, and despite the first and second anchors being circumferentially separated around the annulus, the anchors may each support the deployed implant sufficiently independently of the other to inhibit subjecting any resilient (including super-elastic) anchor-anchor interconnecting structure to fatigue-related failure during long-term implantation. Hence, the invention can be used as a mitral leaflet coaptation enhancement device configured to be positioned within the mitral valve during a brief, minimally invasive procedure, and can improve valve function without requiring reshaping of all or part of the mitral annulus, and without changing leaflet edge anatomy (such as by fusing leaflet edges or the like).

BRIEF DESCRIPTION OF THE DRAWINGS

FIGS. 3F-3G2 schematically illustrate a side view and cross-sections through an exemplary coaptation assist body.

FIGS. 3H-3Q schematically illustrate attachment of the coaptation assist body to anchors and varying geometries of alternatively selectable coaptation assist bodies.

DETAILED DESCRIPTION OF THE PREFERRED EMBODIMENT

Figure 1A:
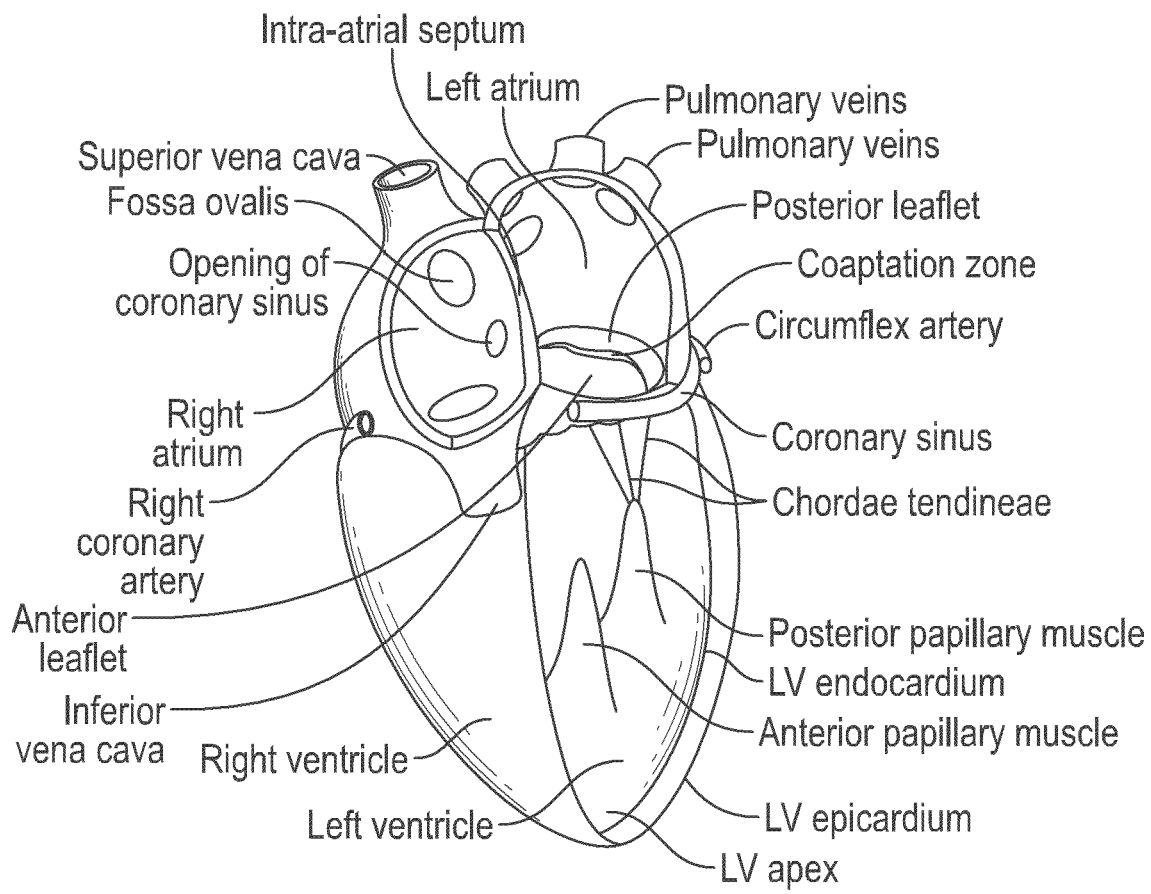
FIGS. 1A-1E schematically illustrate some of the tissues of the heart and mitral valve, as described in the Background section and below, and which may interact with the implants and systems described herein.
Figure 1B:
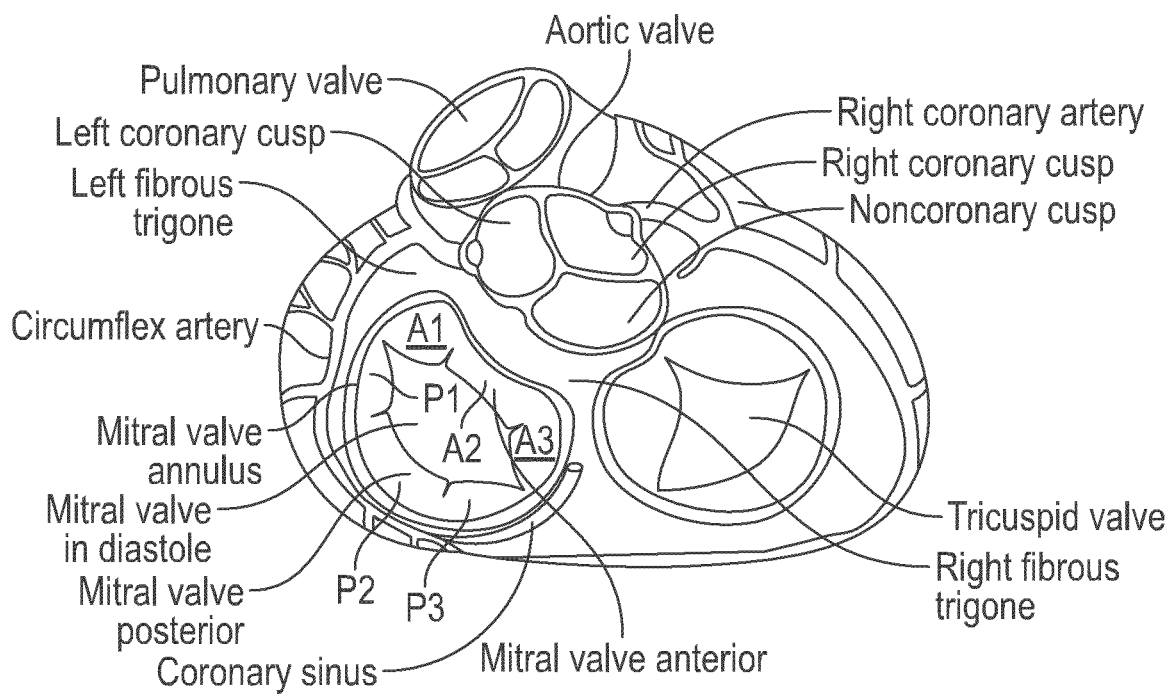
Figure 1C:
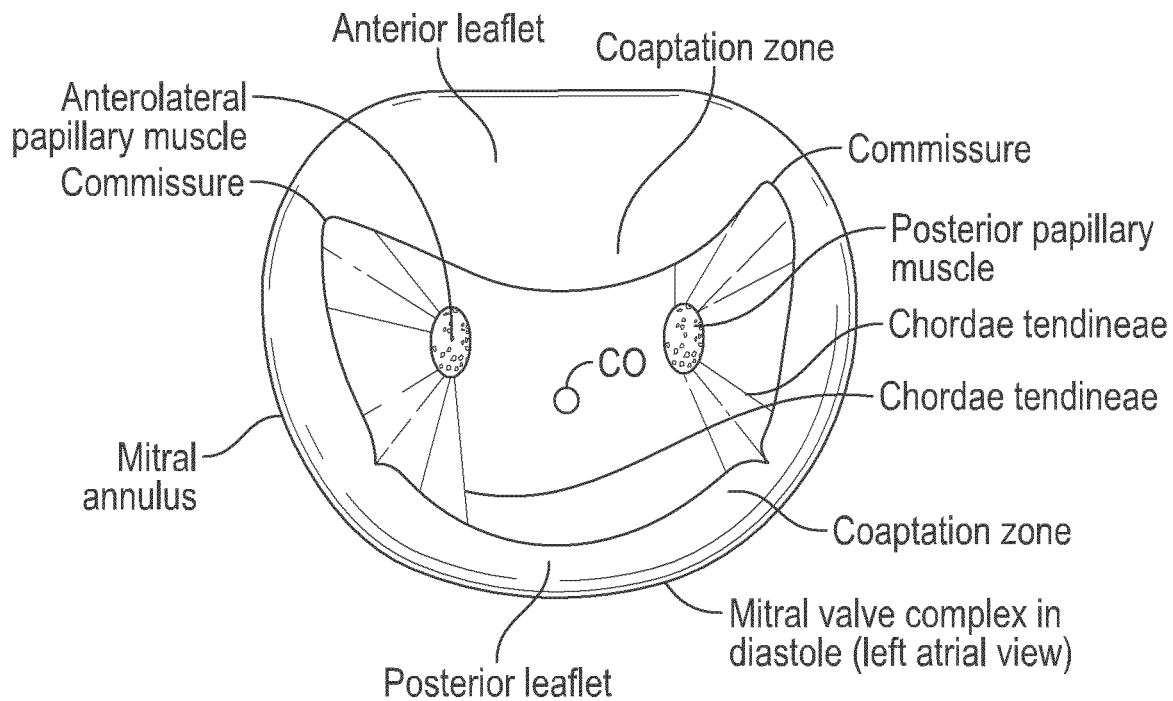
Figure 1D:
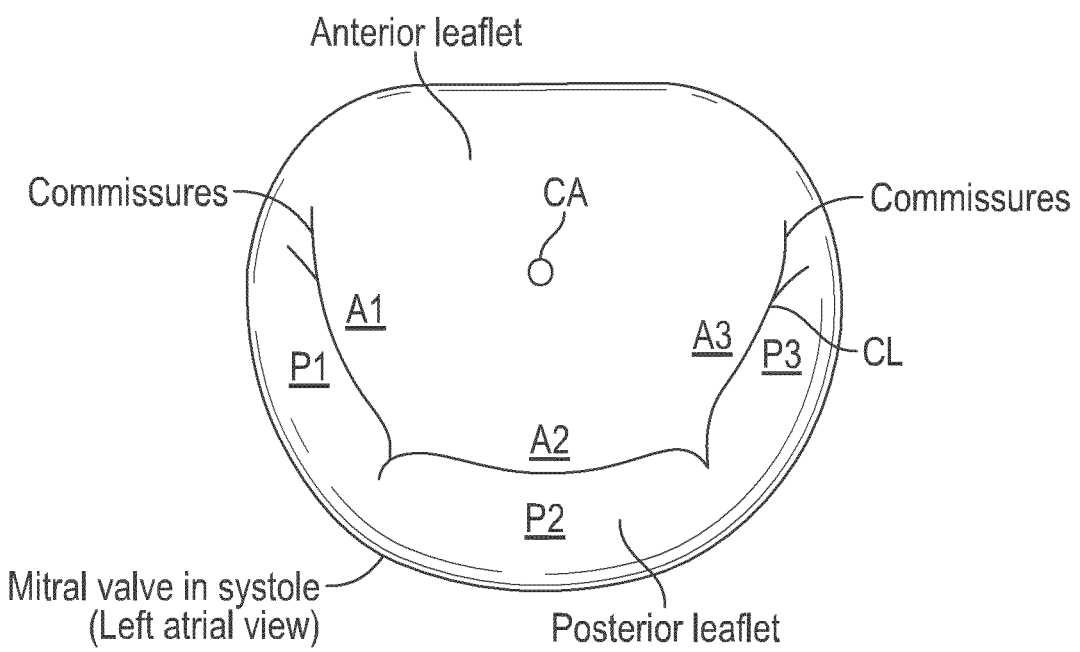
Figure 1E:
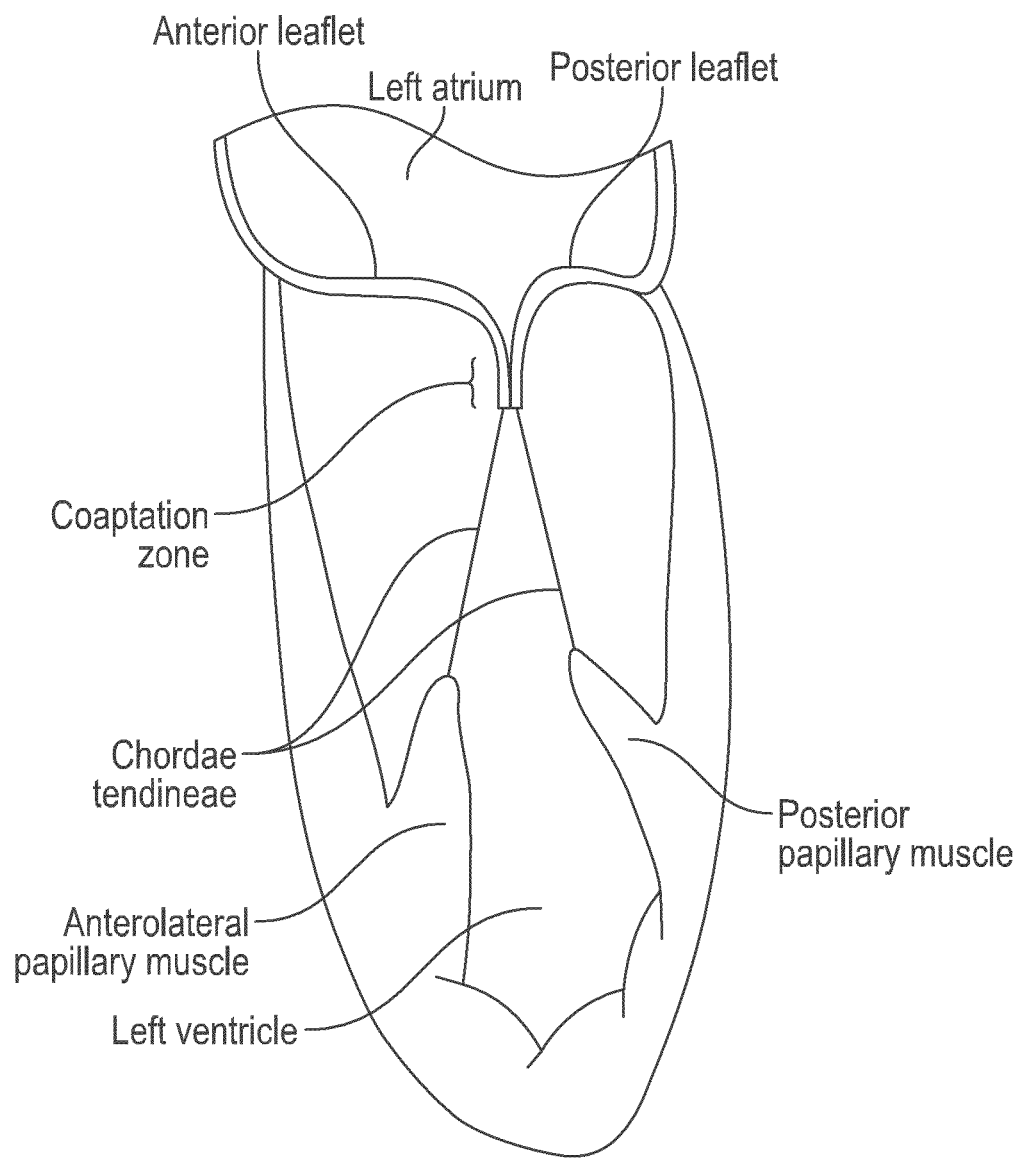

The present invention generally provides improved medical devices, systems, and methods, often for treatment of mitral valve regurgitation and other valve diseases. The implants described herein will generally include a coaptation assist body (sometimes referred to herein as a valve body) which is within the blood flow path as the leaflets of the valve move back and forth between an open-valve configuration (with the leaflets separated from valve body) and a closed-valve configuration (with the leaflets engaging opposed surfaces of the valve body). The valve body may structurally float or move within the annulus of the valve during beating of the heart, and will be disposed between the native leaflets to fill gaps between the coapting leaflet surfaces. Those gaps may be lateral (such as may be caused by a dilated left ventricle and/or mitral valve annulus) and/or axial (such as where one leaflet prolapses or is pushed by fluid pressure beyond the annulus when the valve should close.

Among other uses, the coaptation assistance devices, implants, and methods described herein may be configured for treating functional and/or degenerative mitral valve regurgitation (MR) by creating an artificial coaptation zone within which each of the native mitral valve leaflets can seal. The structures and methods herein will largely be tailored to this application, though alternative embodiments might be configured for use in other valves of the heart and/or body, including the tricuspid valve, valves of the peripheral vasculature, or the like.

Referring to FIGS. 1A-1E, there are several conditions or disease states in which the leaflet edges of the mitral valve fail to appose sufficiently and thereby allow blood to regurgitate in systole from the ventricle into the atrium. Regardless of the specific etiology of a particular patient, failure of the leaflets to seal during ventricular systole is known as mal-coaptation and gives rise to mitral regurgitation.

The fibrous annulus, part of the cardiac skeleton, provides attachment for the two leaflets of the mitral valve, referred to as the anterior leaflet and the posterior leaflet. The leaflets are axially supported by attachment to the chordae tendineae. The chordae, in turn, attach to one or both of the papillary muscles of the left ventricle. In a healthy heart, the chordae support structures tether the mitral valve leaflets, allowing the leaflets to open easily during diastole but to resist the high pressure developed during ventricular systole. In addition to the tethering effect of the support structure, the shape and tissue consistency of the leaflets helps promote an effective seal or coaptation. The leading edges of the anterior and posterior leaflet come together along a funnel-shaped zone of coaptation, with a lateral cross-section of the three-dimensional coaptation zone CZ being shown schematically in FIG. 1E.

Generally, mal-coaptation can result from either excessive tethering by the support structures of one or both leaflets, or from excessive stretching or tearing of the support structures. Other, less common causes include infection of the heart valve, congenital abnormalities, and trauma.

Valve malfunction can result from the chordae tendineae becoming stretched, known as mitral valve prolapse, and in some cases tearing of the chordae or papillary muscle, known as a flail leaflet. Or if the leaflet tissue itself is redundant, the valves may prolapse so that the level of coaptation occurs higher into the atrium, opening the valve higher in the atrium during ventricular systole. Either one of the leaflets can undergo prolapse or become flail. This condition is sometimes known as structural mitral valve regurgitation.

In excessive tethering, the leaflets of a normally structured valve may not function properly because of enlargement of or shape change in the valve annulus: so-called annular dilation. Such functional mitral regurgitation generally results from heart muscle failure. And the excessive volume load resulting from functional mitral regurgitation can itself exacerbate heart failure, ventricular and annular dilation, thus worsening mitral regurgitation.

The anterior and posterior mitral leaflets are dissimilarly shaped. The anterior leaflet is more firmly attached to the annulus overlying the central fibrous body (cardiac skeleton), and is somewhat stiffer than the posterior leaflet, which is attached to the more mobile posterior lateral mitral annulus. The coaptation zone between the leaflets is not a simple line, but rather a curved funnel-shaped surface interface. The commissures are where the anterior leaflet meets the posterior leaflet at the annulus. As seen most clearly in the axial views from the atrium of FIGS. 1C and 1D, an axial cross-section of the coaptation zone generally shows the curved line CL that is separated from a centroid of the annulus CA as well as from the opening through the valve during diastole CO. In addition, the leaflet edges are scalloped, more so for the posterior versus the anterior leaflet. The generally 3 scallops, or segments, are referred to as the A1, A2, and A3, and P1, P2, and P3 segments. Mal-coaptation can occur between one or more of these A-P segment pairs, so that mal-coaptation characteristics may vary along the curve of the coaptation zone CL.

Figure 2A:
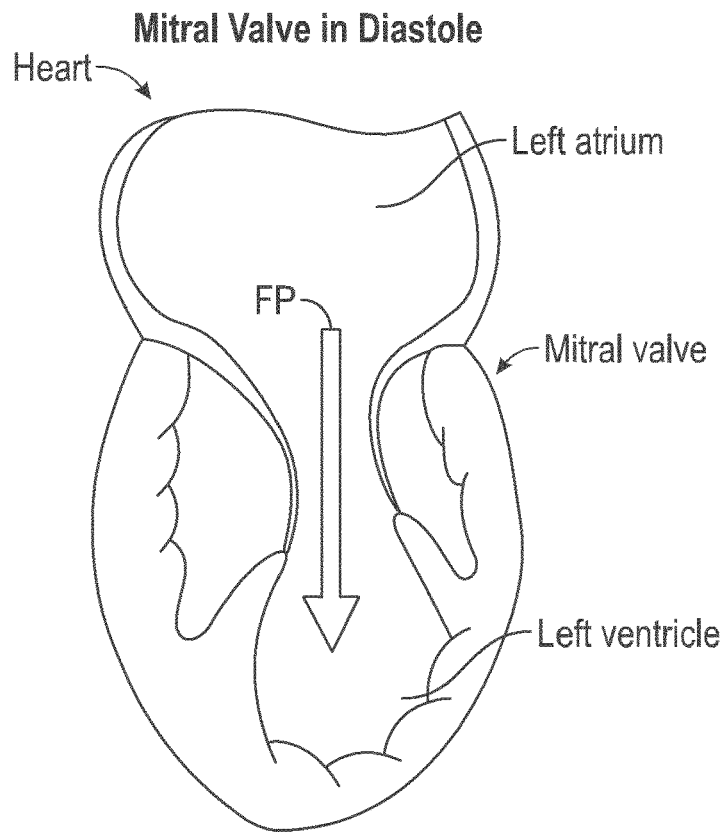
FIGS. 2A-2C illustrate a simplified cross-section of a heart, schematically showing mitral valve regurgitation related to mal-coaptation.
Figure 2B:
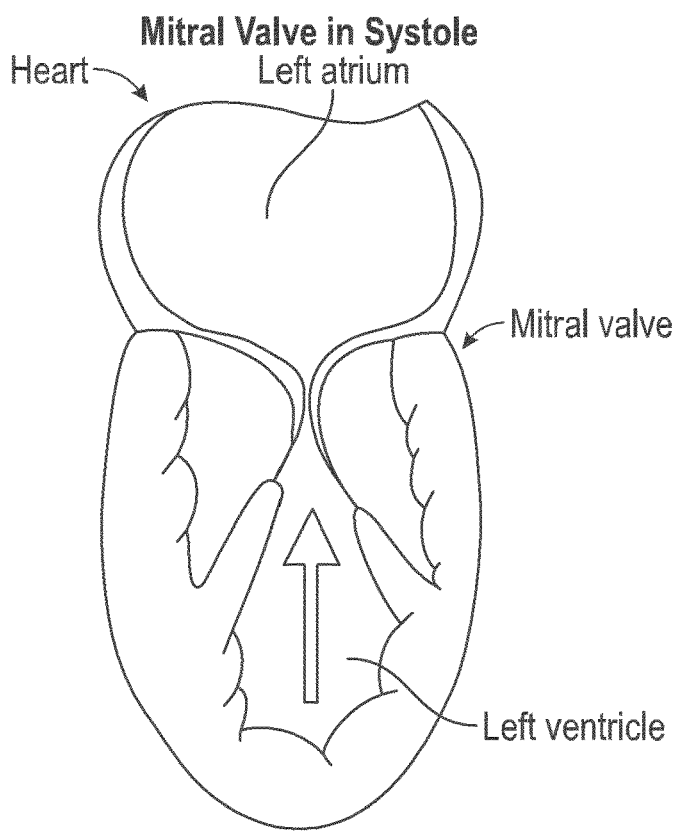
Figure 2C:
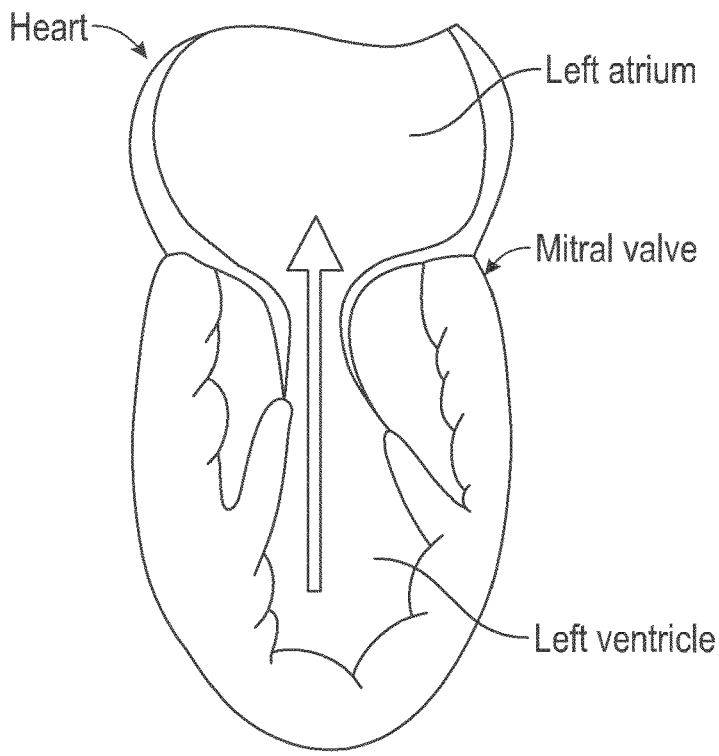

Referring now to FIG. 2A, a properly functioning mitral valve MV of a heart H is open during diastole to allow blood to flow along a flow path FP from the left atrium toward the left ventricle LV and thereby fill the left ventricle. As shown in FIG. 2B, the functioning mitral valve MV closes and effectively seals the left ventricle LV from the left atrium LA during systole, thereby allowing contraction of the heart tissue surrounding the left ventricle to advance blood throughout the vasculature. However, as illustrated in FIG. 2C, in a patient suffering from mitral valve regurgitation, mal-coaptation of the leaflets of the mitral valve MV during systole allows blood to regurgitate or flow backward relative to the intended flow path FP, decreasing the effectiveness of the left ventricle compression.

Figure 2D:
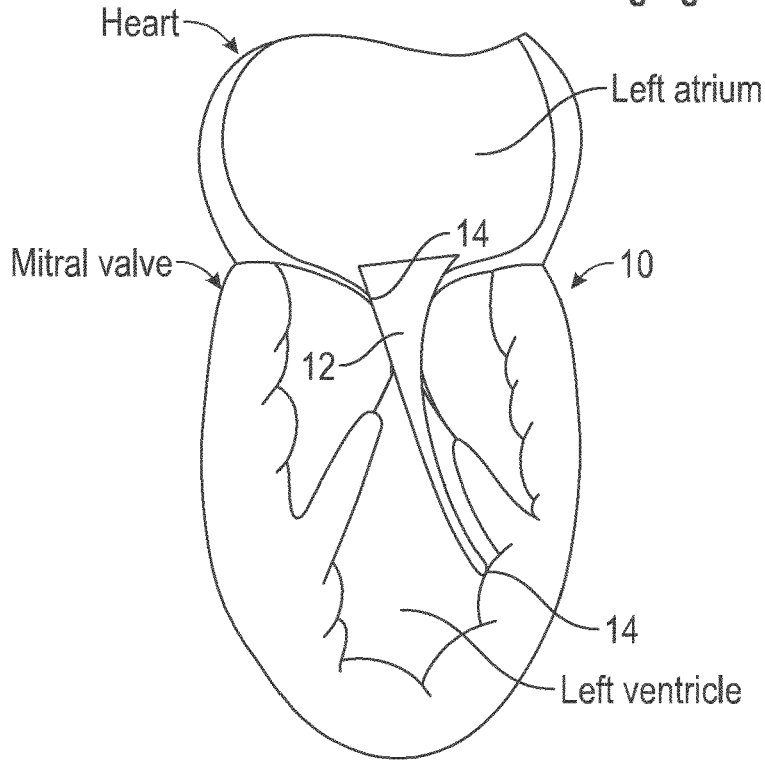
FIG. 2D schematically illustrates an exemplary embodiment of an implant deployed within the mitral valve of FIG. 2C so as to mitigate the mal-coaptation.

Referring now to FIG. 2D, an exemplary embodiment of a coaptation assist implant 10 has been deployed within heart H. Implant 10 includes a coaptation assist body 12 supported relative to the heart tissues by support interface structures, with the exemplary supports making use of independent anchors 14. Coaptation assist body or valve body 12 is configured and positioned so that the anterior leaflet of the mitral valve coapts with a first coaptation surface of the valve body and the posterior leaflet of the mitral valve coapts with a second coaptation surface, with the first and second surfaces being generally opposed so that the valve body is disposed between the previously mal-coapting leaflets. The implant helps mitigate gaps and any axial mismatch between the leaflets when the valve is closed, and may also help reposition the closed leaflets toward a more effectively sealing closed configuration such that the mal-coaptation of the heart valve is mitigated.

Still referring FIG. 2D, independent anchors 14 allow a single anchor to be deployed at an associated target location within the heart without having to concurrently orient another of the anchors toward a different target location. The use of independent anchors also allows an individual anchor to maintain positioning engagement with the target location of the heart before another anchor is moved into alignment with a different target location, and/or allows an anchor to be moved into alignment with a target location of the heart after another anchor has been deployed without moving the deployed anchor, and regardless of the size of the valve body, valve, and/or the like.

The deployed coaptation assist implants described herein may exhibit a number of desirable characteristics. Generally, the deployed implants will mitigate or help correct mitral regurgitation MR due to mal-coaptation, including mal-coaptation secondary to restricted leaflet motion (i.e., excessive tethering of the mitral support structures including the papillary muscles and chordae tendineae.) Similarly, the deployed implants may mitigate or help correct MR due to mal-coaptation secondary to excessive leaflet motion such as associated with mitral valve prolapse or flail leaflet. Exemplary embodiments need not rely on reshaping of the mitral annulus (such as by thermal shrinking of annular tissue, implantation of an annular ring prosthesis, and/or placement of a cinching mechanism either above or beneath the valve plane, or in the coronary sinus or related blood vessels). Advantageously, they also need not disrupt the leaflet structure or rely on locking together or fusing of the mitral leaflets. Many embodiments can avoid reliance on ventricular reshaping, and after implantation represent passive implanted devices with limited excursion which may results in an very long fatigue life. Mitigation of mitral valve mal-coaptation may be effective irrespective of which leaflet segment(s) exhibit mal-coaptation. The treatments described herein will make use of implants that are repositionable during the procedure, and even removable after complete deployment and/or tissue response begins or is completed, often without damaging the valve structure. Nonetheless, the implants described herein may be combined with one or more therapies that do rely on one or more of the attributes described above as being obviated. The implants themselves can exhibit benign tissue healing and rapid endothelialization which inhibit migration, thromboembolism, infection, and/or erosion. In some cases, the coaptation assist body will exhibit no endotheliazation but its surface will remain inert, which can also inhibit migration, thromboembolism, infection and/or erosion.

Figure 3A:
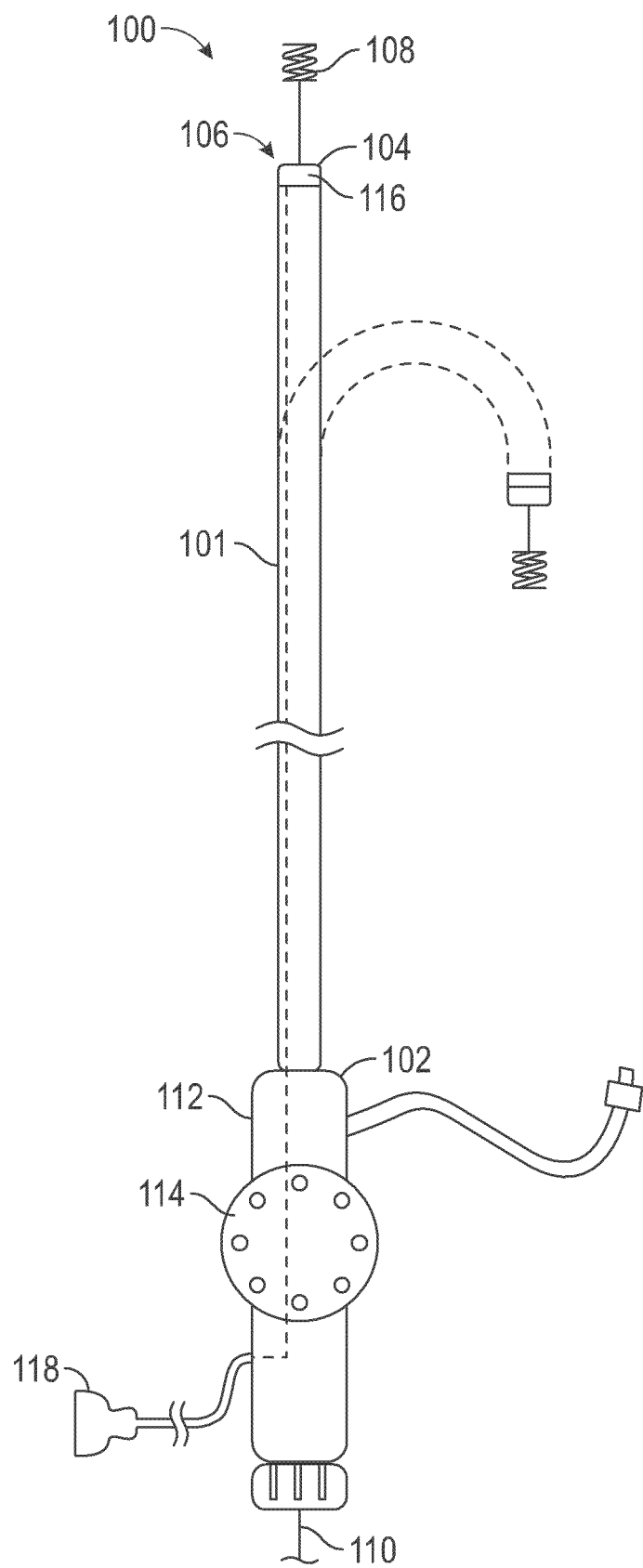
FIGS. 3A and 3B schematically illustrate components of an implant delivery system for mitigation of mal-coaptation.
Figure 3B:
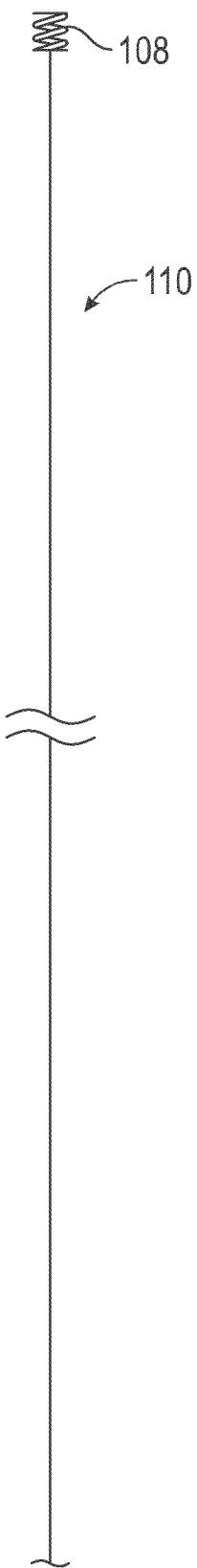
Figure 3C:
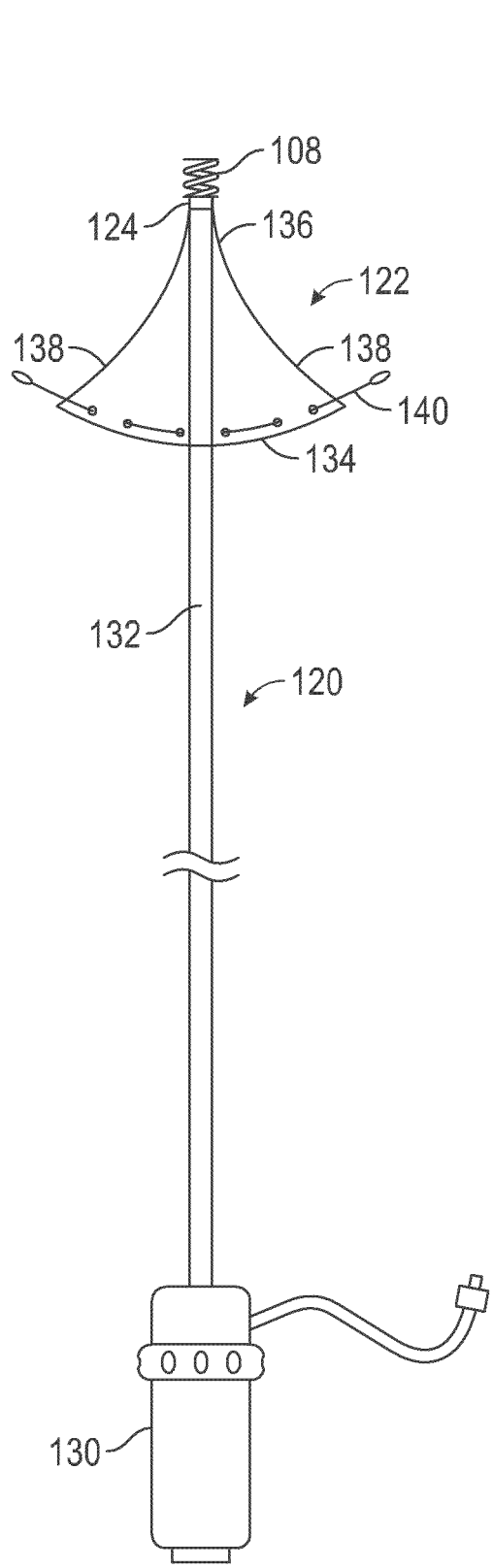
FIGS. 3C and 3D schematically illustrate a coaptation assist body supported by a steerable catheter, with the body in a laterally expanded configuration and in an insertion configuration for advancement through a lumen of a delivery sheath, respectively.

Referring now to FIGS. 3A-3C, components of a coaptation assist system can be seen. An anchor deployment catheter 100 includes an elongate catheter body 101 having a proximal end 102 and a distal end 104, with a lumen 106 extending therebetween. An anchor 108 is mounted to the distal end of an elongate anchor delivery body 110, allowing the anchor to be advanced distally through lumen 106. In the exemplary embodiment, anchor 108 comprises a helical body that can be deployed by torquing the proximal end of anchor delivery body 110 proximally of anchor delivery catheter 100 so as to screw the anchor into the tissue of the heart from within the atrium and/or ventricle, so that anchor 108 can be derived from and/or analogous to a pacemaker lead. A wide variety of alternative anchor structures might also be used.

Referring still to FIGS. 3A-3C, anchor deployment catheter 100 will typically have a proximal handle 112 with an actuator 114 for selectively steering or bending catheter body 101 near distal end 104. By selectively steering catheter 100 and manipulating the handle 112 so as to rotate catheter body 101 and/or axially advance the catheter body, the lumen 106 can be oriented toward a target region within the heart. Catheter 100 may comprise any of a wide variety of know steerable catheter structures, including those which include a pull wire extending distally from actuator 114 to distal end 104 so as to selectively bend and steer the catheter. In an exemplary embodiment, anchor deployment catheter 100 includes an electrode 116 adjacent distal end 104, with the electrode being coupled to a proximal electrogram connector 118 by a signal conductor extending axially within catheter body 101, thereby allowing the physician to measure electrograms from candidate anchor locations prior to deploying the anchor. Regardless of any electrogram sensing capability of the catheter system alone, use of a conductive surface of an anchor (such as the outer surface of a metallic anchor structure) as an electrode may advantageously provide signals directly from the tissue, whereas the catheter structure may be positioned off the tissue. Electrode 116 may also be used as a high-contrast marker under any of a variety of imaging modalities so as to facilitate image guidance of the anchor deployment.

Figure 3D:
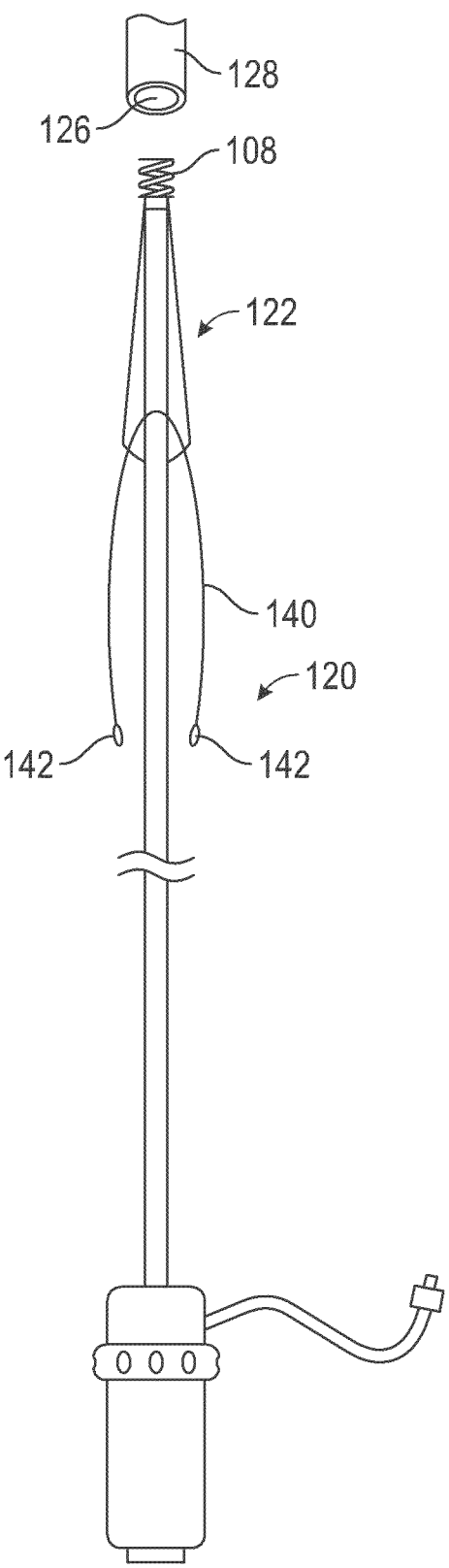

Referring now to FIGS. 3C and 3D, a valve body deployment catheter 120 releasably carries a valve body 122 near a distal end 124. Valve body 122 is seen expanded in its nominal or deployed configuration in FIG. 3C, and with a reduced profile for insertion into a lumen 126 of an outer deployment sheath 128, with the deployment sheath being and lumen being shown schematically. Valve body delivery catheter 120 has a proximal handle 130 and may again be steerable so as to direct an anchor 108 mounted to valve body 122 toward a target location. Catheter body 132 of valve body delivery catheter 120 (or a torquable shaft within the catheter body) may be rotationally and axially coupled to anchor 108 so as to facilitate deployment of the anchor from outside the patient.

Valve body 122 in its nominal or deployed configuration may have an atrial or proximal end 134 and a ventricular or distal end 136, as seen in FIGS. 3C-3F. The valve body may be laterally flexible, (optionally comprising one or more sheets or layers of a flexible tissue-ingrowth or endothelialization matrix such as an expanded polytetrafluoroethylene (ePTFE)) in a roughly triangular configuration, with opposed lateral edges 138 tapering radially inwardly toward the distal end 136 and anchor 108 of the valve body. Alternative valve body materials can also be used including valve bodies formed using allograft and/or xenograft materials, artificial collagenous matrices, alternative polymer materials, or the like. The valve body may include more than one material, including fibers or layers of materials which alter the mechanical characteristics such as to reinforce an ingrowth or endothelialization material, increase or decrease a modulus of elasticity, or the like, with the altered characteristics optionally being provided uniformly or along selected portions of the valve body. A lateral atrial support 140 may be provided, but will often not be relied upon as the primary structure to maintain engagement of the anchors against the tissues of the heart to which they are attached. In the embodiment shown, atrial support 140 may comprise one or more plastically and/or resilient flexible polymer filament such as a suture or the like, one or more filament of a superelastic shape memory alloy such as a Nitinol alloy, one or more superelastic polymer filament, or the like. The atrial end 134 of valve body 122 may slidingly engage atrial support or member 140 so as to facilitate laterally compressing the valve body into outer sheath 138. The ends of atrial support 140 may each include a loop 142 or other structure to slidably engage an elongate anchor delivery body 110 of an associated anchor 108 (see FIGS. 3A and 3B), as will be more fully understood with reference to the description of the steps that can be used during deployment of the implant as provided below.

Figure 3E:
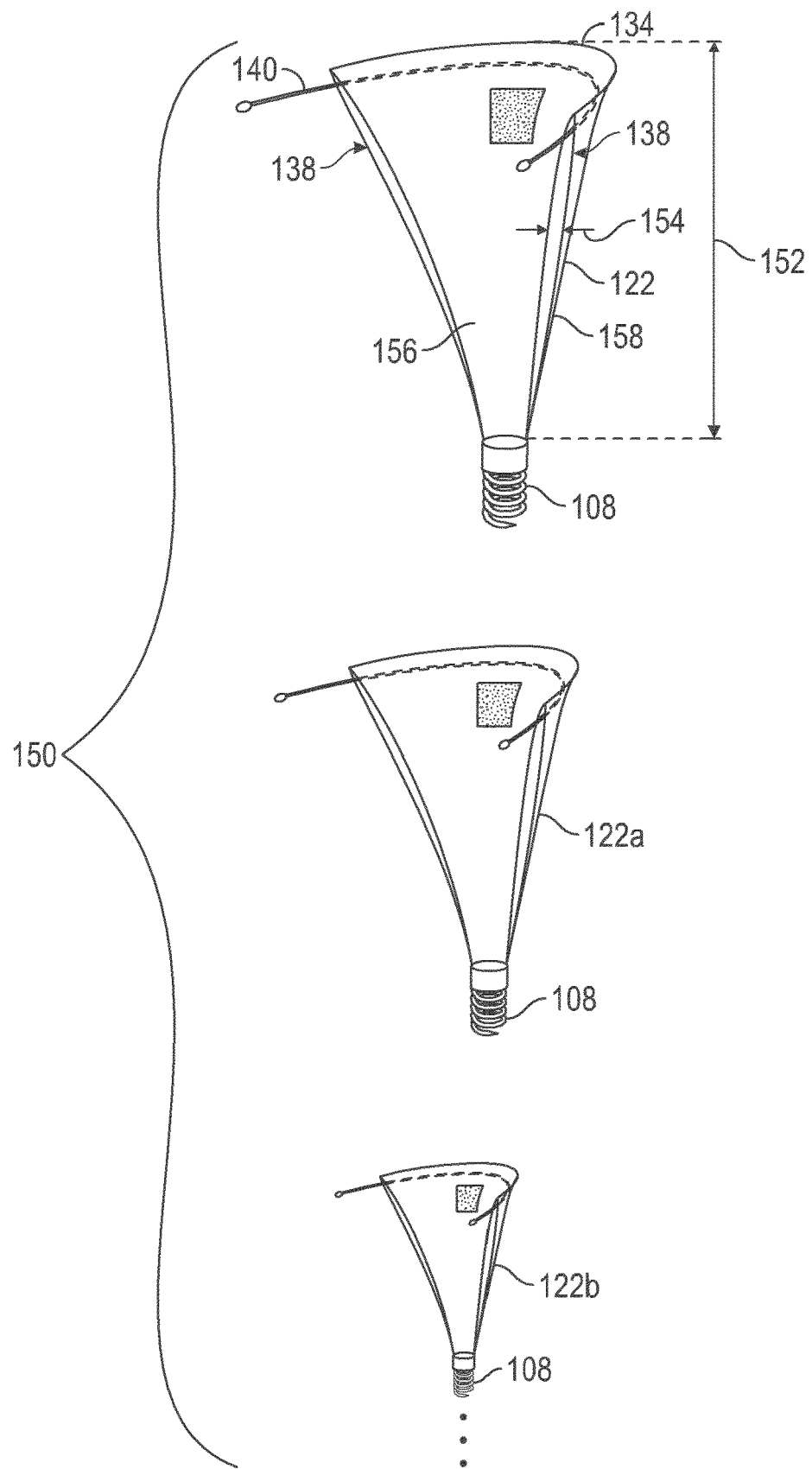
FIG. 3E schematically illustrate a set of alternatively selectable valve bodies for delivery to a valve and in-situ mounting to deployed anchors.
Figure 313:
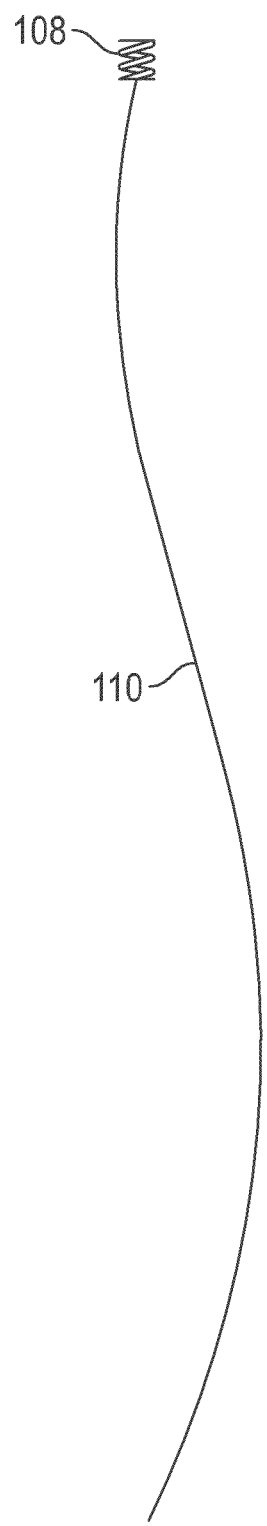
Figure 314:
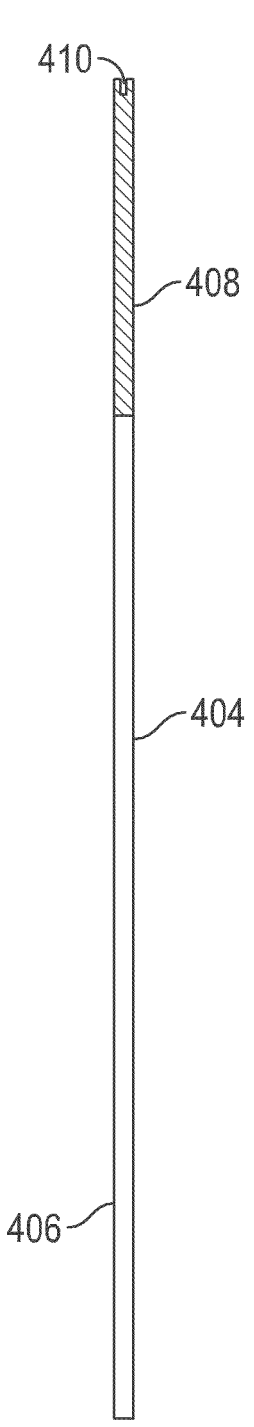
Figure 315:
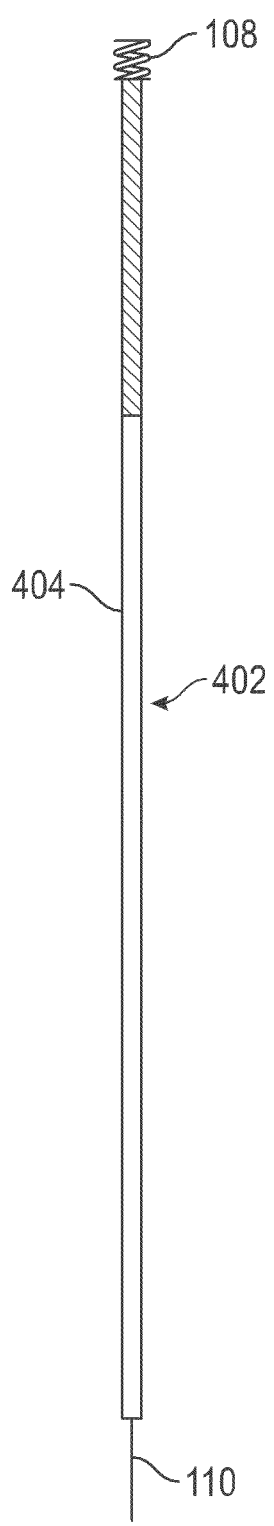
Figure 316:
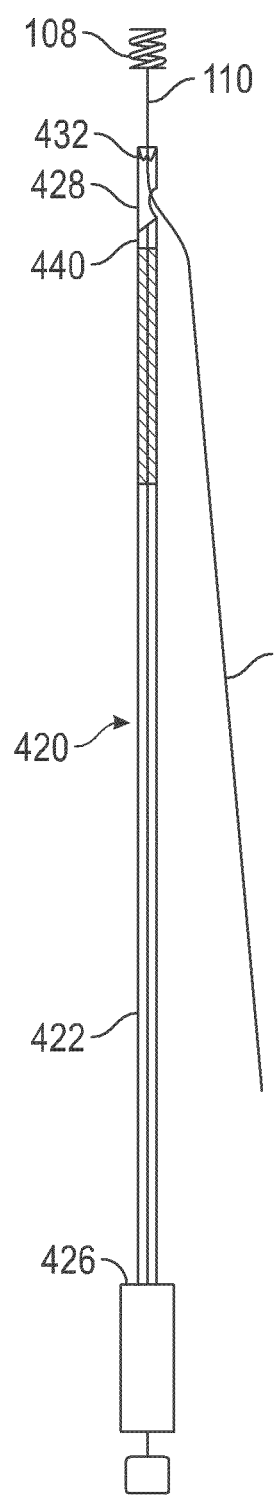
Figure 317:
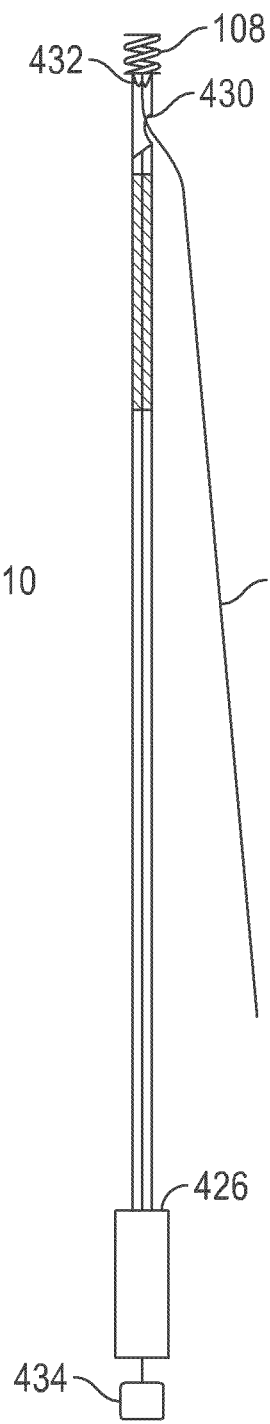
Figure 318:
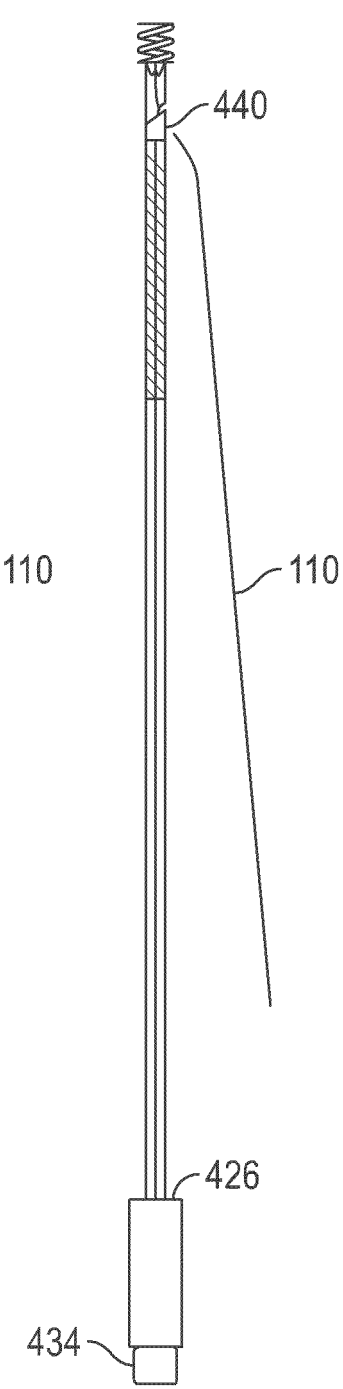
Figure 319:
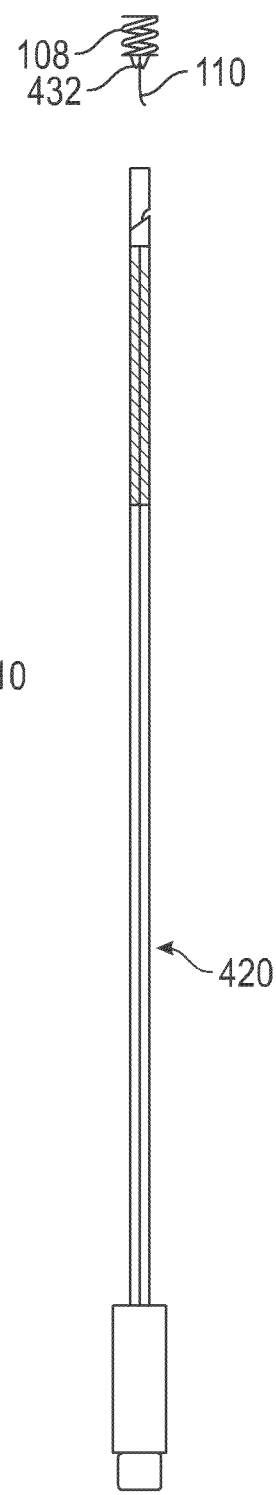

As seen in FIG. 3E, exemplary embodiments of coaptation assist systems may include a set 150 having plurality of alternatively selectable valve bodies, with the various valve bodies 122, 122a, 122b, . . . often having differing geometries. Each valve body 122 will typically have a nominal and/or deployed axial length 152 (with the axial length generally being measured along the axis of the valve when the valve body is positioned for use), a lateral width between lateral edges 138, and a thickness 154 between the opposed major surfaces 156, 158 of the valve body. Each of the native leaflets of the valve will coapt with an associated one of the major surfaces 156, 158 of the valve body 122, so that these surfaces may also be referred to herein as coaptation surfaces. The varying geometries of the various valve bodies 122, 122a, 122b, . . . of valve body set 150 will typically include differing thicknesses 154 (so as to accommodate differing mal-coaptation characteristics), differing axial lengths 152 (so as to accommodate differing ventricle geometries), differing lateral widths between the lateral edges 138 (so as to accommodate differing commissure-to-commissure arcuate distances, differing cross-sectional curvatures (so as to accommodate differences in the curvature line defined by the coaptation zone of the valve), and/or the like. Selecting from among these differing geometries by picking an associated one of the set of valve bodies 150 allows tailoring of the mitral valve regurgitation therapy to the valve disease of a particular patient. Advantageously, the selection of the valve body from the set may also be done after (and in response to) deployment of one or more of the anchors, so that the selected valve body and its associated structural interface may make use of the deployed anchors as measurement fiducials for measuring the valve, and may also be tailored to be suitable for the actual anchor positions within the patient.

Referring now to FIGS. 3G1 and 3G2, schematic axial cross-sections of valve body 122 show an outer tissue ingrowth layer 170 disposed along the opposed major surfaces 156, 158 over a fluid-absorbing core 172. Core 172 can have a small volume configuration prior to implantation (as shown in FIG. 3G2) in which the core has a significantly smaller volume than after core 172 has been deployed within the heart and absorbed fluid. Suitable materials for core 172 may comprise foams including medical grade polyurethane foam, silicone and/or natural rubber foam, hydrogels, a wide variety of hydrophilic polymer matrices, or the like. Core 172 and outer layer 170 may together define a nominal cross-sectional shape of the valve body (including a valve body curve 174) when the valve is unconstrained and absorbs blood or another suitable model fluid. As the valve body will often be a relatively conformable structure with a geometry that can be altered by interaction with tissues, the deployed cross-sectional shape of the valve body (and the overall three-dimensional valve body shape) will often depend on both the nominal shape, the surrounding cardiac tissue, and the characteristics (locations and the like) of the anchors.

Referring now to FIGS. 3H, 3I1, and 3I2, the deployed implant 180 will often support valve body 122 using structural support interfaces that include anchors 108 along with associated structural mountings or couplers 182 so as to facilitate in situ assembly of the valve body and at least one of the anchors. Couplers 182 are shown schematically, but may comprise simple loops or apertures in atrial support 140 or elongate anchor coupling body 110 that allows one of these two structures to slide relative to the other. By sliding a loop 142 of atrial support 140 over a proximal end of elongate anchor coupling body 110 (for example) outside the patient, the atrial support and valve body may be guided distally by deployment body 110 into engagement with the deployed anchor 108. The structural engagement between the deployed anchor and valve body can optionally be completed by crimping the loop closed around the elongate anchor coupling body 110 adjacent the anchor, by advancing a locking structure over the elongate anchor coupling body so as the capture the loop between the anchor and locking structure, by capturing the loop into a latch of the anchor, or by another suitable coupler 182. Once the valve body is supported by the anchor as desired, the elongate anchor coupling body proximal of the connector 182 can be detached and removed. Also shown schematically in FIGS. 3H and 3I1 are axial struts 184 which can be included within valve body 122 so as to inhibit axial bending, thereby enhancing coaptation when the coaptation zone between a first leaflet of the valve and major surface 156 is axially offset from the coaptation zone between a second leaflet of the valve and surface 158.

Referring now to FIGS. 3I3-3I2, an exemplary anchor deployment assembly 402 includes an anchor coupling body 110 and the associated anchor 108, along with an anchor deployment catheter 404. Anchor deployment catheter 404 includes an elongate shaft with a proximal portion 406 extending distally to a more flexible distal portion 408. A distal tip of the flexible portion includes a torque-imparting feature such as a slot 410 to releasably rotationally drive anchor 108 when a transverse member across the helical coil of the anchor axially engages the distal end of anchor deployment catheter (such as when the elongate coupling body 110 proximal of anchor catheter 404 is pulled proximally), allowing the anchor to be rotationally and axially driven into tissue by manipulating the proximal end of the anchor deployment catheter.

Figure 8A:
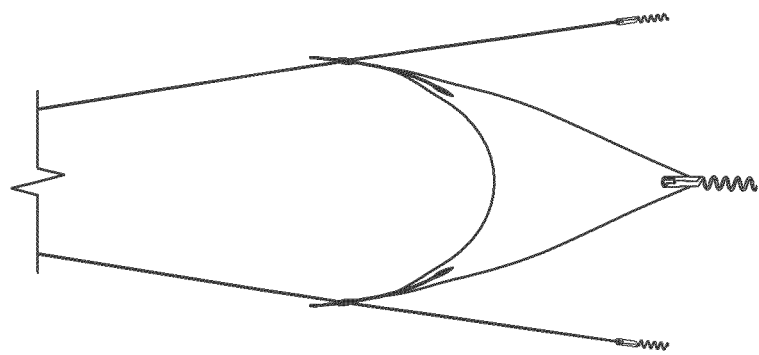
FIGS. 8A-8F illustrate exemplary components of a coaptation assist implant, including sliding engagement between an elongate anchor coupling body and the interface so as to facilitate in situ mounting of the coaptation assist body to the anchor.
Figure 8B:
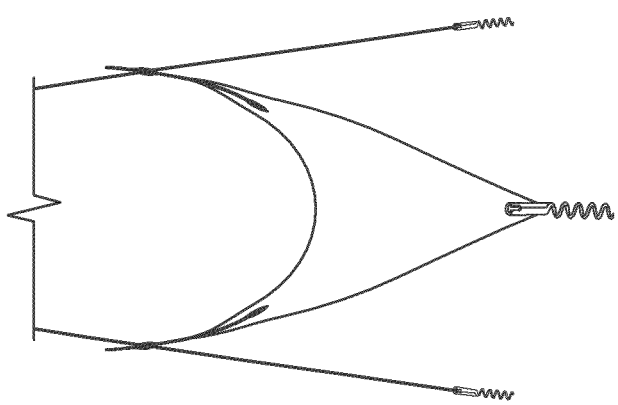
Figure 8C:
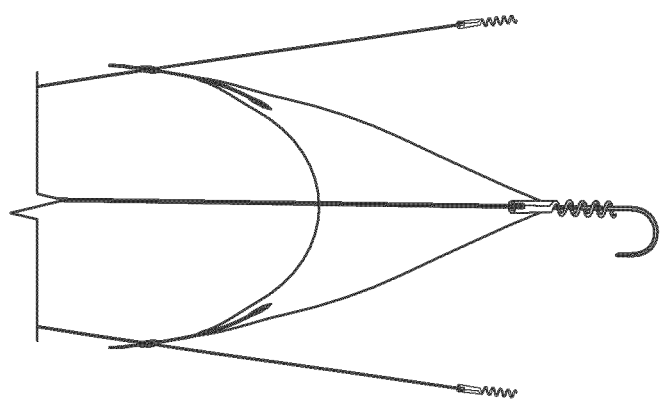
Figure 8D:
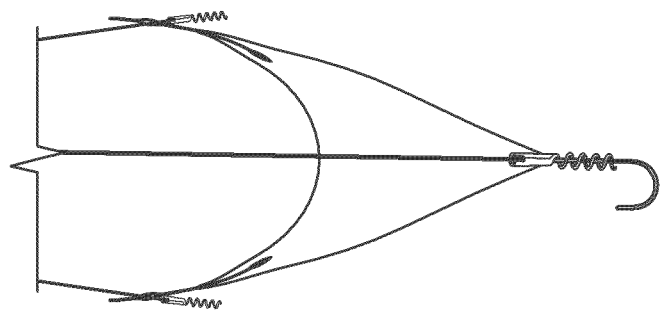
Figure 8E:
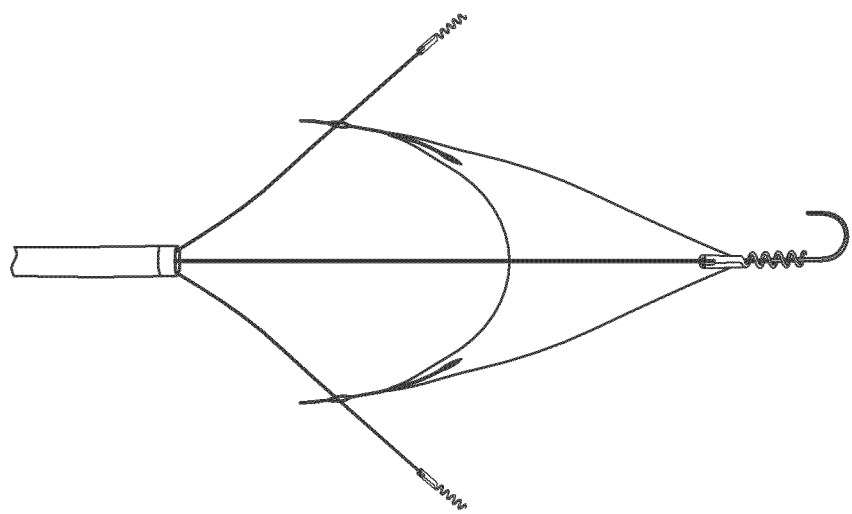
Figure 8F:
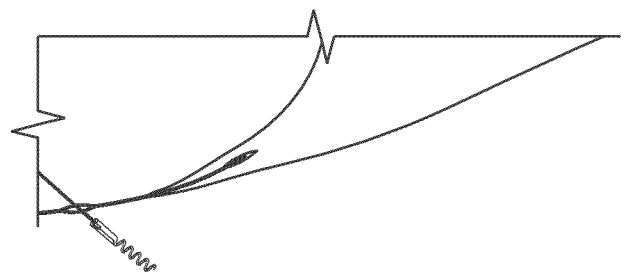
Figure 9:
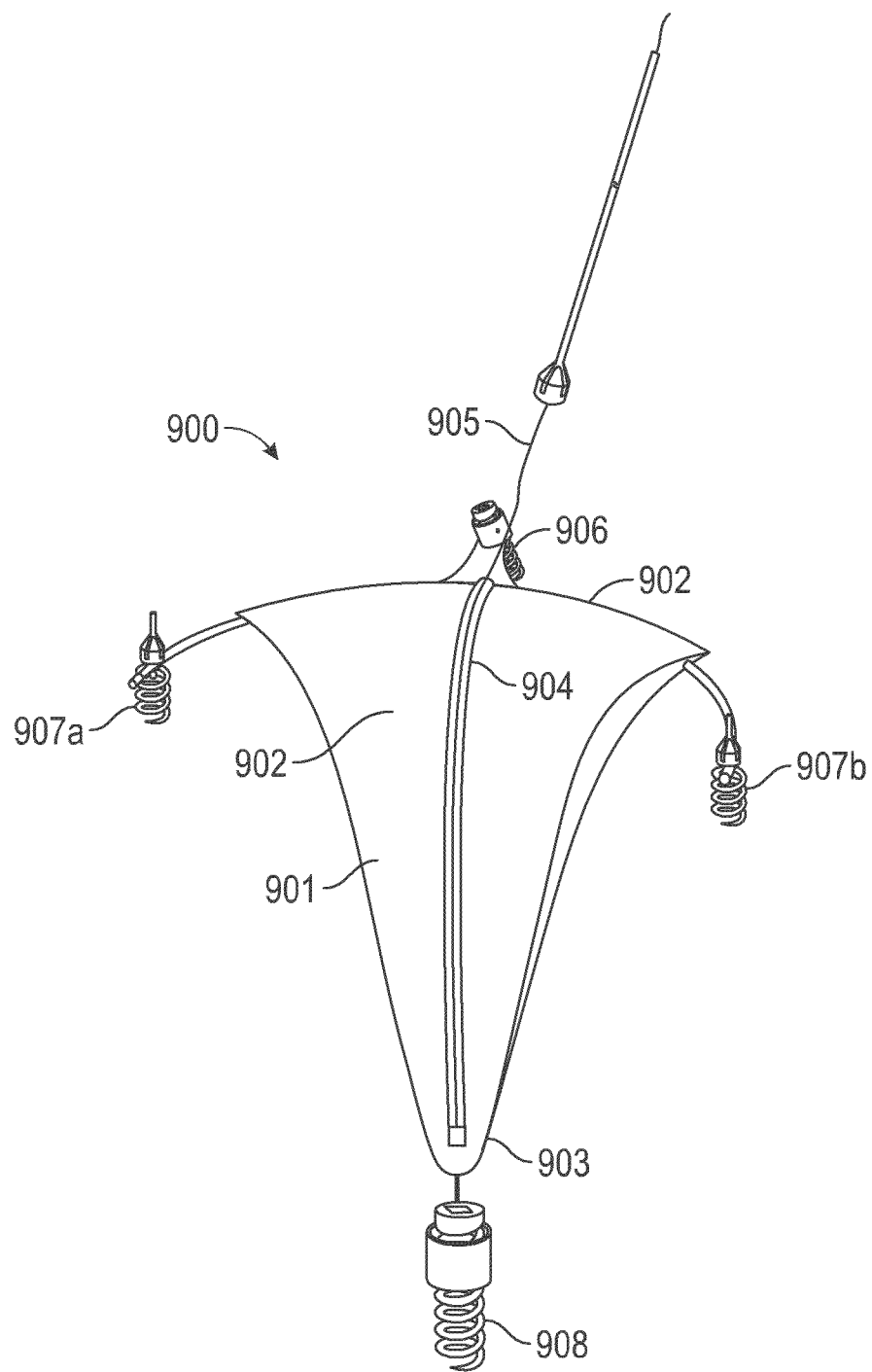
FIG. 9 shows a coaptation device in accordance with embodiments.

The structure and use of an exemplary anchor crimping and cutting assembly 420 can be understood with reference to FIGS. 3I6-3I9. A crimping and cutting catheter 422 includes a shaft 424 that extends distally from a proximal handle 426. A distal portion of shaft 424 is more flexible than a proximal portion, and ends at a distal tip 428 having a side port 430 and releasably supporting a crimp 432. Crimp 432 receives anchor coupling body 110 therethrough, with crimp features configured (such as by being biased radially inwardly, having proximally oriented edges, and/or the like) to allow the coupling body to slide proximally through the crimp but to inhibit distal movement of the coupling body relative to the crimp. A distally oriented surface of crimping and removal catheter 420 engages the crimp, allowing the crimp to be advanced distally along the coupling body 110 by pushing handle 426 distally and/or pulling the coupling body from outside the patient. Once crimp 432 engages (or is sufficiently close to) anchor 108, a cutting knob 434 adjacent handle 426 can be actuated so as to advance a cutting member such as a blade 440 and sever elongate body 110 adjacent anchor 108, as can be understood with reference to FIGS. 3I7 and 3I8. Crimping and cutting catheter 420 can then be decoupled from crimp 432 and anchor 108 by withdrawing the handle proximally, as shown in FIG. 3I9. Note that crimp 432 will often be used to affix an implant to anchor 108 by advancing the implant over the coupling body 110 prior to advancing 432 distally.

Figure 13:
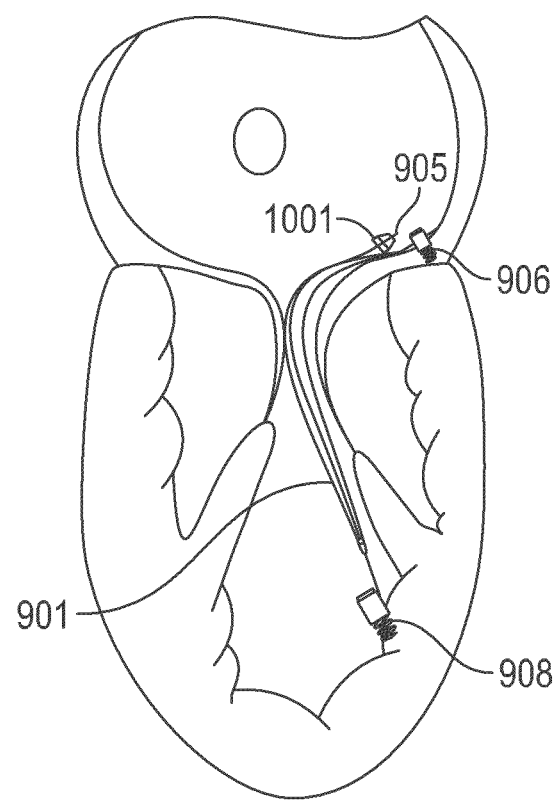
FIG. 13 shows the device of FIG. 9 after deployment within a heart valve and after elements used in the deployment are removed.

An alternative crimping and cutting assembly 420' and associated method can be understood with reference to FIGS. 3I10-3I13, with the assembly here having an alternative cutting member 440' coupled to an energy source 444. Energy source 444 may comprise an ultrasound energy source, a laser energy source, an RF or other electrical energy source, or the like, so that energizing of the cutting member by the energy source facilitates decoupling of the elongate body 110 from the anchor. Note that a wide variety of alternative decoupling and/or cutting systems might be employed, including systems derived from those used to decouple embolism coils and the like. Similarly, a variety of crimping or other anchor/valve body coupling mechanisms may be employed, and a separate crimp catheter structure and cutting catheter structure could be used if desired.

Referring now to FIGS. 3I14-3I17, it can be seen how an aperture through lateral atrial support 140 can be disposed over elongate connector bodies 110 between the anchors 108 and crimps 432, capturing the atrial support and thereby providing a coupler 182 that mounts the valve body 122 to the anchors. Additional details regarding an exemplary ventricular coupler 182 that can be used to affix the ventricular portion of coaptation body 122 to the ventricular anchor 108 can also be seen. More specifically, a hub 450 includes an outer collar and a pin 452 extending laterally therethrough. Ventricular anchor 108 extends axially through hub 450, with the helical winds of the anchor passing above and below pin 452. A torquable feature such as a socket 454 removably engages a driving feature 456, allowing an anchor deployment shaft 458 to rotate the helical anchor from outside the patient through a delivery catheter or sheath 128. As can be understood by comparing the ventricular anchors of FIGS. 3I17 and 3I18, interaction between pin 452 of hub 450 and the helical coils of anchor 108 during rotation of the anchor drives the anchor distally, facilitating advancement into tissue of the ventricle.

Referring now to FIG. 3I18, an implant having an alternative and optionally less traumatic ventricular anchor 460 is shown. Anchor 460 comprises a central shaft 462 and a circumferential array of radially protruding arms 464, with the arms angling proximally when in a nominal or deployed configuration. Arms 464 of anchor 460 may be resiliently compressed inwardly for delivery or advancement within tissue of the ventricle, with the arms optionally retaining the anchor in the heart tissue like barbs, with the arm structures comprising a relatively high strength metal such as a Nitinol alloy, or a high strength polymer. In exemplary embodiments, anchor 460 need not penetrate deeply into the tissue of the heart wall, but can be advanced so that arms 464 less traumatically entangle with the ventricular trabeculae. Such embodiments may employ relatively flexible arm materials and configurations, with the arms optionally comprising relatively soft tines of a polymer such as polyurethane, polyester, nylon, or the like.

Figure 3J:
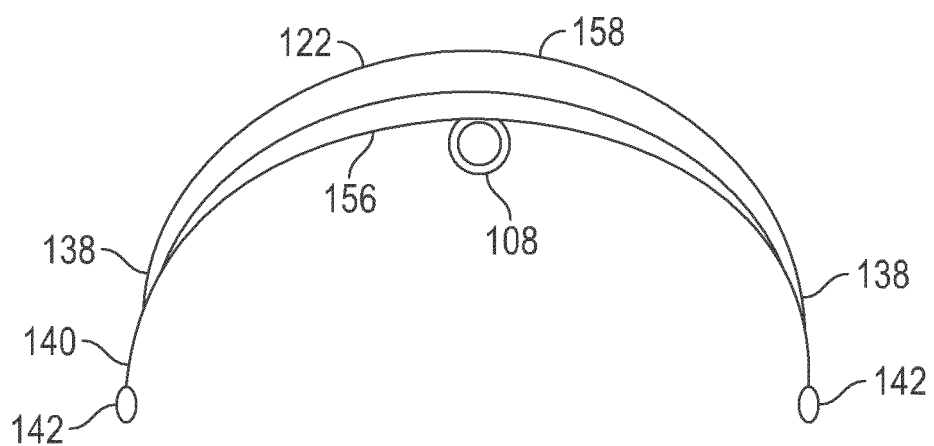
Figure 3K:
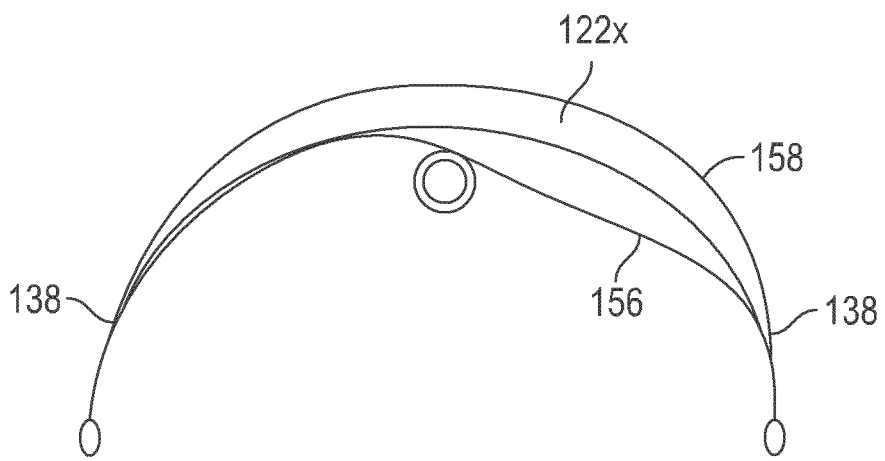
Figure 3L:
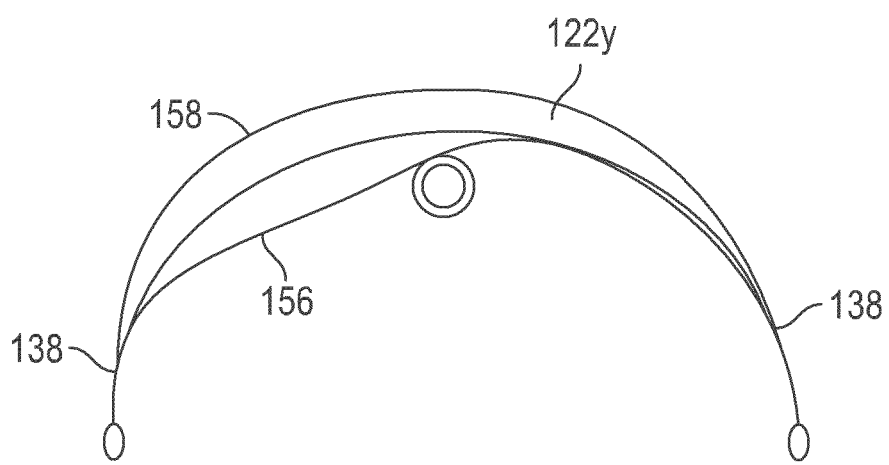
Figure 3M:
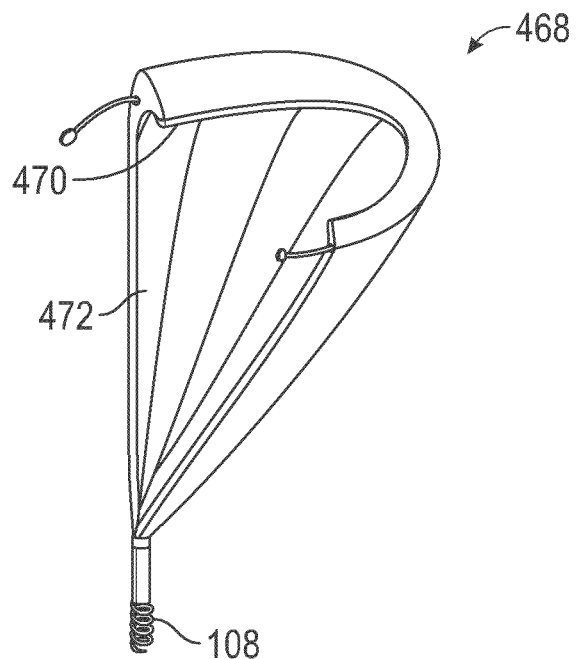
Figure 3N:
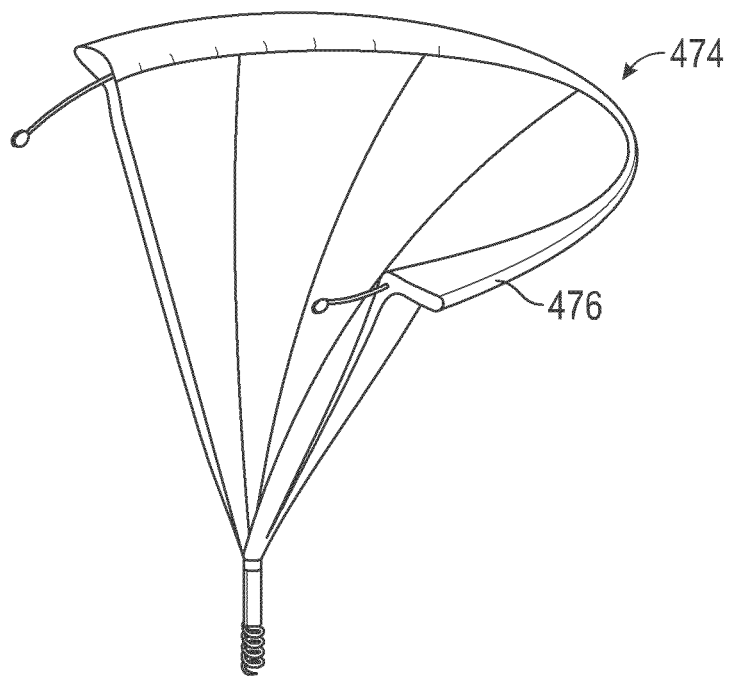
Figure 3O:
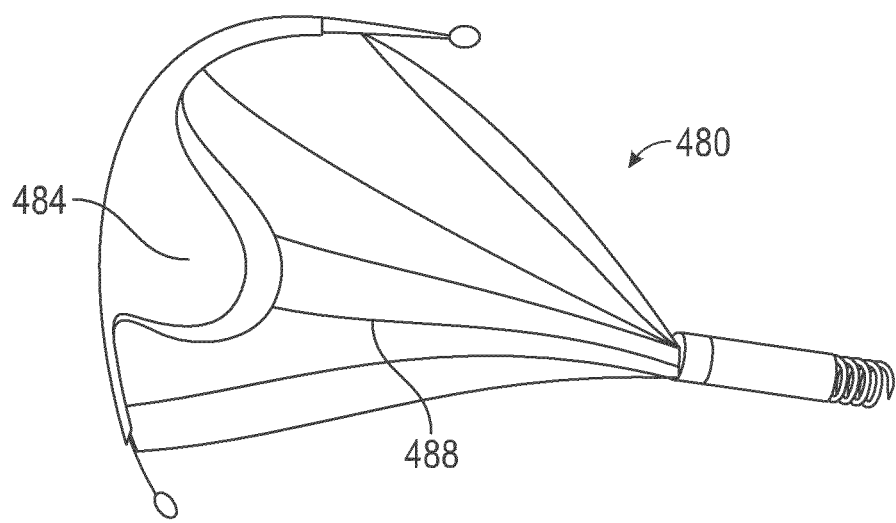
Figure 3P:
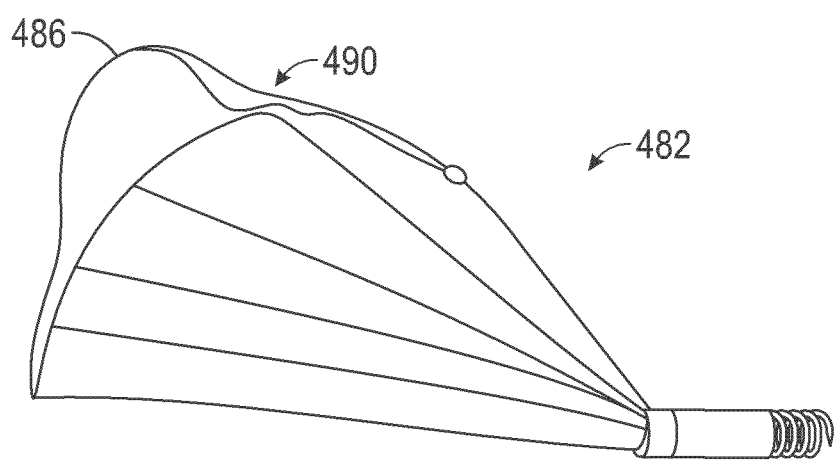

Referring now to FIGS. 3J-3L, the alternative geometries of the valve bodies 122, 122a, 122b, . . . may include differing localized variations in thickness 154 between major surfaces 156, 158. Mitral valve regurgitation may be localized, for example, with a large amount of malcoaptation between valve leaflet segments A1/P1 (see FIG. 1B) so that a relatively thick valve body would be advantageous in those areas, while the coaptation zone along the interface between segments A2/P2 and A3/P3 would not benefit from as thick a valve body (and for which too thick of a valve body may even be deleterious). Valve bodies 122, 122x, 122y . . . have variations in thickness 154 between lateral edges 13 8, and selection of an appropriate one of these differing geometries will enhance coaptation. Advantageously, if a first valve body does not provide effective sealing along one or more leaflet segments when initially deployed, that valve body may be removed and replaced with an alternative valve body having greater thickness at those segments, generally without having to alter a position of initially deployed anchors adjacent the valve annulus.

Figure 3Q:
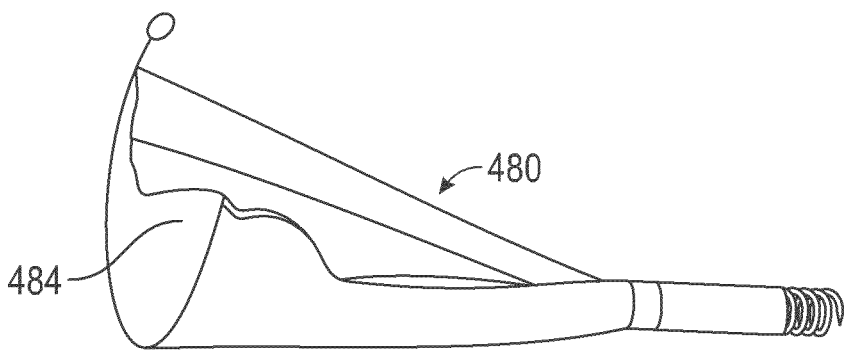

Referring now to FIGS. 3M-3Q, still further alternative geometries of the valve body can be seen, with the valve bodies here having differing flanges along an atrial portion of one or both of the coaptation surfaces so as to mitigate prolapse. In the valve body embodiment 468 of FIG. 3M, a fold or flange 470 protrudes laterally from an adjacent concave coaptation surface 472 so as to axially engage an atrial portion of an anterior facing leaflet. The engagement between flange 470 and the leaflet may help configure the leaflet and/or valve body, enhancing sealing of the valve. Valve body embodiment 474 of FIG. 3N has a protruding fold or flange on a concave or posterior facing side, which may help mitigate prolapse of the other leaflet. Still further coaptation assist bodies may have flanges or folds that are localized along a lateral portion of their widths, with the localized lip being configured to inhibit upward prolapse of one or more of the leaflet segments. For example, in the embodiments of FIGS. 3O and 3P, valve bodies 480 and 482 have localized lips 484 and 486 protruding from their concave coaptation surface 488 and convex coaptation surface 490, respectively, with FIG. 3Q showing a cross-section of the valve body 480 a shape of lip 484.

Figure 4A:
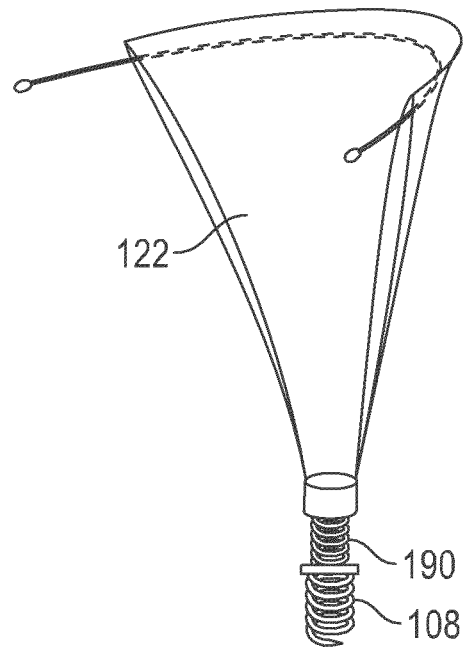
FIGS. 4A-4C schematically illustrate alternative interface structures for mounting coaptation assist bodies to tissues of the heart.
Figure 4B:
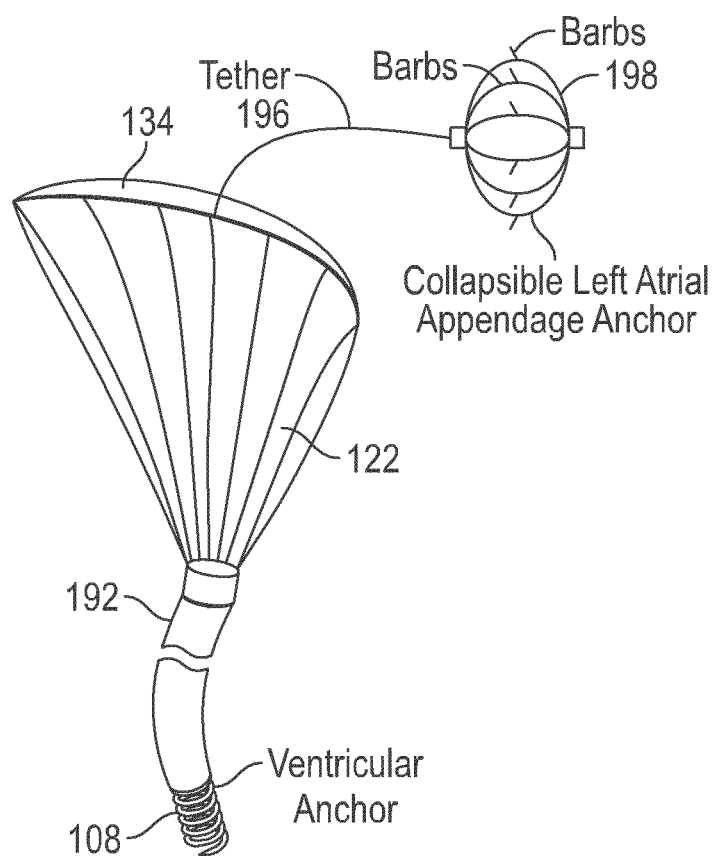

Referring now to FIGS. 4A and 4B, a variety of alternative or modified support interfaces structures may be employed to transfer loads between the valve body and the surrounding tissues of the heart. For example, in FIG. 4A, valve body 122 is coupled to ventricle anchor 108 by an axially resilient spring 190, so that the spring can help accommodate relative axial motion between the anchors adjacent the valve annulus and the more apically disposed ventricular anchor. In FIG. 4B, valve body 122 is axially supported by the ventricular anchor 108 via a laterally flexible filament or tether 192. An atrial tether 196 may support atrial end 134 of the valve body, with the atrial tether in turn optionally being supported by a left atrial appendage anchor 198. Left atrial appendage anchor 198 may optionally comprise a radially expandable body having barbs, so that the anchor can be expanded into affixed engagement with the left atrial appendage of the heart.

Figure 4C:
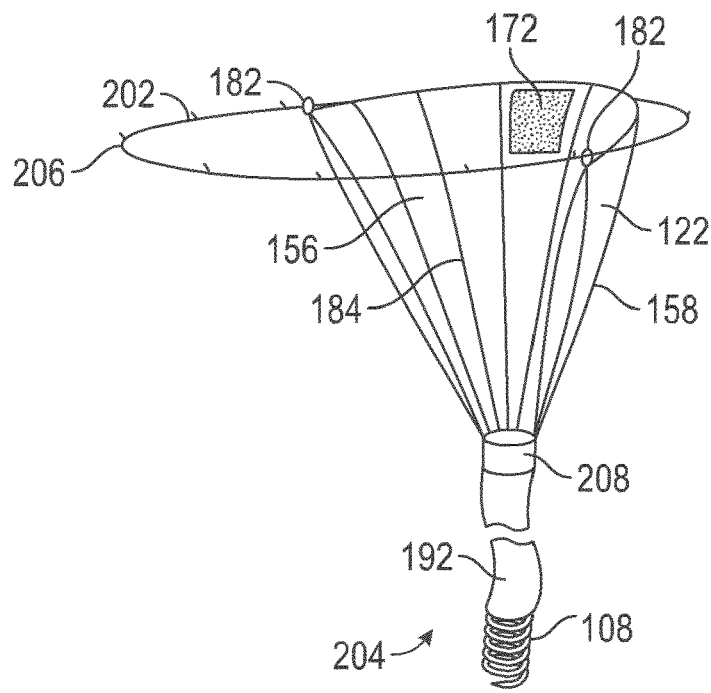
Figure 4D:
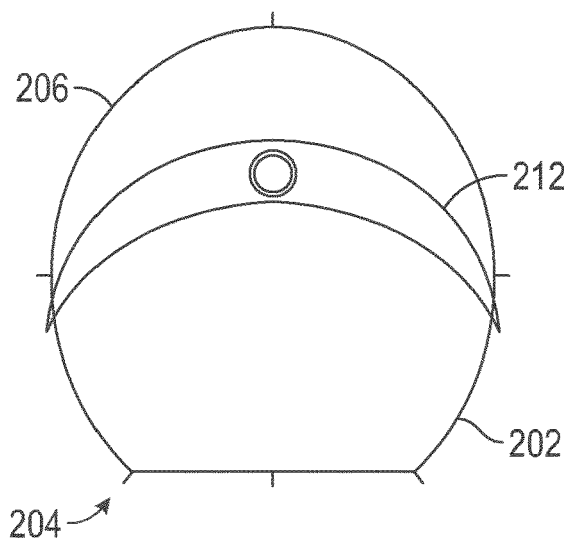
FIGS. 4D and 4E schematically show an axial or end view of an implant having an arcuate base and the same implant compressed for insertion into a delivery catheter.
Figure 4E:
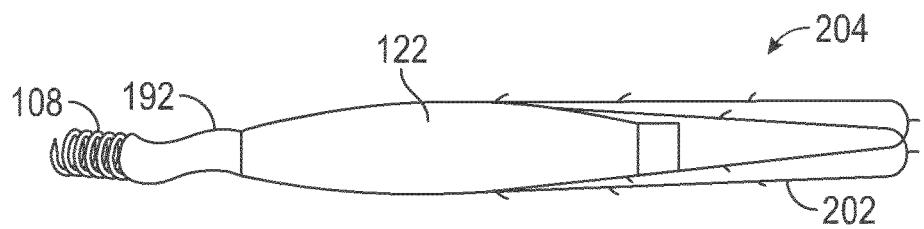

Still further alternative or additional anchor structures and structural interface approaches may be employed. An arcuate support base 202 may be configured to extend along the annulus of the valve for alternative implant 204 as shown in FIGS. 4C-4E. Base 202 has a plurality of tissue penetrating barbs 206 to penetrate tissue and affix the base relative to the valve annulus. Connectors 182 may slidingly couple valve body 122 to base 202. The exemplary arcuate base structure can be compressed within a lumen of a delivery catheter as shown in FIG. 4E, with the arcuate base preferably extending axially of at least a portion of the valve body. As with the other embodiments described herein, a hub may optionally couple valve body 122 with anchor 108 (in some embodiments via a tether 192 or spring, in other embodiments with the hub affixing the anchor relative to the adjacent valve body before, during, and/or after deployment). When the ventricular anchor comprises a helix, the anchor may be rotatable with respect to the valve body, with the hub allowing relative rotation between the anchor and valve body during deployment. The hub may comprise a suture or ePTFE tube.

The coaptation assistance devices described herein are often configured for transvascular delivery and/or deployment via minimally invasive surgery (e.g. thoracotomy, transapical, via the left atrial appendage (LAA), or the like), with delivery and placement preferably being in between or adjacent to the cardiac valve's native leaflets. In particular, the valve can be one of the AV valves such as the tricuspid valve and/or the mitral valve. The drawings and exemplary embodiments largely relate to the mitral valve, but analogous methods and devices can be applied to the tricuspid valve. The coaptation assistance body of the implant can often be delivered by a delivery catheter and may be capable of expanding from a smaller profile to a larger profile to dimensions appropriate for placement in between the valve's native leaflets. In some embodiments, the implants may also find applications for treatment of nonnative valve leaflets (for example, after valve replacement) or for treatment after the native leaflets have previously been surgically modified.

The leaflet-apposing valve body element may comprise self expandable materials such as medical grade polyurethane foam and may be covered with a material such as ePTFE. The valve body may optionally include or be affixed to (or otherwise mountable on) a self expandable frame, with the frame optionally comprising a plurality of members including resiliently (including super-elastically) deformable materials such as a Nitinol alloy. Other frame materials may include stainless steel, plastics, etc. Other materials for the covering include polyurethanes, biologic tissue such as porcine pericardium, silicone, etc. In other embodiments, the leaflet-apposing valve body element may comprise a self-expandable structure such as a Nitinol alloy frame and covered with biocompatible material such as ePTFE. In yet other embodiments the leaflet-apposing element and/or the support interfaces may comprise a braided structure appropriately shaped and covered with ePTFE to fill the gap between the incompetent (mal-coapting) leaflets.

The entire implant and/or valve body, or portions thereof, may incorporate a radiopaque material or an echo-enhancement material for better visualization. The leaflet-apposing valve body element may have a symmetrical or asymmetrical cross section to create an optimal coaptation surface, with the cross-section preferably corresponding to (and/or depending on) the anatomy of the leaflets and their mal-coaptation. The leaflet apposing valve body element may include a curve biased toward a prolapsing leaflet to provide structural support for the prolapsing leaflet and inhibit prolapsing of the leaflet so as to mitigate mal-coaptation. The leaflet apposing valve body element may be printed with a radio-opaque material such as radio-opaque ink. Any support structures of the valve body or support interface having a frame may be coated with radio-opaque materials such as gold or platinum or impregnated with barium. The leaflet apposing valve body element may be coated with an echo enhancement material.

The coaptation assistance device or implant may include one or a plurality of atrial anchors to stabilize the device and/or a ventricular anchor, with the anchors optionally providing redundant fixation. The atrial anchor or anchors may attach to or adjacent the annulus. The annular anchor, if it is included, may be covered with biocompatible materials such as ePTFE to promote endothelialization and, optionally, chronic tissue in-growth or encapsulation of the annular anchor for additional stability. Furthermore the annular anchor may include a plurality of barbs for acute fixation to the surrounding tissue. In other embodiments, the atrial anchors may comprise a plurality of helixes, clips, harpoon or barb-shaped anchors, or the like, appropriate for screwing or engaging into the annulus of the mitral valve, tissues of the ventricle, and/or other tissues of the atrium, or the atrial or ventricular anchors may attach to the tissue by welding using RF energy delivered via the elongate anchor coupling body 110. The ventricular anchor may comprise a helix rotatable with respect to the leaflet apposing element and connected to the hub of the leaflet apposing element by a suture or ePTFE tube. In some embodiments, a ventricular anchor may be included in the form of a tether or other attachment means extending from the valve body thru the ventricle septum to the right ventricle, or thru the apex into the epicardium or pericardium, which may be secured from outside the heart in and combined endo/epi procedure. When helical anchors are used, they may comprise bio-inert materials such as Platinum/Ir, a Nitinol alloy, and/or stainless steel. As noted above, in some embodiments, an atrial anchor in the form of an expandable structure for placement in the left atrial appendage may be included. In still further embodiments, an atrial anchor and support interface may be included in the form of a flexible line or tether attached to an atrial septal anchor. The atrial septal anchor may be configured like a transseptal closure device, optionally using structures that are well known. Any left atrial appendage anchor or atrial septal anchor may be covered with a biocompatible material such as ePTFE, silicone, Dacron, or biologic tissue, or fixed in place using RF welding. A left atrial appendage anchor or atrial septal anchor may be connected to the leaflet apposing valve body element with suture, or ePTFE tube, or may comprise a pre-shaped and rigid or resilient material such as a Nitinol alloy.

The delivery system may include a delivery catheter, with exemplary delivery catheters comprising a variable stiffness shaft with at least one through lumen, the shaft configured for deflecting along at least a distal section. The delivery catheter may further include a control handle to manipulate the device anchors and to manipulate the docking and undocking of the device with the delivery catheter. The control handle may further include flush, irrigation and aspiration ports to remove the air from the system and allow injection of fluids such as saline or contrast media to the site of implantation. The delivery system may also include at least one torque shaft or other elongate anchor coupling body for manipulating the device anchors, initially deploying and recapturing of the anchors to and from the delivery catheter, and guiding the valve body distally to one or more of the initially deployed anchors.

The delivery system may also include an outer sheath or introducer, typically to allow the introduction of the delivery catheter through a lumen of the outer sheath and into the left atrium, so that the outer sheath functions as a trans septal sheath. The transseptal sheath may include a variable stiffness outer shaft with at least one lumen, the lumen sized to allow insertion of the delivery catheter and/or coaptation assistance body through the sheath lumen. A deflectable distal section of the trans septal sheath may facilitate alignment of the coaptation assistance device with the valve leaflets.

A conductive surface of the catheter system and/or implant may be coupled by a conductor to a proximal end of the delivery system so as to allow the conductive surface to act as an electrode, for example, to help to detect the location and/or deployment characteristics of an implant. The transseptal catheter and/or delivery catheter may include at least one electrode at the distal tip configured to be connected to an intracardiac electrogram sensing and/or recording system. In some embodiments, an electrogram may be sensed from the anchor 108, providing an electrogram signal that can be transmitted along the elongate anchor coupling body 110. Anchor coupling body 110 can be coupled with an appropriate electrogram recording system. Unipolar electrogram signals sensed at the electrode on the distal end or the delivery catheter, a unipolar electrogram sensed at the anchor 108, and/or a bipolar electrogram recorded between the delivery catheter electrode and the anchor, can be used to evaluate candidate locations for deployment of the anchor or other implant components. In particular the annulus of the valve may be detected by an appropriate ratio of atrial electrogram signals to ventricular electrogram signals at a candidate location. Once a signal ratio in a desired range has been identified (for example, with a ratio of about 1:2), the information from the signal may be combined with imaging information showing that the candidate location is near a commissure of the annulus, and in response, the candidate sight may be selected as an anchoring site for an associated atrial anchor.

Referring now to FIGS. 5A-5L, exemplary method steps which may be included in embodiments of methods for treatment of mitral valve regurgitation associated with malcoaptation can be understood. Note that related method steps may also be used for other indications and/or for therapies of other valves. Prior to treatment (and optionally again during and/or after treatment), surgical staff may evaluate the anatomy of the heart and/or the components thereof (including the mitral valve), and may chose an appropriate configured implant. The evaluation can include x-ray, CT, MRI, and 2d or 3d echocardiography, and the like.

Figure 5A:
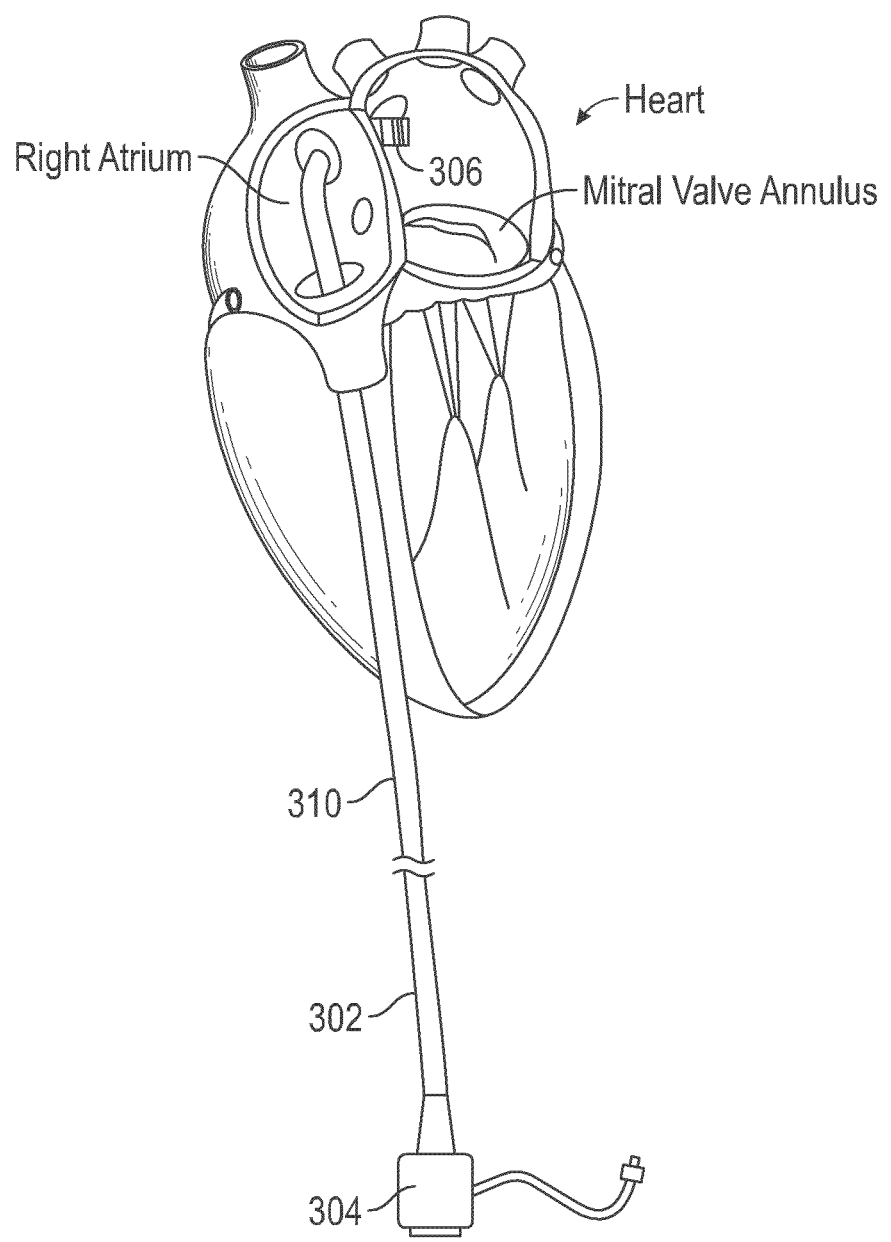
FIGS. 5A-5L schematically illustrate exemplary method steps for deploying implants into the heart so as to mitigate mal-coaptation.

Referring first to FIG. 5A, a transseptal method for treatment of MR will often include gaining access to the left atrium LA via a transseptal sheath 300. Access to the femoral vein may be obtained using the Seldinger technique. From the femoral vein, access can then be obtained via the right atrium to the left atrium by a trans septal procedure. A variety of conventional trans septal access techniques and structures may be employed, so that the various imaging, guidewire advancement, septal penetration, and contrast injection or other positioning verification steps need not be detailed herein. Exemplary steerable transseptal sheath 300 has an elongate outer sheath body 302 extending between a proximal handle 304 to a distal end 306, with the handle having an actuator for steering a distal segment of the sheath body similar to that described above regarding deployment catheter 100. A distal electrode and/or marker near the distal end 306 of sheath body 302 can help position the sheath within the left atrium. In some embodiments, an appropriately sized deflectable trans septal sheath without steering capability 310 may be guided into position in the left atrium by transseptal sheath 300 (see FIG. 5B) or may be advanced into the left atrium without use of a steerable transseptal sheath. Alternatively, deployment may proceed through a lumen of the steerable sheath 300. Regardless, an outer access sheath will preferably be positioned so as to provide access to the left atrium LA via a sheath lumen.

Figure 5B:
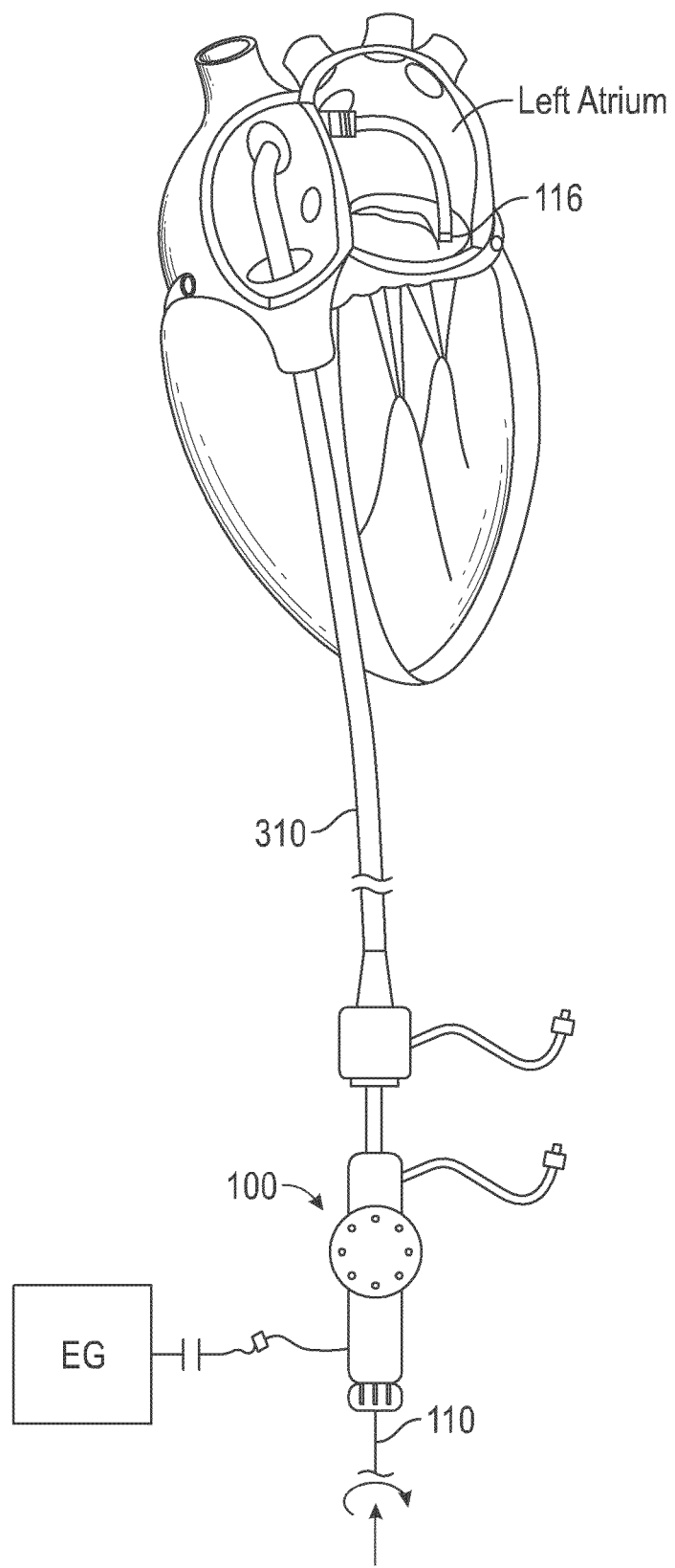
Figure 5C:
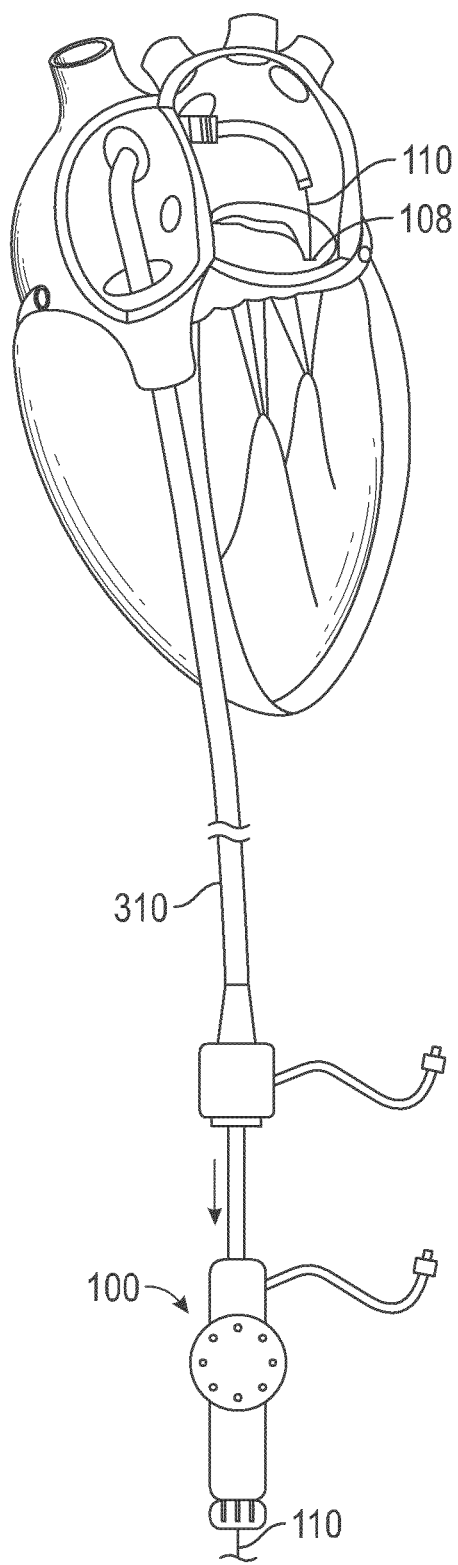
Figure 5D:
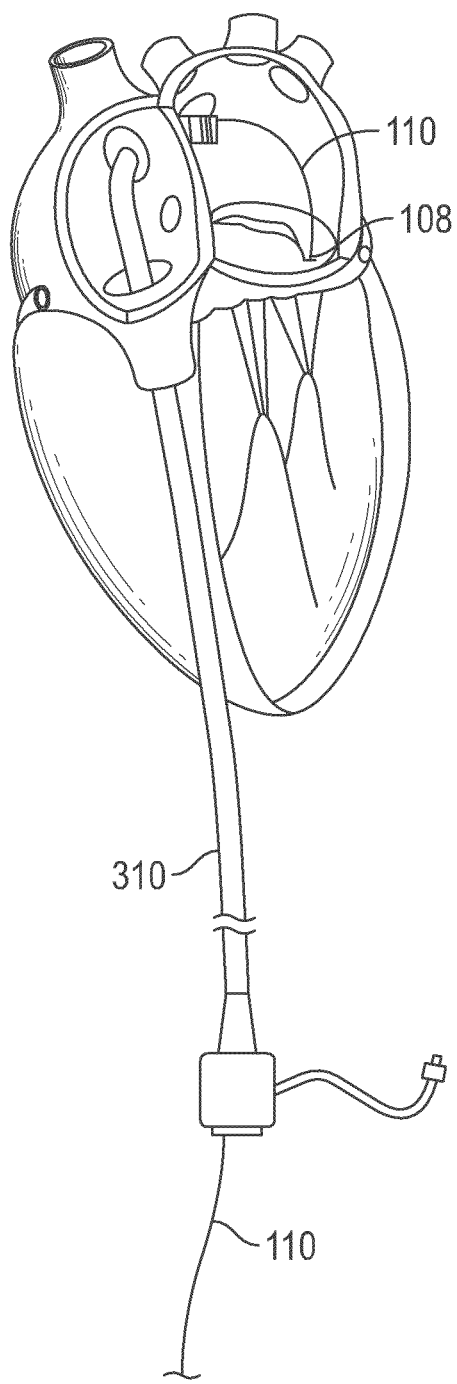

Referring now to FIG. 5B, deployment catheter 100 is advanced through the outer trans septal sheath and into the left atrium. The distal end of the deployment catheter moves within the left atrium by manipulating the proximal handle and by articulating the actuator of the handle so as to selectively bend the distal end of the catheter body, bringing the distal end of the catheter into alignment and/or engagement with candidate locations for deployment of an anchor, optionally under guidance of 2D or 3D intracardiac, transthoracic, and/or transesophageal ultrasound imaging, Doppler flow characteristics, fluoroscopic or X-ray imaging, or another imaging modality. Electrode 116 at the distal end of deployment catheter 100 optionally senses electrogram signals and transmits them to an electrogram system EG so as to help determine if the candidate site is suitable, such as by determining that the electrogram signals include a mix of atrial and ventricular components within a desired range (such as within an acceptable threshold of 1:2). Contrast agent or saline may be introduced through the deployment catheter. Before, during, and/or after the deployment catheter is being positioned in engagement with and/or oriented toward an acceptable target location, an anchor 108 is advanced distally through a lumen of the deployment catheter, so that the advanced anchor extends from the positioned catheter and into engagement with tissue of the heart at the target location, with advancement of the anchor preferably being performed using an elongate anchor coupling body 110 and an anchor catheter 404 of anchor deployment assembly 402. An electrogram may be recorded from the anchor 108 via the elongate anchor coupling body 110 to further assist in identifying an acceptable target location.

As can be understood with reference to FIGS. 5B, 5C, and 3I3-3I5 a first atrial anchor 108 is preferably deployed into the mitral valve annulus by axially advancing the anchor and rotating the helical anchor body through the positioned deployment catheter, screwing the helical body penetratingly into the heart tissue using elongate anchor coupling body 110 and anchor catheter 404. Deployment catheter 100 and anchor catheter 404 can then be retracted proximally from deployed anchor 108, leaving the anchor affixed to the tissue and associated elongate anchor coupling body 110 extending proximally from the anchor and out of the body. Note that anchor 108 may remain only initially deployed at this stage, as it can be recaptured, removed, and/or repositioned by torquing the elongate anchor coupling body so as to unscrew the helical anchor body. As can be understood with reference to FIGS. 5B and 5C, deployment catheter 100 can be removed from the outer transseptal sheath 310 leaving elongate anchor coupling body 110 in place (with the deployment catheter also being withdrawn proximally from over the elongate anchor coupling body so that the anchor coupling body is no longer within the deployment catheter lumen, but remains within the outer transseptal sheath lumen). As seen in FIG. 5E, the deployment catheter 110 can then be re-inserted distally through the outer sheath lumen (alongside the elongate anchor coupling body of the deployed anchor) and into the left atrium.

Figure 5E:
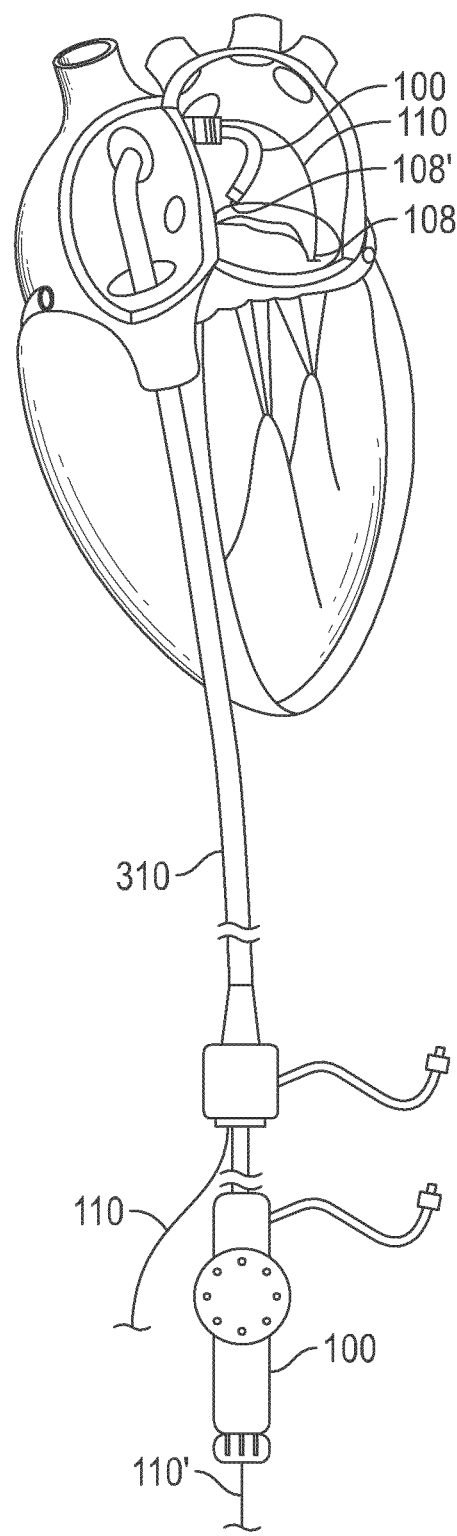
Figure 5F:
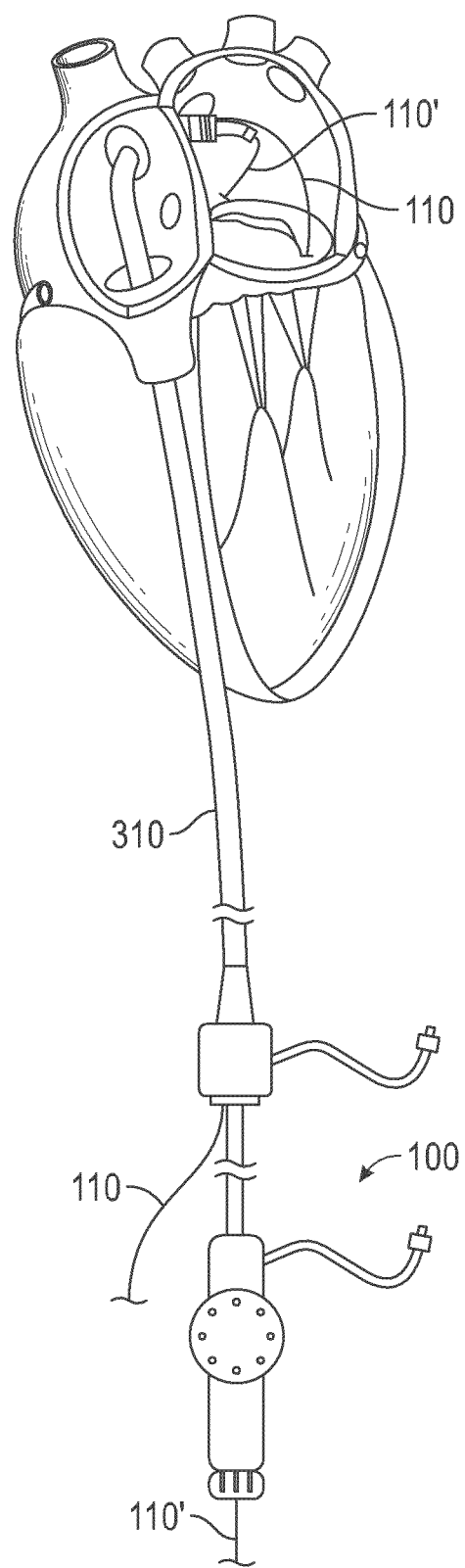
Figure 5G:
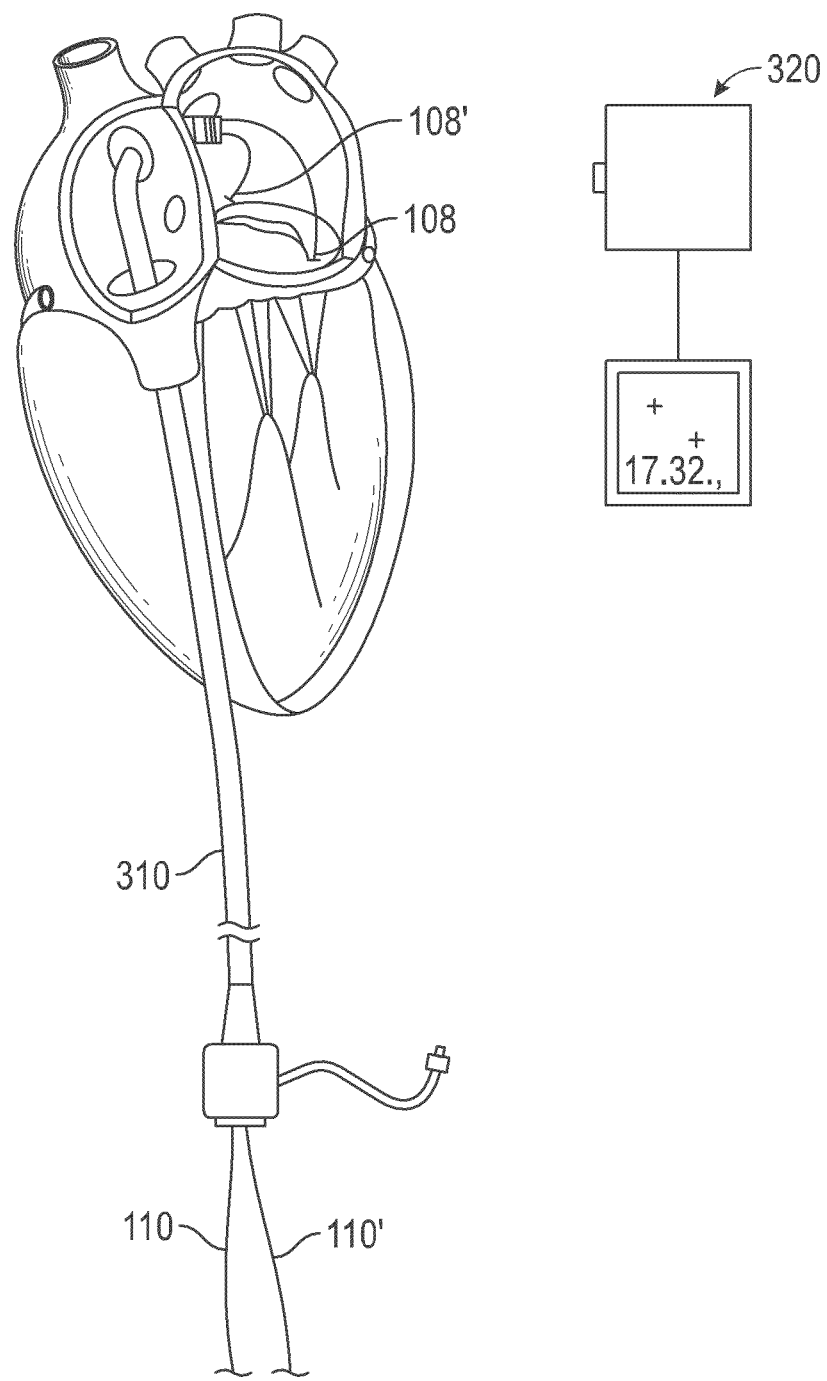

Referring now to FIGS. 5E and 5F, deployment catheter 100 may be manipulated and/or steered so as to engage the tip of the catheter with (and/or orient the tip toward) a second target location. In the exemplary embodiment, the first and second target locations are near the two opposed commissures of the mitral valve. Sensing of electrical signals, remote imaging, tactile indications of tissue structures, and the like can be used for positioning, as generally described above. Once deployment catheter 100 appears to be in place, a second anchor 108' is deployed using a second elongate anchor body 110' and associated anchor catheter. As can be understood with reference to FIGS. 5F and 5G, deployment catheter 100 can be withdrawn proximally over second elongate anchor body 110' and out of outer sheath 310, leaving both anchors 108, 108' deployed and both associated elongate anchor deployment bodies 110, 110' extending from the deployed anchors through the outer sheath so that their proximal ends are outside the body of the patient. Advantageously, anchors 108, 108' can be used as measurement fiducials to facilitate measurement of the valve, valve and/or anchor movement, anchor positioning relative to the valves, and the like using measurement capabilities of a remote imaging system 320. Elongate anchor deployment bodies 110, 110' can also be used to verify anchor deployment and/or to verify anchor sites on the valve annulus by pulling proximally on the deployment bodies, measuring a electrogram signal from an anchor electrode, and/or the like. If desired, one or both atrial anchors can be re-deployed as described above.

Figure 5H:
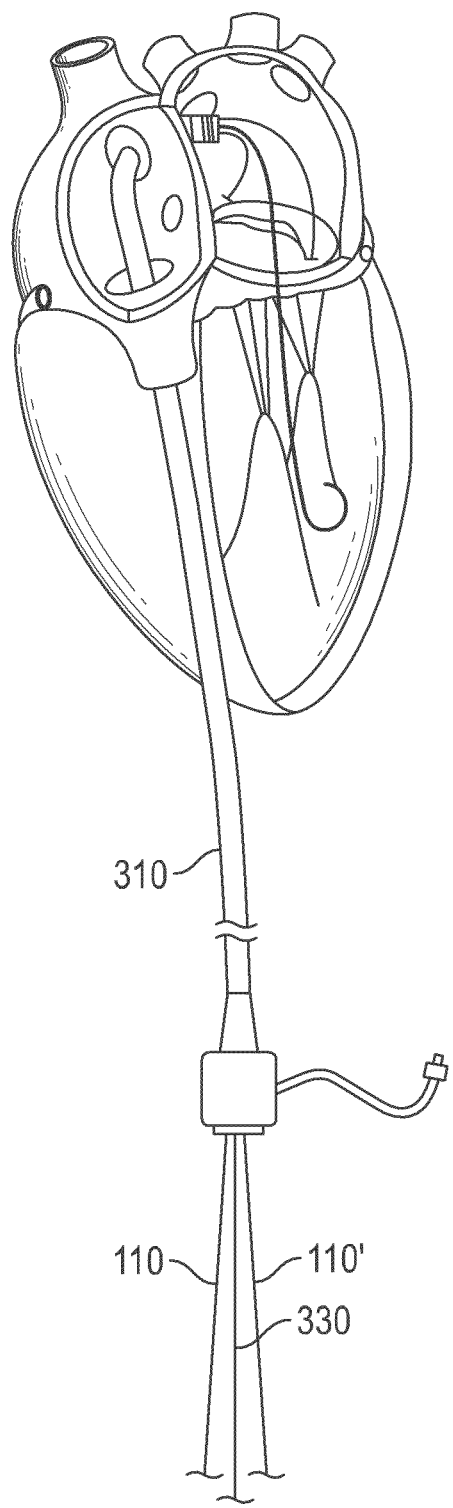
Figure 5I:
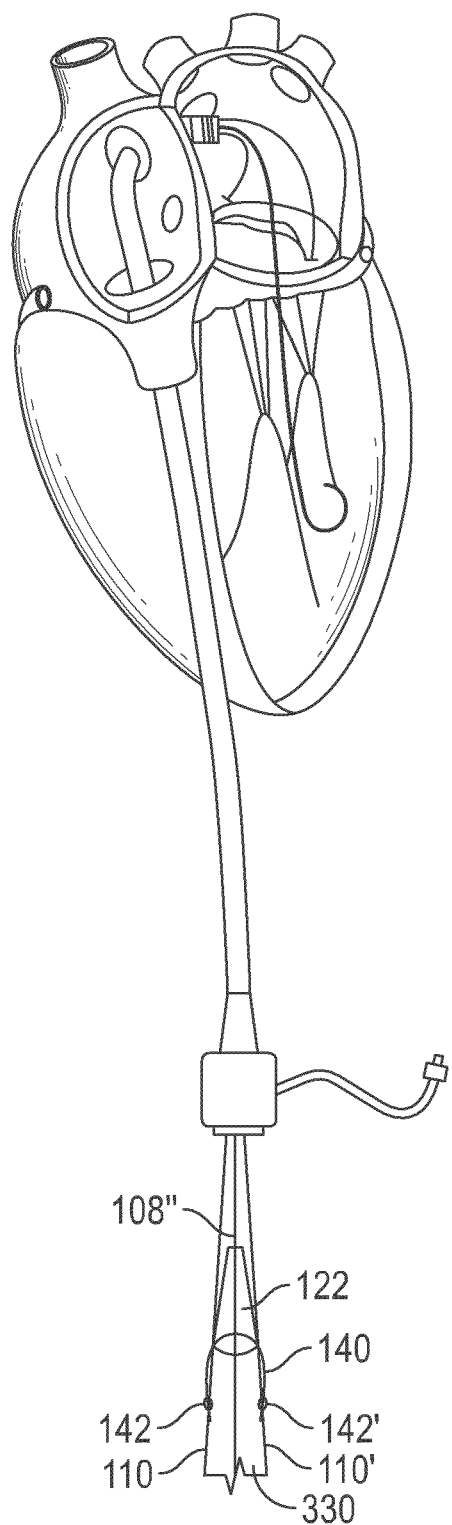

Referring now to FIGS. 5H and 5I, a guidewire 330 is advanced through trans septal sheath 310 into the left atrium. Guidewire 330 crosses the mitral valve and is advanced distally into the left ventricle, as shown in FIG. 5I. Valve body 122 is loaded on guidewire 330, in the exemplary embodiment by passing the guidewire through a helical lumen of helical ventricle anchor 108". Valve body 122 is also loaded onto elongate anchor deployment bodies 110 110' by passing each of the bodies through an associated one of loops or apertures 142, 142' of atrial member 140, so that an orientation of any nominal curvature of valve body 122 corresponds to the curved line defined by a cross-section of the coaptation zone of the mitral valve. Valve body 122 can be inserted into trans septal sheath 310 and advanced into the left atrium. In the exemplary embodiments, valve body 122 is advanced distally by passing elongate guide bodies 110, 110' and guidewire 330 proximally through the lumen of anchor deployment catheter 100 or a separate valve body deployment catheter 340. Valve body deployment catheter 340 is described above with reference to catheter 120 of FIGS. 3C and 3D. Ventricle anchor 108" engages a distal surface at the distal end of deployment catheter 340 so as to allow the deployment catheter to push the ventricle anchor 108" and attached valve body 122 distally into and along the lumen of outer sheath 310, as can be understood with reference to FIGS. 5I and 5J. Loops or apertures 142, 142' slide distally along the elongate anchor deployment bodies 110, 110' as the valve body advances.

Figure 5J:
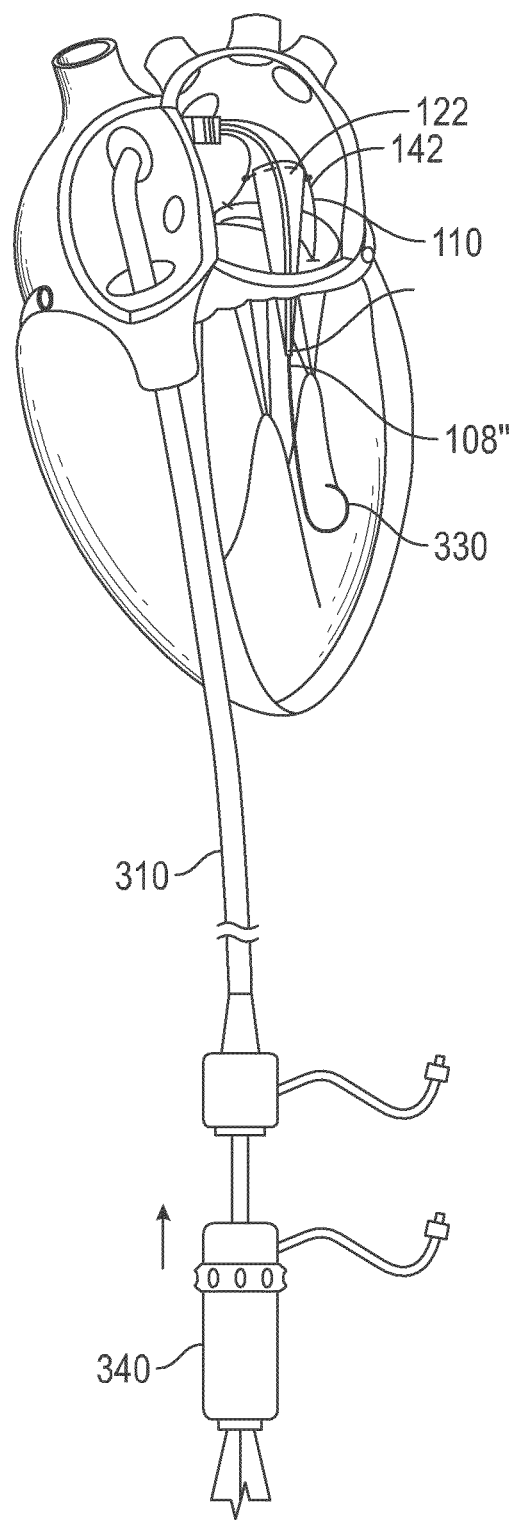
Figure 5K:
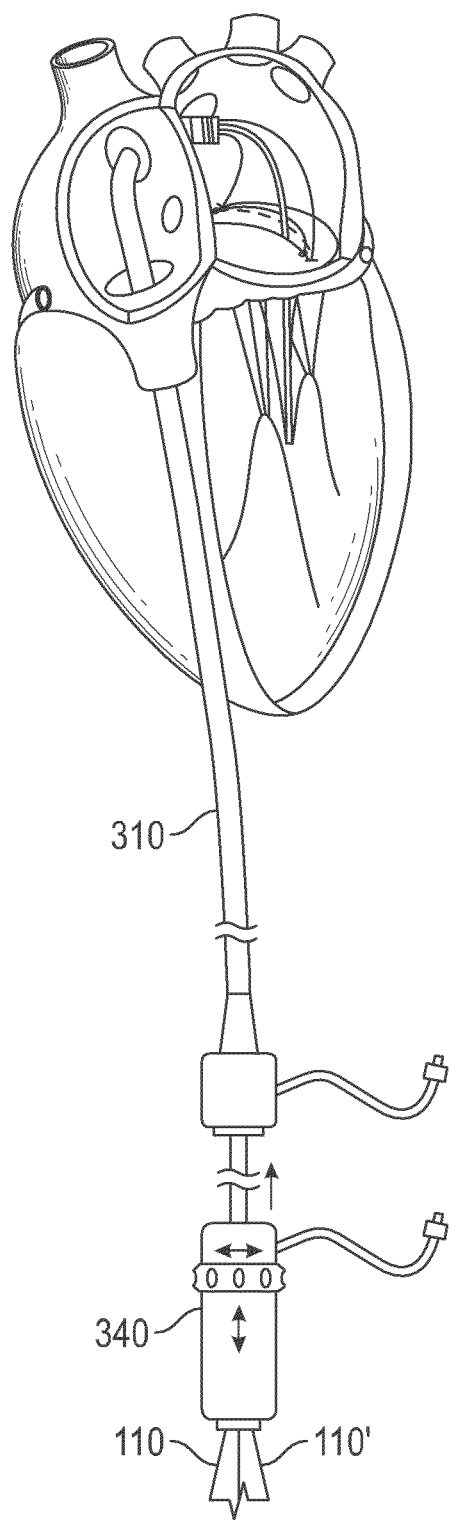
Figure 5L:
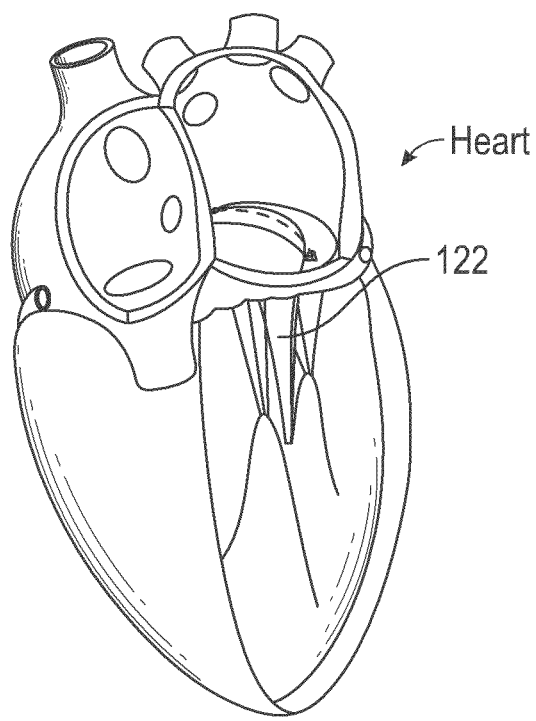

As can be understood with reference to FIGS. 5J and 5K, deployment catheter 340 is manipulated and/or articulated so as to advance valve body 122 distally out of septal sheath 310 and within the left atrium as so that ventricular anchor 108" and distal portion of valve body 122 cross the mitral valve. Catheter 340, guidewire 330, anchor deployment shaft 458 or another torque-transmission shaft may rotationally engage ventricular anchor 108", and a hub between the ventricular anchor and valve body 122 may allow relative rotation about the helical axis as described above. Tension applied by pulling the proximal ends of elongate anchor deployment bodies 110 while advancing deployment catheter 340 brings the anchors into engagement with the remaining components of the structural interface between valve body and the tissues (such as loops or apertures 142 and atrial member 140). The positions of anchors 108, 108' help orient valve body 122 within the valve so that edges 138 are each oriented toward an associated commissure, and so that the leaflets each coapt with an associated major surface 156, 158 of the valve body. A desired amount of axial tension can be applied to valve body 122 by applying a distal load on deployment catheter 340, and the deployment catheter can be manipulated and/or articulated into engagement with a candidate location of the ventricle, optionally between the papillary muscles. The candidate location can be verified as generally described above, and catheter 340 or another torque-transmitting anchor driving shaft can be rotated while maintaining the distal end of ventricle anchor 108" in contact with the target location so that the helical anchor body penetrates into tissue of the ventricle, thereby deploying the valve body. In alternative embodiments, an atraumatic ventricular anchor 460 can be deployed by advancing the anchor and/or withdrawing a surrounding sheath from over the anchor) so that the arms of anchor engage with the highly uneven surface of the ventricular trabeculae, and so that the arms of the anchor are entangled therein sufficiently to restrain the position of the anchor within the ventricle. Note that embodiments of such an anchor need not be configured to penetrate significantly into the ventricular wall (although alternative barbed anchor embodiments can).

Advantageously, hemodynamic performance of the valve with the valve body therein can be evaluated before decoupling one or more of the anchors from the delivery catheter system (and in some embodiments, even before the ventricle anchor is deployed in ventricle tissue). If results are less than desired, one or more of the anchors can be detached from the tissue and retracted back into the transseptal sheath 310, allowing the physician to reposition the anchor and coaptation assistance body. The valve body can be withdrawn proximally via sheath 310 and an alternative valve body selected, loaded into the sheath, and deployed if appropriate. One or more of the atrial and/or ventricular anchors can be redeployed and the surgical staff can again perform a hemodynamic evaluation. In some embodiments, one or more of guidewire 330 and/or elongate anchor deployment bodies 110, 110' may remain coupled to an associated anchor for hours or even days. Once the implant is in the desired deployed configuration, the device may be locked to the elongate anchor deployment bodies or tethers using crimps, or knots, etc., and the excess lengths of these bodies may be cut and removed from the implant. In the exemplary embodiments, crimps 432 can be advanced distally using one or more crimping and cutting assembly 420 or 420' so as to affix the valve body to the deployed atrial anchors, and elongate bodies 110 can be decoupled from the anchors, as can be understood with reference to FIGS. 5K, 5L, and 3I7-3I13. If the deployment is deemed acceptable, after deploying the ventricular anchor and after the implant is released from the catheter system, the surgical staff can remove the remaining catheter system components and elongate anchor deployment bodies.

A full hemodynamic evaluation—e.g. intra cardiac echocardiogram (ICE), trans esophageal echocardiogram (TEE) or transthoracic echocardiogram (TIE) may be performed on the patient after deployment is complete.

Figure 6A:
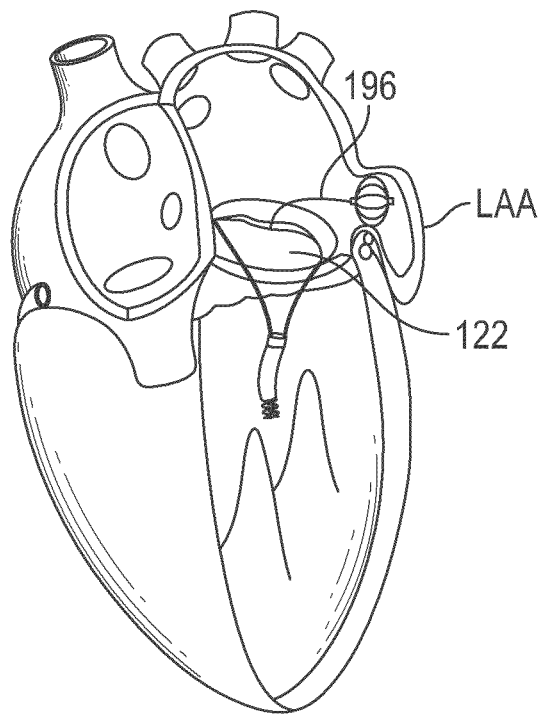
FIGS. 6A-6C schematically illustrate alternative coaptation assist implants and their implantation within a mitral valve.
Figure 6B:
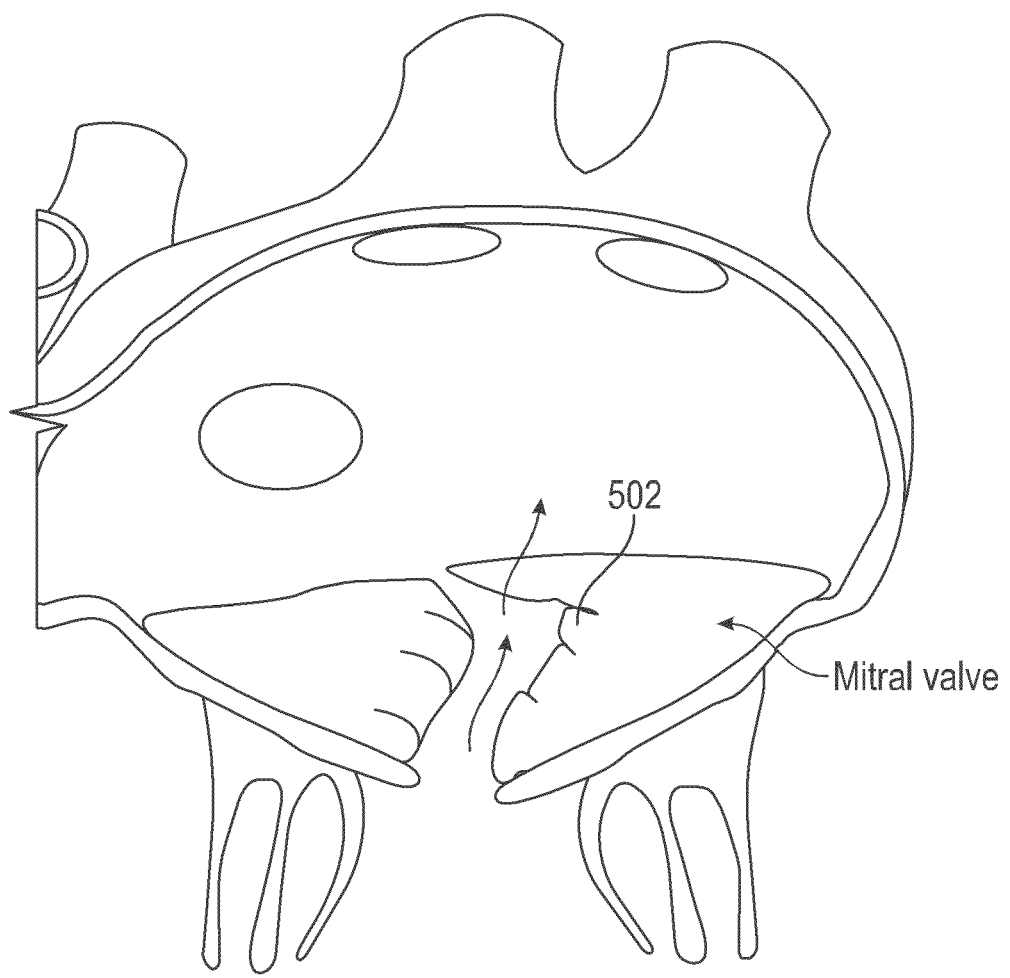
Figure 6C:
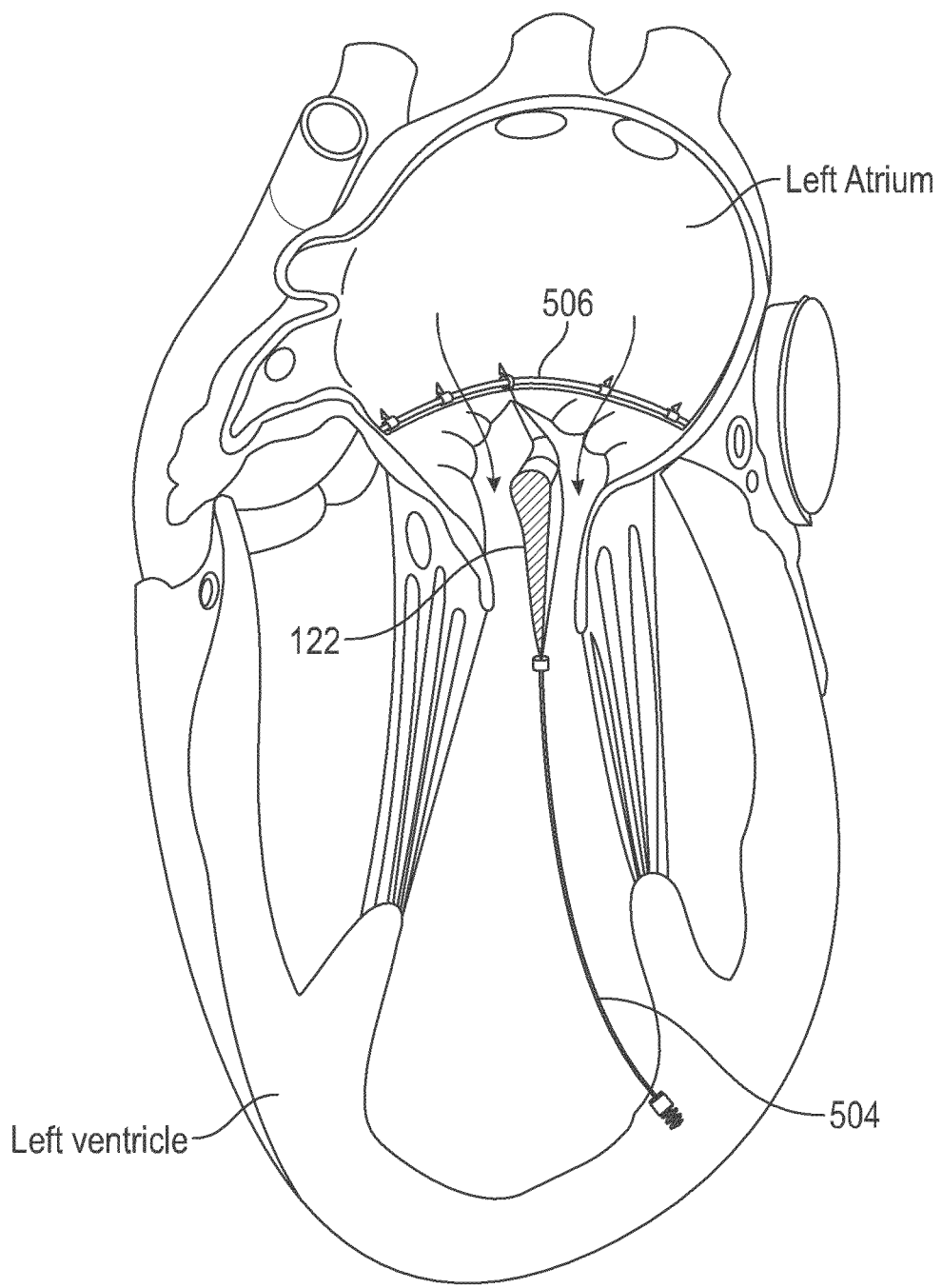
Figure 7A:
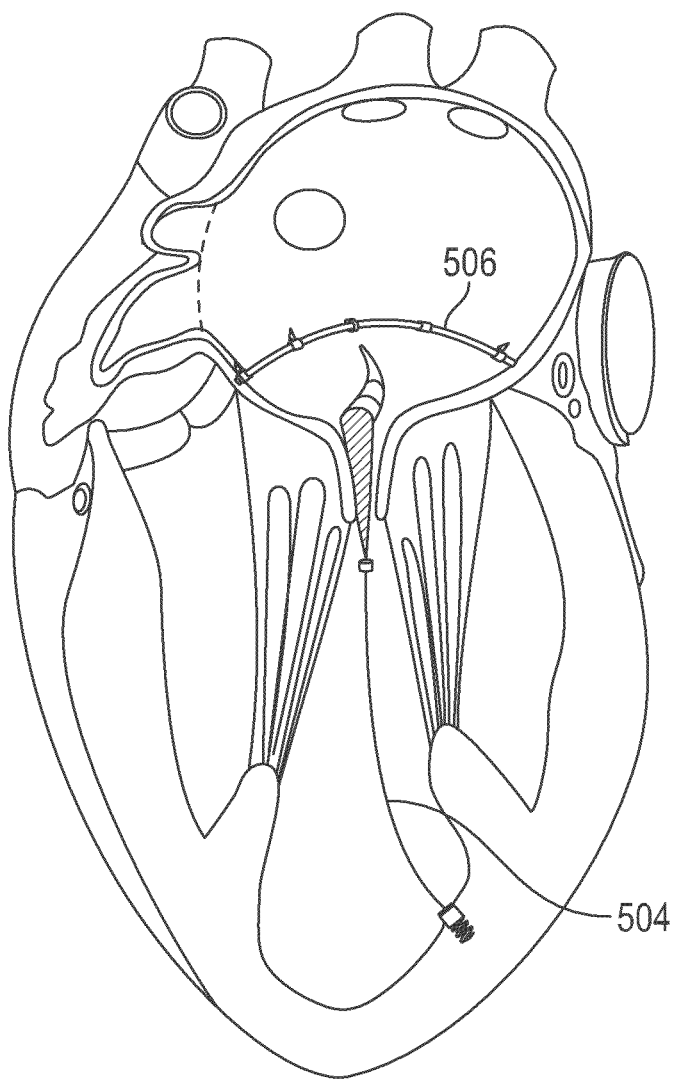
FIGS. 7A and 7B schematically illustrate alternative implant mounting interface structures and methods, and show apposition of the leaflets against a movable and/or deformable coaptation assist body.
Figure 7B:
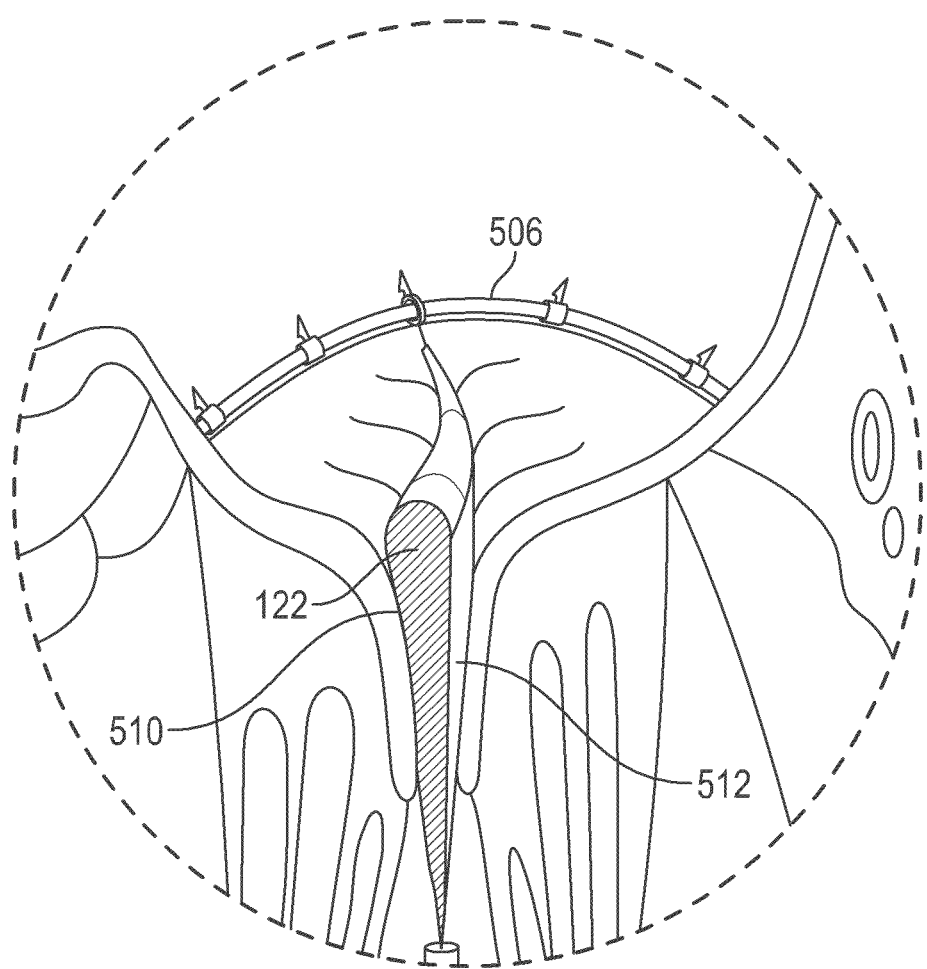

Referring now to FIGS. 6A-7B, a variety of alternative support structures might be employed so as to help maintain a position and/or orientation of valve body 122, with or without anchors 108 or 260. For example, implant embodiments similar to that described above regarding FIG. 4B may include an atrial support tether 196 configured to help axially support valve body 122, with the tether optionally being affixed to tissue of the left atrial appendage LAA using an expandable left atrial appendage anchor 198, as seen in FIG. 6A. Leaflet prolapse or other forms of mal-coaptation 502 of the mitral valve MV may be mitigated by supporting valve body between the leaflets, optionally using a ventricular tether 504 anchored near a ventricular apex of left ventricle LV and/or an arcuate support structure 506 disposed along the annulus of the valve, as can be understood with reference to FIGS. 6B-7B. Prior to deployment of the implant, mal-coaptation leads to mitral regurgitation during ventricular systole, but does not significantly impede free flow of blood from the atrium into the ventricle during diastole, particularly when the cross-section of the implant remains substantially aligned along the flow of blood. As can be understood by comparing FIGS. 6C and 7A, the shape of the ventricle and/or annulus may change significantly during each heart cycle, so that arcuate anchor 506 and ventricular tether 504 may flex significantly during each heart beat. Implant life can be impacted by such flexing, which should be considered when selecting an appropriate anchor system. As can be understood with reference to FIGS. 6B and 7B first and second coaptation zones 510,512 between each leaflet of the valve and valve body 122 may be slightly (or even significantly) axially offset from each other, particularly when the implant is used to treat mal-coaptation related to prolapse of one leaflet.

Additional aspects of the present invention can be understood with reference to FIGS. 8A-8F. FIG. 8A shows a prototype triangular valve body formed from a uniform sheet of ePTFE, along with atrial and ventricular anchors. Sliding engagement between the valve body and an atrial member, and between loops or apertures of the atrial member and elongate deployment bodies of the atrial anchors can be seen in FIGS. 8B and 8F. Passing of a ventricular guidewire through a helical lumen of the helical anchor is shown in FIG. 8C, and the anchors and some of the deployment system components which interact therewith can be seen in FIG. 8D. FIG. 8E shows an expanded configuration of the valve body and the anchor deployment structures as the valve body is advanced out of a transseptal sheath.

Still further aspects of the present invention can be understood with reference to FIGS. 9-13. The embodiments of FIGS. 9-13 may provide additional adjustability of the valve body, so that the valve body can be adapted to a patient's particular physiology, and may provide additional improvement in the treatment of mal-coaptation. FIG. 9 shows a coaptation device 900 in accordance with embodiments. Coaptation device 900 is introducible into the heart and coupleable in vivo within the heart valve to be treated, in a manner similar to that described above. Coaptation device 900 includes a coaptation assist body 901, which further includes a first major coaptation surface 902, and a second major coaptation surface not visible in FIG. 9. Coaptation assist body 901 has an axis, for example a longitudinal axis generally running from an upstream end 903 to a downstream end of coaptation assist body 901. Other axes may be defined, for example a transverse axis. Example coaptation assist body 901 also defines an axial channel 904, and a tether 905 is disposed within channel 904. Tether 905 may be a wire or suture, or may be made of another suitable material, and is preferably coupled to coaptation assist body 901 at downstream end 903.

Figures 10A, 10B:
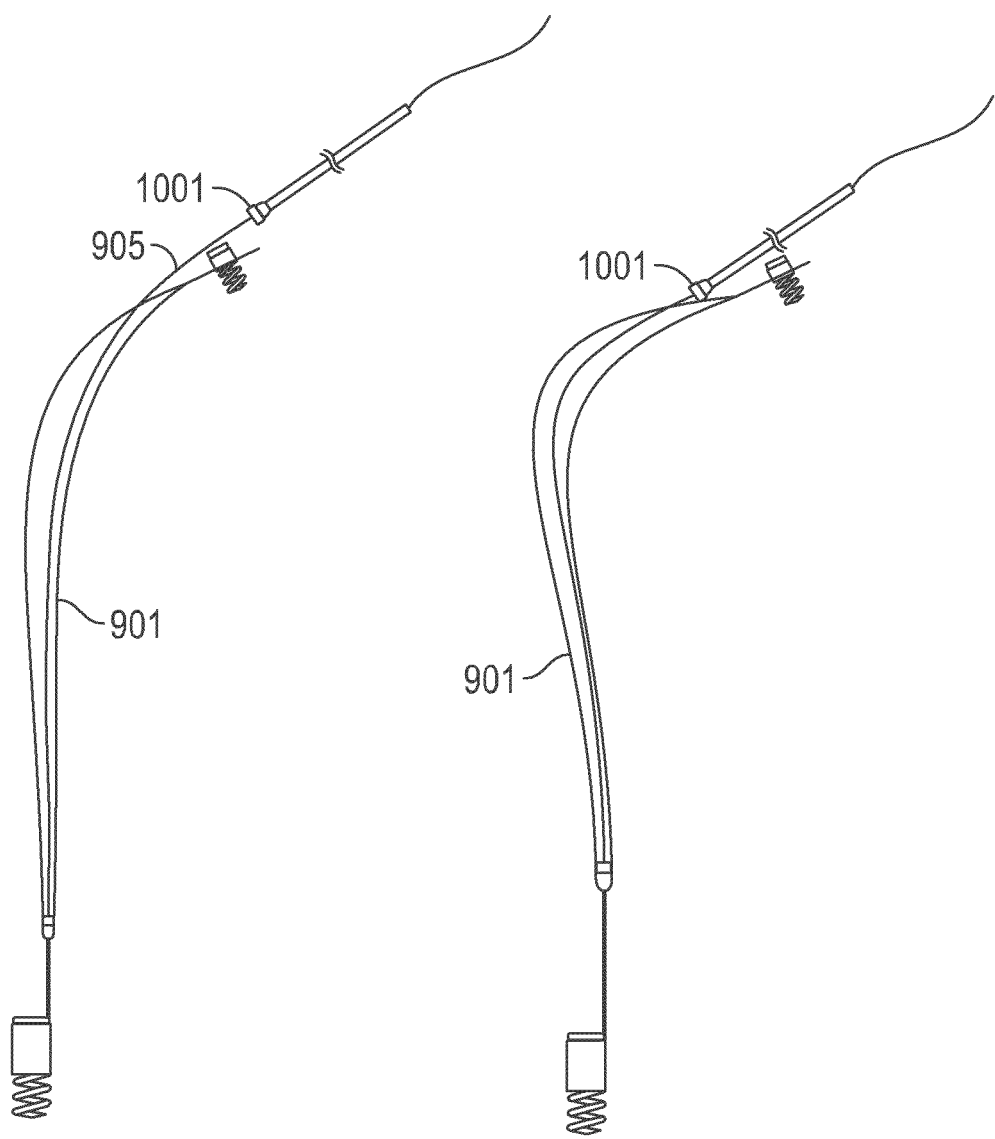
FIGS. 10A and 10B show a coaptation assist body in relaxed and curved positions respectively, in accordance with embodiments.
Figure 11:
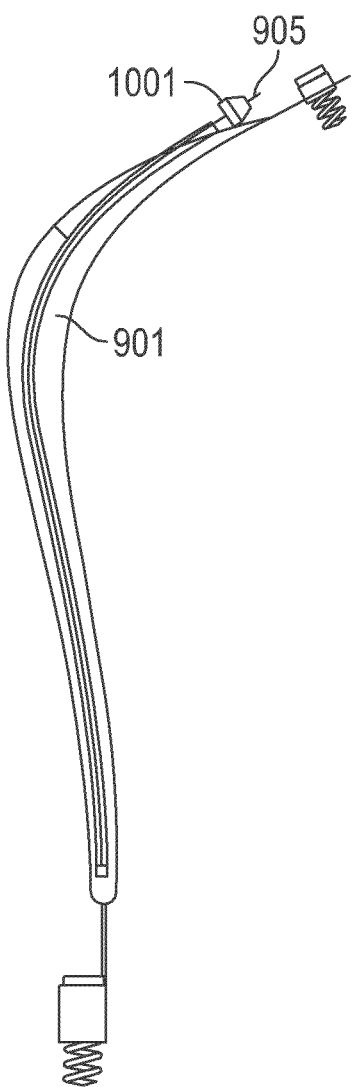
FIG. 11 shows the coaptation device of FIG. 9 after deployment.

As is visible FIGS. 10A and 10B, channel 904 and tether 905 are preferably positioned asymmetrically or eccentrically within coaptation assist body 901, that is, not coincident with the neutral bending axis of coaptation assist body 901, such that as the length of tether 905 within coaptation assist body 901 is varied, the curvature of coaptation assist body 901 changes. For example, FIG. 10A shows coaptation assist body 901 in a relaxed position, and FIG. 10B shows coaptation assist body 901 is a more curved position. A curvature lock 1001 is disposed at the one end (in this case upstream end 902) of coaptation assist body 901. In the example shown, curvature lock 1001 is a crimp that can be crimped onto tether 905, to lock tether 905 such that the distance between ends 902 and 903 of coaptation assist body 901 is constrained, to define a curvature of coaptation assist body 901. Once curvature lock 1001 is engaged and tether 905 is locked, tether 905 may be cut and the unused portion removed, as shown in FIG. 11.

Referring again to FIG. 9, coaptation assist device 900 may include various anchors for anchoring coaptation assist device 900 within the heart valve. A central atrial anchor 906 may be deployable to anchor coaptation assist body 901 near upstream end 902, for example to the annulus of the heart valve in the atrium of the heart. One or more lateral atrial anchors 907*a*, 907*b* may be affixed near the lateral edges of upstream end 902 of coaptation assist body 901, and may be deployable to fix upstream end 902 to the heart near respective commissures of the heart valve. A ventricular anchor 908 may be affixed near downstream end 903, and may be deployable to fix downstream end 903 to ventricular tissue of the heart.

Figure 12A:
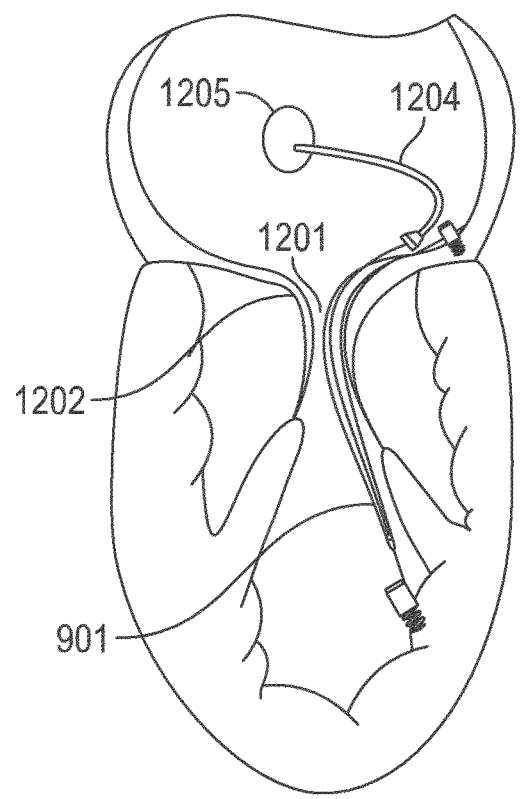
FIGS. 12A and 12B show an effect of the adjustment of the curvature of the coaptation assist body of FIG. 9.
Figure 12B:
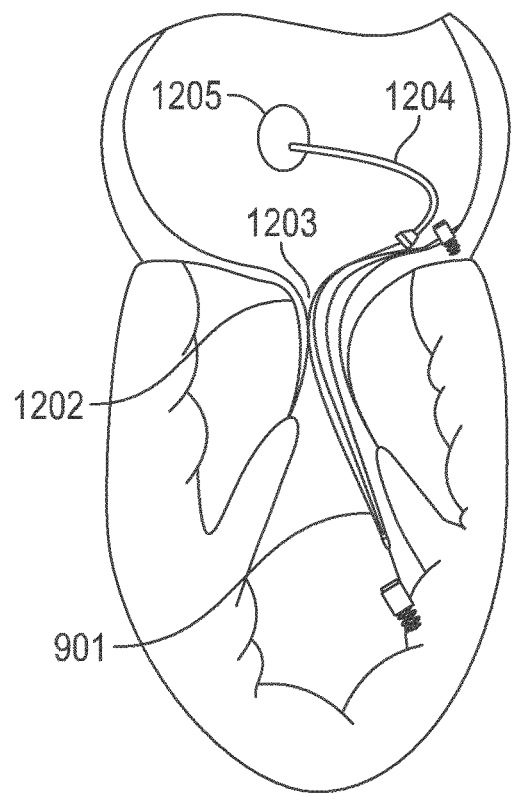

An effect of the adjustment of the curvature of coaptation assist body 901 is shown in FIGS. 12A and 12B. In FIG. 12A, insufficient curvature has been introduced, and an opening 1201 exists between coaptation assist body 901 and valve leaflet 1202, such that valve regurgitation may still occur. In FIG. 12B, more curvature has been introduced such that valve leaflet 1202 contacts coaptation assist body 901 at location 1203, and may reduce or prevent valve regurgitation. In FIGS. 12A and 12B, coaptation assist body 901 is shown in the process of being fixed within the heart valve via a catheter 1204 extending thought the fossa ovalis 1205.

FIG. 13 shows the system after installation within the heart valve, once curvature lock 1001 has been crimped onto tether 905 and the unused portion of tether 905 has been removed. Anchors 906 and 908 are also visible in FIG. 13, anchoring coaptation assist body 901 within the heart valve.

In other embodiments, a system and method are provided for treating mal-coaptation of a heart valve in a patient. The system may include a coaptation assist device such as or similar to coaptation assist device 900, in conjunction with a catheter system through which the coaptation assist device may be deployed within the heart valve.

In an exemplary method of treating mal-coaptation of a heart valve in a patient, an implant, for example coaptation assist device 900, is introduced into the heart valve. The introduction may be through a catheter system as described above. For example, the catheter system may include a guide catheter or sheath such as sheath 301, and one or more delivery catheters for delivering the coaptation assist body, anchors, and other items into the heart. In one application, a coaptation assist body such as coaptation assist body 901 is positioned in the coaptation zone between the anterior and posterior leaflets of the mitral valve. The coaptation assist body may be introduced in a first configuration and deployed in a second configuration. For example, the coaptation assist body may be furled for travel through the catheter system, and unfurled for deployment within the heart valve. The method may include anchoring an upstream end of the coaptation assist body to the annulus of the heart valve, and may also include anchoring the downstream end of the coaptation assist body to ventricular tissue of the heart.

Once the coaptation assist body is disposed within the heart valve, its curvature may be adjusted. For example, once the atrial and ventricular anchors are in place, a crimp delivery catheter may be advanced into the heart and a tether such as tether 905 may be tensioned to cause the curvature of the coaptation assist body to change by changing the distance between the upstream and downstream ends of the coaptation assist body. Once the desired curvature is set, a lock such as crimp 1001 may be engaged to constrain the distance between the upstream and downstream ends of the coaptation assist body. When the installation is complete, the excess tether may then be cut away, and the catheter system removed. The crimping and cutting may be accomplished in a manner similar to that discussed above and illustrated in FIGS. 3I6-3I9.

Preferably, the surgeon implanting the device is provided with sensory information about the beating heart during at least part of the installation of the coaptation assist device. For example, an echocardiogram may provide feedback as to the amount of valve regurgitation that is occurring, so that the surgeon can select the optimum amount of curvature of the coaptation assist body to mitigate, minimize, or eliminate the regurgitation.

While exemplary embodiments have been described in some detail for clarity of understanding, a variety of adaptations and modification will be clear to those of skill in the art. For example, access to the left atrium can be provided at least in part via a minimally invasive entry in the left atrial appendage or thru the left ventricular apex. Additionally, as the devices and methods described herein may be faster, less skill dependent, and/or suitable for sicker patients than alternative valve treatments (that often involve larger access systems or are otherwise more traumatic), and as the implants described herein may be temporarily deployed, these techniques may be used as a short or intermediate-term therapy, giving patients time and allowing recovery so as to be better able to tolerate an alternative treatment. These techniques may also be suitable for re-treatment of patients that have previously had valve therapies. These techniques may also be appropriate for placement in positions at the mitral valve in a patient undergoing coronary artery bypass grafting. Hence, the scope of the present invention is limited solely by the following claims.

What is claimed is:

1. A heart valve repair device, comprising:
an atrial-fixation member comprising an arcuate support base, wherein the atrial-fixation member is configured to be positioned within a left atrium in a deployed configuration, the atrial-fixation member defining a central lumen; and
a valve body extending from a portion of the atrial-fixation member, the baffle valve body having an anterior portion with a surface configured to coapt with at least a portion of a native leaflet of a native heart valve, the valve body having a posterior portion, wherein the valve body extends inward from the atrial-fixation member into the central lumen of the atrial-fixation member, wherein the valve body is configured to extend laterally across at least a portion of a valve opening of the native heart valve, wherein the atrial-fixation member configured to be positioned within the left atrium comprises a greater perimeter than the valve body to engage tissues of the left atrium,
wherein the valve body comprises an insertion volume, wherein the valve body is configured to volumetrically expand from the insertion volume.

2. The device of claim 1, wherein the atrial-fixation member comprises a plurality of frictional elements.

3. The device of claim 1, wherein the valve body is self-expandable.

4. The device of claim 1, wherein the valve body comprises a biocompatible foam.

5. The device of claim 1, wherein the anterior portion of the valve body comprises a convex shape.

6. The device of claim 1, further comprising fibers or layers of materials configured to facilitate tissue ingrowth.

7. The device of claim 1, further comprising at least one fixation mechanism.

8. The device of claim 1, wherein the valve body is configured to expand to dimensions appropriate for placement in between native leaflets.

9. A heart valve repair device, comprising:
an atrial-fixation member comprising a ring-like structure in a deployed configuration, the atrial-fixation member defining a central lumen; and
a valve body extending from a portion of the atrial-fixation member, the valve body having an anterior portion with a surface configured to coapt with at least a portion of a native leaflet of a native heart valve of a heart, the valve body having a posterior portion, wherein the valve body extends inward from the atrial-fixation member into the central lumen of the atrial-fixation member, wherein the valve body is configured to remain within a blood flow path as leaflets of the native heart valve move between an open valve configuration and a closed valve configuration, wherein the atrial-fixation member is configured to be anchored to tissue of the left atrium in the open valve configuration and the closed valve configuration, wherein the valve body is configured to expand within the heart to increase the thickness of the valve body.

10. The device of claim 9, further comprising a plurality of frictional elements.

11. The device of claim 9, wherein the thickness of the valve body varies.

12. The device of claim 9, wherein the thickness of the valve body is between 0.5 mm and 10 mm.

13. The device of claim 9, further comprising at least one fixation mechanism.

14. A heart valve repair device, comprising:
an atrial-fixation member comprising one or more shape memory filaments, the atrial-fixation member defining a central lumen; and
a valve body coupled to the atrial-fixation member, the valve body comprises a first portion with a surface which defines a coaptation surface configured to engage a native leaflet, the valve body comprises a second portion configured to overlie at least a portion of a functionally deficient leaflet, wherein the valve body extends into the central lumen of the atrial-fixation member to approximate a closed position for the functionally deficient leaflet, wherein the atrial-fixation member is configured to be positioned within the left atrium and above the native leaflet and the functionally deficient leaflet, wherein the valve body comprises an insertion volume and a deployed volume greater than the insertion volume, with the valve body volumetrically expanding within the heart so as to increase a thickness of the valve body.

15. The device of claim 14, further comprising fibers or layers of materials at least partially surrounding the valve body.

16. The device of claim 14, wherein the valve body comprises a biocompatible foam.

17. The device of claim 14, further comprising a plurality of frictional engagement elements on the atrial-fixation member.

18. The device of claim 14, wherein the first portion of the valve body comprises a convex shape.

19. The device of claim 14, further comprising at least one fixation mechanism.

20. The device of claim 14, further comprising a biocompatible covering.

* * * * *

UNITED STATES PATENT AND TRADEMARK OFFICE
CERTIFICATE OF CORRECTION

| | | |
|---|---|---|
| PATENT NO. | : 11,413,145 B2 | Page 1 of 1 |
| APPLICATION NO. | : 17/480684 | |
| DATED | : August 16, 2022 | |
| INVENTOR(S) | : Alexander Khairkhahan | |

It is certified that error appears in the above-identified patent and that said Letters Patent is hereby corrected as shown below:

In the Claims

In Column 30, Claim 1, Line 32, before "valve" delete "baffle".

Signed and Sealed this
Twenty-second Day of November, 2022

Katherine Kelly Vidal
*Director of the United States Patent and Trademark Office*